(12) United States Patent
Benson et al.

(10) Patent No.: US 8,309,581 B2
(45) Date of Patent: Nov. 13, 2012

(54) BENZIMIDAZOLE DERIVATIVES

(75) Inventors: Gregory Martin Benson, Therwil (CH);
Konrad Bleicher, Freiburg (DE); Song Feng, Shanghai (CN); Uwe Grether, Efringen-Kirchen (DE); Bernd Kuhn, Reinach BL (CH); Rainer E. Martin, Basel (CH); Jean-Marc Plancher, Hagenthal-le-Bas (FR); Hans Richter, Grenzach-Wyhlen (DE); Markus Rudolph, Basel (CH); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 15 days.

(21) Appl. No.: 12/885,588

(22) Filed: Sep. 20, 2010

(65) Prior Publication Data

US 2011/0077273 A1 Mar. 31, 2011

(30) Foreign Application Priority Data

Sep. 29, 2009 (EP) .................... 09171700

(51) Int. Cl.
*A61K 31/4439* (2006.01)
*A61K 31/4184* (2006.01)
*C07D 401/04* (2006.01)
*C07D 235/18* (2006.01)
*C07D 403/12* (2006.01)
*A61P 3/06* (2006.01)

(52) U.S. Cl. ........ 514/338; 514/381; 514/394; 548/252; 548/310.7

(58) Field of Classification Search .......... None
See application file for complete search history.

(56) References Cited

FOREIGN PATENT DOCUMENTS

| WO | 2008/000643 | 1/2008 |
|---|---|---|
| WO | 2008/101586 | 8/2008 |

OTHER PUBLICATIONS

Liu et al., caplus an 2007:500965.*
Tewari et al., Indian Journal of Chemistry, 45B, 2006, 489-493.*
Zsolnai et al., caplus an 1960:57915.*
Rani et al., caplus an 2009:650586.*
Tong, 2005, caplus an 2005:967873.*
Mjalli et al., 2003, caplus an 2003:737580.*
International Search Report for PCT/EP2010/064217 dated Dec. 16, 2010.
Makishima et al., Science (1999) vol. 284, pp. 1362-1365.
Makishima et al., Mol. Cell (2000) vol. 6 pp. 507-515.
Kast et al., J. Biol. Chem. (2002) vol. 277 pp. 2908-2915.
Ananthanarayanan et al., J. Biol. Chem. (2001) vol. 276 pp. 28857-28865.
Liu et al., J. Clin. Invest. (2003) vol. 112 pp. 1678-1687.
Sinal et al., Cell (2000) vol. 102 pp. 731-744.
Datta et al., J. Biol. Chem. (2006) vol. 281 pp. 807-812.

* cited by examiner

*Primary Examiner* — Sun Jae Loewe
(74) *Attorney, Agent, or Firm* — George W. Johnston; Patricia S. Rocha-Tramaloni; Gene J. Yao

(57) ABSTRACT

The present invention relates to compounds of formula (I),

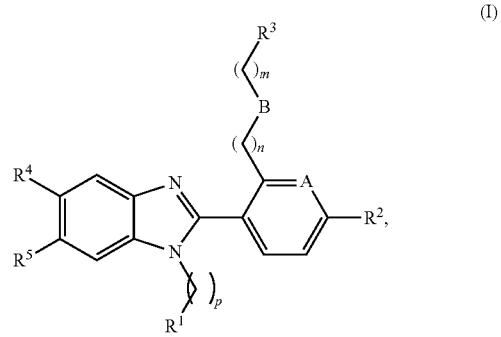

as well as pharmaceutically acceptable salts thereof can be used in the form of pharmaceutical compositions, wherein A, B, $R^1$, $R^2$, $R^3$, $R^4$, $R^5$, n, m and p have the significance defined herein.

13 Claims, No Drawings

BENZIMIDAZOLE DERIVATIVES

PRIORITY TO RELATED APPLICATION(S)

This application claims the benefit of European Patent Application No. 09171700.9, filed Sep. 29, 2009, which is hereby incorporated by reference in its entirety.

FIELD OF THE INVENTION

The present invention is concerned with novel benzimidazole derivatives useful as FXR agonists.

The invention is concerned particularly with compounds of formula (I)

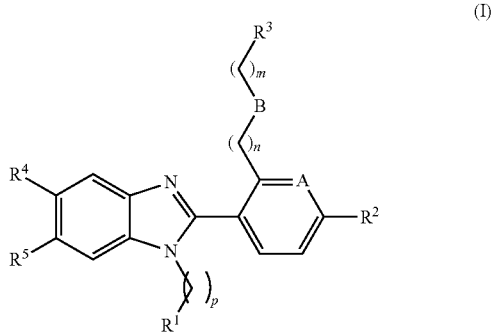

wherein $R^1$, $R^2$, $R^3$, $R^4$, $R^5$, $R^6$, n, m, and p are as defined herein.

BACKGROUND OF THE INVENTION

The Farnesoid-X-receptor (FXR) is a member of the nuclear hormone receptor superfamily of transcription factors. FXR was originally identified as a receptor activated by farnesol, and subsequent studies revealed a major role of FXR as a bile acid receptor (Makishima, M., Okamoto, A. Y., Repa, J. J., Tu, H., Learned, R. M., Luk, A., Hull, M. V., Lustig, K. D., Mangelsdorf, D. J. and Shan, B., *Science*, 1999, 284, 1362-1365). FXR is expressed in liver, intestine, kidney, and the adrenal gland. Four splice isoforms have been cloned in humans.

Among the major bile acids, chenodeoxycholic acid is the most potent FXR agonist. Binding of bile acids or synthetic ligands to FXR induces the transcriptional expression of small heterodimer partner (SHP), an atypical nuclear receptor family member that binds to several other nuclear hormone receptors, including LRH-1 and LXRalpha and blocks their transcriptional functions (Lu, T. T., Makishima, M., Repa, J. J., Schoonjans, K., Kerr, T. A., Auwerx, J. and Mangelsdorf, D. J., *Mol. Cell*, 2000, 6, 507-515). CYP7A1 and CYP8B are enzymes involved in hepatic bile acid synthesis. FXR represses their expression via activation of the SHP pathway. FXR directly induces the expression of bile acid-exporting transporters for the ABC family in hepatocytes, including the bile salt export pump (ABCB11) and the multidrug resistance associated protein 2 (ABCC2) (Kast, H. R., Goodwin, B., Tarr, P. T., Jones, S. A., Anisfeld, A. M., Stoltz, C. M., Tontonoz, P., Kliewer, S., Willson, T. M. and Edwards, P. A., *J. Biol. Chem.*, 2002, 277, 2908-2915; Ananthanarayanan, M., Balasubramanian, N., Makishima, M., Mangelsdorf, D. J. and Suchy, F. J., *J. Biol. Chem.*, 2001, 276, 28857-28865). FXR knockout mice have impaired resistance to bile acid-induced hepatotoxicity and synthetic FXR agonists have been shown to be hepatoprotective in animal models of cholestasis (Liu, Y., Binz, J., Numerick, M. J., Dennis, S., Luo, G., Desai, B., MacKenzie, K. I., Mansfield, T. A., Kliewer, S. A., Goodwin, B. and Jones, S. A., *J. Clin. Invest.*, 2003, 112, 1678-1687; Sinal, C. J., Tohkin, M., Miyata, M., Ward, J. M., Lambert, G. and Gonzalez, F. J., *Cell*, 2000, 102, 731-744). These data show that FXR protects hepatocytes from bile acid toxicity by suppressing both cellular synthesis and import of bile acids and stimulating their biliary excretion.

The process of enterohepatic circulation of bile acids is also a major regulator of serum cholesterol homeostasis. After biosynthesis from cholesterol in the liver, bile acids are secreted with bile into the lumen of the small intestine to aid in the digestion and absorption of fat and fat-soluble vitamins. The ratio of different bile acids determines their ability to solubilize cholesterol. FXR activation decreases the size and changes the composition of the bile acid pool, decreasing the intestinal solubilization of cholesterol, effectively blocking its absorption. Decreased absorption would be expected to result in lower plasma cholesterol levels. Indeed direct inhibitors of cholesterol absorption such as ezetimibe decrease plasma cholesterol, providing some evidence to support this hypothesis. However ezetimibe has limited efficacy which appears due to feedback upregulation of cholesterol synthesis in cells attempting to compensate for depletion of cholesterol. Recent data have shown that FXR opposes this effect in part by directly repressing the expression of HMGCoA reductase via a pathway involving SHP and LRH1 (Datta, S., Wang, L., Moore, D. D. and Osborne, T. F., *J. Biol. Chem.*, 2006, 281, 807-812). FXR also decreases hepatic synthesis of triglycerides by repressing SREBP1-c expression by an alternate pathway involving SHP and LXRalpha. Thus compounds that activate FXR may show superior therapeutic efficacy on plasma cholesterol and triglyceride lowering than current therapies.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

A high proportion of type 2 diabetic patients in the United States have abnormal concentrations of plasma lipoproteins. The prevalence of total cholesterol>240 mg/dl is 37% in diabetic men and 44% in diabetic women and the prevalence for LDL-C>160 mg/dl are 31% and 44%, respectively in these populations. Diabetes is a disease in which a patient's ability to control glucose levels in blood is decreased because of partial impairment in the response to insulin. Type II diabetes (T2D), also called non-insulin dependent diabetes mellitus (NIDDM), accounts for 80-90% of all diabetes cases in developed countries. In T2D, the pancreatic Islets of Langerhans produce insulin but the primary target tissues (muscle, liver and adipose tissue) develop a profound resistance to its effects. The body compensates by producing more insulin ultimately resulting in failure of pancreatic insulin-producing capacity. Thus T2D is a cardiovascular-metabolic syndrome associated with multiple comorbidities including dyslipidemia and insulin resistance, as well as hypertension, endothelial dysfunction and inflammatory atherosclerosis.

The first line treatment for dyslipidemia and diabetes is a low-fat and low-glucose diet, exercise and weight loss. Compliance can be moderate and treatment of the various metabolic deficiencies that develop becomes necessary with, for example, lipid-modulating agents such as statins and fibrates, hypoglycemic drugs such as sulfonylureas and metformin, or insulin sensitizers of the thiazolidinedione (TZD) class of PPARgamma-agonists. Recent studies provide evidence that modulators of FXR may have enhanced therapeutic potential by providing superior normalization of both LDL-C and triglyceride levels, currently achieved only with combinations of existing drugs and, in addition, may avoid feedback effects on cellular cholesterol homeostasis.

SUMMARY OF THE INVENTION

The present invention relates in part to a compound according to formula (I),

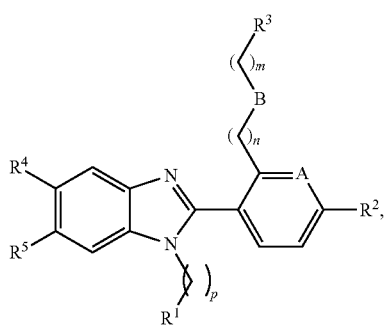

wherein
$R^1$ is selected from the group consisting of: alkyl, hydroxy, hydroxyalkyl, carboxyalkyl, alkoxycarbonylalkyl, cycloalkyl, norbornyl, adamantyl, bicyclo[2.2.2]octanyl, tetrahydropyranyl, phenyl, substituted cycloalkyl, substituted norbornyl, substituted adamantyl, substituted bicyclo[2.2.2]octanyl, substituted tetrahydropyranyl and substituted phenyl, wherein substituted cycloalkyl, substituted norbornyl, substituted adamantyl, substituted bicyclo[2.2.2]octanyl, substituted tetrahydropyranyl and substituted phenyl are substituted with one to three substituents independently selected from the group consisting of: alkyl, haloalkyl, halogen, hydroxy, alkoxy, hydroxyalkyl, carboxy, carboxyalkyl, carboxyalkoxy, alkoxycarbonyl, alkoxycarbonylalkyl, alkoxycarbonylalkoxy, cyano, tetrazolyl and tetrazolylalkyl;
$R^2$ is selected from the group consisting of: hydrogen, alkyl and halogen;
$R^3$ is selected from the group consisting of: alkyl, cycloalkyl, carboxy, carboxyalkyl, alkoxycarbonyl, alkoxycarbonylalkyl, tetrahydropyranyl, phenyl, thiophenyl, pyridinyl, carboxypyridinyl, tetrazolylpyridinyl, substituted cycloalkyl, substituted tetrahydropyranyl, substituted phenyl and substituted thiophenyl, wherein substituted cycloalkyl, substituted tetrahydropyranyl, substituted phenyl and substituted thiophenyl are substituted with one to three substituents independently selected from the group consisting of: alkyl, haloalkyl, halogen, alkoxy, hydroxy, hydroxyalkyl, carboxy, carboxyalkyl, carboxyalkoxy, carboxycycloalkylalkoxy, alkoxycarbonyl, alkoxycarbonylalkyl, cyano, tetrazolyl and tetrazolylalkyl;
$R^4$ is hydrogen or halogen;
$R^5$ is hydrogen or halogen;
$R^6$ is hydrogen or alkyl;
$R^7$ is hydrogen or alkyl;
$R^8$ is hydrogen or alkyl;
$R^9$ is hydrogen or alkyl;
$R^{10}$ is hydrogen or alkyl;
A is carbon or nitrogen;
B is selected from the group consisting of: —O—, —S—, —NR$^6$—, —C(O)NR$^7$—, —S(O)$_2$NR$^8$—, —CR$^9$R$^{10}$— and —C≡C—;
n is zero, 1 or 2;
m is zero, 1 or 2; and
p is 1 or 2;
or a pharmaceutically acceptable salt thereof;
with the proviso that, when $R^3$ is methyl or ethyl, $R^2$ is halogen or alkyl; and
with the further proviso that 1-benzyl-2-(2-benzyloxy-phenyl)-1H-benzoimidazole is excluded. Further objects of the present invention are pharmaceutically acceptable esters of the compounds of formula (I), the use of compounds of formula (I), or pharmaceutically acceptable salts and esters thereof, as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of atherosclerosis, diabetes, non-alcoholic steatohepatitis or diabetic nephropathy and the use of the said compounds, salts or esters for the production of medicaments for the treatment or prophylaxis of atherosclerosis, diabetes, non-alcoholic steatohepatitis or diabetic nephropathy.

DETAILED DESCRIPTION OF THE INVENTION

The present invention relates in part to a compound according to formula (I),

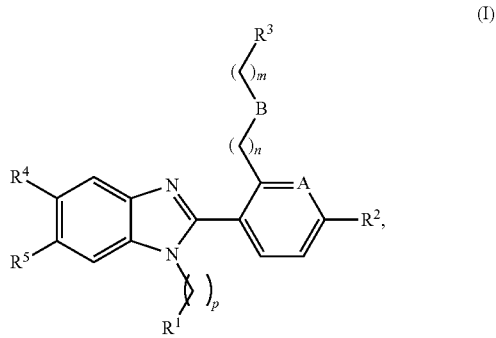

wherein
$R^1$ is selected from the group consisting of: alkyl, hydroxy, hydroxyalkyl, carboxyalkyl, alkoxycarbonylalkyl, cycloalkyl, norbornyl, adamantyl, bicyclo[2.2.2]octanyl, tetrahydropyranyl, phenyl, substituted cycloalkyl, substituted norbornyl, substituted adamantyl, substituted bicyclo[2.2.2]octanyl, substituted tetrahydropyranyl and substituted phenyl, wherein substituted cycloalkyl, substituted norbornyl, substituted adamantyl, substituted bicyclo[2.2.2]octanyl, substituted tetrahydropyranyl and substituted phenyl are substituted with one to three substituents independently selected from the group consisting of: alkyl, haloalkyl, halogen, hydroxy, alkoxy, hydroxyalkyl, carboxy, carboxyalkyl, carboxyalkoxy, alkoxycarbonyl, alkoxycarbonylalkyl, alkoxycarbonylalkoxy, cyano, tetrazolyl and tetrazolylalkyl;

$R^2$ is selected from the group consisting of: hydrogen, alkyl and halogen;

$R^3$ is selected from the group consisting of: alkyl, cycloalkyl, carboxy, carboxyalkyl, alkoxycarbonyl, alkoxycarbonylalkyl, tetrahydropyranyl, phenyl, thiophenyl, pyridinyl, carboxypyridinyl, tetrazolylpyridinyl, substituted cycloalkyl, substituted tetrahydropyranyl, substituted phenyl and substituted thiophenyl, wherein substituted cycloalkyl, substituted tetrahydropyranyl, substituted phenyl and substituted thiophenyl are substituted with one to three substituents independently selected from the group consisting of: alkyl, haloalkyl, halogen, alkoxy, hydroxy, hydroxyalkyl, carboxy, carboxyalkyl, carboxyalkoxy, carboxycycloalkylalkoxy, alkoxycarbonyl, alkoxycarbonylalkyl, cyano, tetrazolyl and tetrazolylalkyl;

$R^4$ is hydrogen or halogen;

$R^5$ is hydrogen or halogen;

$R^6$ is hydrogen or alkyl;

$R^7$ is hydrogen or alkyl;

$R^8$ is hydrogen or alkyl;

$R^9$ is hydrogen or alkyl;

$R^{10}$ is hydrogen or alkyl;

A is carbon or nitrogen;

B is selected from the group consisting of: —O—, —S—, —NR$^6$—, —C(O)NR$^7$—, —S(O)$_2$NR$^8$—, —CR$^9$R$^{10}$— and —C≡C—;

n is zero, 1 or 2;

m is zero, 1 or 2; and p is 1 or 2;

or a pharmaceutically acceptable salt thereof;

with the proviso that, when $R^3$ is methyl or ethyl, $R^2$ is halogen or alkyl; and with the further proviso that 1-benzyl-2-(2-benzyloxy-phenyl)-1H-benzoimidazole is excluded.

The term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples are methyl, ethyl, propyl, isopropyl, butyl, isobutyl, tert-butyl, the isomeric pentyls, the isomeric hexyls, the isomeric heptyls and the isomeric octyls. Preferred alkyl are methyl, ethyl, isopropyl, tert-butyl and isomeric pentyls and particularly. Particularly preferred alkyl are methyl and tert-butyl.

The term "cycloalkyl", alone or in combination, signifies a cycloalkyl ring with 3 to 8 carbon atoms and preferably a cycloalkyl ring with 3 to 6 carbon atoms. Examples are cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. Preferred cycloalkyl rings are cyclopropyl, cyclopentyl, cyclohexyl and cycloheptyl. Particularly preferred cycloalkyl rings are cyclopentyl and cyclohexyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy. Preferred alkoxy are preferably methoxy and ethoxy. A particularly preferred alkoxy is methoxy.

The term "hydroxy", alone or in combination, signifies the —OH group.

The term "hydroxyalkyl", alone or in combination, signifies an alkyl group as defined before, wherein one or more hydrogen atoms is replaced by a hydroxy group. Examples of hydroxyalkyl are hydroxymethyl, hydroxyethyl, hydroxypropyl and dihydroxypropyl.

The terms "halogen", alone or in combination, signifies fluorine, chlorine, bromine or iodine. Preferred halogen are fluorine or chlorine.

The term "haloalkyl", alone or in combination, signifies an alkyl group as defined before, wherein one or more hydrogen atoms is replaced by a halogen atom. Examples of haloalkyl are fluoromethyl, difluoromethyl, trifluoromethyl, trifluoroethyl, trifluoromethylethyl and pentafluoroethyl.

The term "carboxy", alone or in combination, signifies the —C(O)OH group.

The term "carbonyl", alone or in combination, signifies the —C(O)— group.

The term "sulfonyl", alone or in combination, signifies the —S(O)$_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particularly preferred pharmaceutically acceptable salts of compounds of formula (I) are the hydrochloride salts, methanesulfonic acid salts and citric acid salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred pharmaceutically acceptable esters of compounds of formula (I) are methyl and ethyl esters.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Preferred are the compounds according to formula (I) as described above and pharmaceutically acceptable salts and esters thereof. Further preferred are the compounds according to formula (I) as described above and pharmaceutically acceptable salts thereof, particularly the compounds according to formula (I) as described above.

Also preferred are compounds according to formula (I) as described above, wherein $R^1$ is selected from the group consisting of: alkyl, carboxyalkyl, cycloalkyl, norbornyl, adamantyl, bicyclo[2.2.2]octanyl, tetrahydropyranyl, phenyl, substituted cycloalkyl and substituted phenyl, wherein substituted cycloalkyl and substituted phenyl are substituted with one to three substituents independently selected from the group consisting of: alkyl, halogen, carboxy, carboxyalkyl, carboxyalkoxy, and tetrazolyl.

Further preferred are compounds according to formula (I) as described above, wherein $R^1$ is selected from the group consisting of: alkyl, carboxyalkyl, cycloalkyl, tetrahydropyranyl, phenyl, substituted cycloalkyl and substituted phenyl, wherein substituted cycloalkyl and substituted phenyl are substituted with one to three substituents independently selected from the group consisting of: alkyl, halogen, carboxy, carboxyalkyl, carboxyalkoxy, and tetrazolyl.

Particularly preferred are compounds according to formula (I) as described above, wherein $R^1$ is selected from the group consisting of: alkyl, cycloalkyl, phenyl and substituted phenyl, wherein substituted phenyl is phenyl substituted with one to three, preferably one to two, substituents independently selected from the group consisting of: halogen, carboxyalkyl and tetrazolyl.

Moreover preferred are compounds according to formula (I) as described above, wherein $R^1$ is selected from the group consisting of: alkyl, cycloalkyl and substituted phenyl, wherein substituted phenyl is phenyl substituted with one to three, preferably one to two, particularly two, substituents independently selected from halogen and tetrazolyl.

Furthermore preferred are those compounds according to formula (I) as described above, wherein $R^1$ is cycloalkyl.

Another preferred embodiment of the present invention are the compounds according to formula (I) as described above, wherein $R^3$ is selected from the group consisting of: alkyl, cycloalkyl, carboxyalkyl, tetrahydropyranyl, substituted cycloalkyl and substituted phenyl, wherein substituted cycloalkyl and substituted phenyl are substituted with one to three, preferably one to two, substituents independently selected from the group consisting of: haloalkyl, halogen, alkoxy, carboxy, carboxyalkoxy and tetrazolyl, wherein in case $R^3$ is methyl or ethyl, then $R^2$ is halogen or alkyl.

Particularly preferred are those compounds according to formula (I) as described above, wherein $R^3$ is cycloalkyl or substituted phenyl wherein substituted phenyl is phenyl substituted with one to three, preferably one to two, substituents independently selected from the group consisting of: halogen, carboxy, carboxyalkoxy and tetrazolyl.

More preferred are those compounds according to formula (I) as described above, wherein $R^3$ is substituted phenyl wherein substituted phenyl is phenyl substituted with one to three substituents, preferably one to two, more preferably two, independently selected from halogen and tetrazolyl.

Moreover preferred are compounds according to formula (I) as described above, wherein $R^3$ is substituted phenyl wherein substituted phenyl is phenyl substituted with one halogen and one tetrazolyl.

Preferred are compounds according to formula (I) as described above, wherein B is selected from the group consisting of: —O—, —C(O)$NR^7$—, —$CR^8R^9$— and —C≡C—.

Particularly preferred are those compounds according to formula (I) as described above, wherein B is —O—.

Also particularly preferred are compounds according to formula (I) as described above, wherein B is —C(O)$NR^7$—.

Furthermore preferred are compounds of formula (Ia).

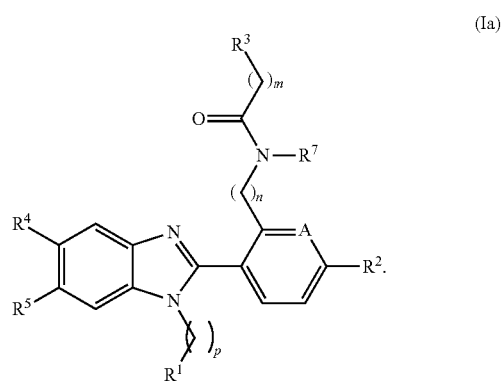

(Ia)

Also furthermore preferred are compounds of formula (Ib).

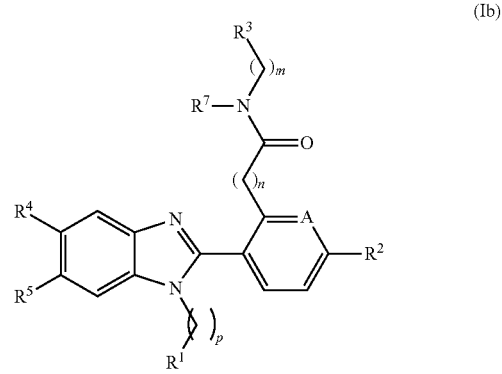

(Ib)

Preferred are also compounds according to formula (I) as described above, wherein A is carbon.

Also preferred are compounds according to formula (I) as described above, wherein $R^2$ is halogen.

Also preferred are compounds according to formula (I) as described above, wherein $R^4$ is halogen.

Also preferred are compounds according to formula (I) as described above, wherein $R^5$ is halogen.

Another preferred embodiment of the present invention are the compounds according to formula (I) as described above, wherein n is zero or 1.

Examples of preferred compounds according to formula (I) as described above are selected from the group consisting of:

1-Cyclohexylmethyl-2-(2-cyclopentylmethoxy-pyridin-3-yl)-5,6-difluoro-1H-benzoimidazole;

1-Cyclohexylmethyl-2-(2-cyclopropylmethoxy-pyridin-3-yl)-5,6-difluoro-1H-benzoimidazole;

2-[2-(2-Chloro-benzyloxy)-pyridin-3-yl]-1-cyclohexylmethyl-5,6-difluoro-1H-benzoimidazole;

4-[3-(1-Cyclohexylmethyl-5,6-difluoro-1H-benzoimidazol-2-yl)-pyridin-2-yloxymethyl]-benzoic acid;

{4-[3-(1-Cyclohexylmethyl-5,6-difluoro-1H-benzoimidazol-2-yl)-pyridin-2-yloxymethyl]-phenoxy}-acetic acid;
1-Benzyl-2-[2-(2-chloro-benzyloxy)-pyridin-3-yl]-5,6-difluoro-1H-benzoimidazole;
1-Benzyl-2-(2-cyclopentylmethoxy-pyridin-3-yl)-5,6-difluoro-1H-benzoimidazole;
1-Benzyl-2-(2-cyclopropylmethoxy-pyridin-3-yl)-5,6-difluoro-1H-benzoimidazole;
4-[3-(1-Benzyl-5,6-difluoro-1H-benzoimidazol-2-yl)-pyridin-2-yloxymethyl]-benzoic acid;
{4-[3-(1-Benzyl-5,6-difluoro-1H-benzoimidazol-2-yl)-pyridin-2-yloxymethyl]-phenoxy}-acetic acid;
1-(3-Chloro-benzyl)-2-[2-(2-chloro-benzyloxy)-pyridin-3-yl]-5,6-difluoro-1H-benzoimidazole;
1-(3-Chloro-benzyl)-2-(2-cyclopentylmethoxy-pyridin-3-yl)-5,6-difluoro-1H-benzoimidazole;
1-(3-Chloro-benzyl)-2-(2-cyclopropylmethoxy-pyridin-3-yl)-5,6-difluoro-1H-benzoimidazole;
4-{3-[1-(3-Chloro-benzyl)-5,6-difluoro-1H-benzoimidazol-2-yl]-pyridin-2-yloxymethyl}-benzoic acid;
(4-{3-[1-(3-Chloro-benzyl)-5,6-difluoro-1H-benzoimidazol-2-yl]-pyridin-2-yloxymethyl}-phenoxy)-acetic acid;
3-{4-[2-(2-Cyclopropylmethoxy-pyridin-3-yl)-5,6-difluoro-benzoimidazol-1-ylmethyl]-phenyl}-propionic acid;
3-(4-{2-[2 (2-Chloro-benzyloxy)-pyridin-3-yl]-5,6-difluoro-benzoimidazol-1-ylmethyl}-phenyl)-propionic acid;
3-{4-[2-(2-Cyclopentylmethoxy-pyridin-3-yl)-5,6-difluoro-benzoimidazol-1-ylmethyl]-phenyl}-propionic acid;
2-[4-Chloro-2-(2-chloro-benzyloxy)-phenyl]-1-cyclohexylmethyl-5,6-difluoro-1H-benzoimidazole;
2-(4-Chloro-2-cyclopentylmethoxy-phenyl)-1-cyclohexylmethyl-5,6-difluoro-1H-benzoimidazole;
2-(4-Chloro-2-cyclopropylmethoxy-phenyl)-1-cyclohexylmethyl-5,6-difluoro-1H-benzoimidazole;
2-(4-Chloro-2-cyclohexylmethoxy-phenyl)-1-cyclohexylmethyl-5,6-difluoro-1H-benzoimidazole;
4-[5-Chloro-2-(1-cyclohexylmethyl-5,6-difluoro-1H-benzoimidazol-2-yl)-phenoxymethyl]-benzoic acid;
3-[5-Chloro-2-(1-cyclohexylmethyl-5,6-difluoro-1H-benzoimidazol-2-yl)-phenoxymethyl]-benzoic acid;
{4-[5-Chloro-2-(1-cyclohexylmethyl-5,6-difluoro-1H-benzoimidazol-2-yl)-phenoxymethyl]-phenoxy}-acetic acid;
6-[5-Chloro-2-(1-cyclohexylmethyl-5,6-difluoro-1H-benzoimidazol-2-yl)-phenoxy]-hexanoic acid;
4-{2-[5-Chloro-2-(1-cyclohexylmethyl-5,6-difluoro-1H-benzoimidazol-2-yl)-phenoxy]-ethyl}-benzoic acid;
{4-[5-Chloro-2-(1-cyclohexylmethyl-5,6-difluoro-1H-benzoimidazol-2-yl)-phenoxymethyl]-phenyl}-acetic acid;
4-[5-Chloro-2-(1-cyclohexylmethyl-5,6-difluoro-1H-benzoimidazol-2-yl)-phenoxymethyl]-cyclohexanecarboxylic acid;
2-{4-Chloro-2-[3-(1H-tetrazol-5-yl)-benzyloxy]-phenyl}-1-cyclohexylmethyl-5,6-difluoro-1H-benzoimidazole;
2-{4-Chloro-2-[4-(1H-tetrazol-5-yl)-benzyloxy]-phenyl}-1-cyclohexylmethyl-5,6-difluoro-1H-benzoimidazole;
2-{4-Chloro-2-[2-fluoro-4-(1H-tetrazol-5-yl)-benzyloxy]-phenyl}-1-cyclohexylmethyl-5,6-difluoro-1H-benzoimidazole;
2-{4-Chloro-2-[3-fluoro-4-(1H-tetrazol-5-yl)-benzyloxy]-phenyl}-1-cyclohexylmethyl-5,6-difluoro-1H-benzoimidazole;
1-Cyclohexylmethyl-5,6-difluoro-2-{2-[2-fluoro-4-(1H-tetrazol-5-yl)-benzyloxy]-phenyl}-1H-benzoimidazole;
2-{4-Chloro-2-[2-methoxy-4-(1H-tetrazol-5-yl)-benzyloxy]-phenyl}-1-cyclohexylmethyl-5,6-difluoro-1H-benzoimidazole;
2-(4-Chloro-2-{2-[4-(1H-tetrazol-5-yl)-phenyl]-ethoxy}-phenyl)-1-cyclohexylmethyl-5,6-difluoro-1H-benzoimidazole;
2-{4-Chloro-2-[5-(1H-tetrazol-5-yl)-thiophen-2-yl-methoxy]-phenyl}-1-cyclohexylmethyl-5,6-difluoro-1H-benzoimidazole;
2-{4-Chloro-2-[4-(1H-tetrazol-5-yl)-2-trifluoromethyl-benzyloxy]-phenyl}-1-cyclohexylmethyl-5,6-difluoro-1H-benzoimidazole;
2-{4-Chloro-2-[2-fluoro-4-(1H-tetrazol-5-yl)-benzyloxy]-phenyl}-1-cyclohexylmethyl-1H-benzoimidazole;
1-Cyclohexylmethyl-5,6-difluoro-2-{2-[2-fluoro-4-(1H-tetrazol-5-yl)-phenoxymethyl]-phenyl}-1H-benzoimidazole;
1-Cyclohexylmethyl-5,6-difluoro-2-{2-[3-fluoro-4-(1H-tetrazol-5-yl)-phenoxymethyl]-phenyl}-1H-benzoimidazole;
2-{4-Chloro-2-[2-fluoro-4-(1H-tetrazol-5-yl)-benzyloxy]-phenyl}-1-cyclopentylmethyl-5,6-difluoro-1H-benzoimidazole;
2-{4-Chloro-2-[2-fluoro-4-(1H-tetrazol-5-yl)-benzyloxy]-phenyl}-1-(2-cyclohexyl-ethyl)-5,6-difluoro-1H-benzoimidazole;
2-{4-Chloro-2-[2-fluoro-4-(1H-tetrazol-5-yl)-benzyloxy]-phenyl}-5,6-difluoro-1-pentyl-1H-benzoimidazole;
2-{4-Chloro-2-[2-fluoro-4-(1H-tetrazol-5-yl)-benzyloxy]-phenyl}-5,6-difluoro-1-(tetrahydro-pyran-2-ylmethyl)-1H-benzoimidazole;
2-{4-Chloro-2-[2-fluoro-4-(1H-tetrazol-5-yl)-benzyloxy]-phenyl}-1-(2,2-dimethyl-propyl)-5,6-difluoro-1H-benzoimidazole;
2-{4-Chloro-2-[2-fluoro-4-(1H-tetrazol-5-yl)-benzyloxy]-phenyl}-5,6-difluoro-1-(tetrahydro-pyran-4-ylmethyl)-1H-benzoimidazole;
1-Benzyl-2-[4-chloro-2-(2-chloro-benzyloxy)-phenyl]-5,6-difluoro-1H-benzoimidazole;
1-Benzyl-2-(4-chloro-2-cyclopentylmethoxy-phenyl)-5,6-difluoro-1H-benzoimidazole;
1-Benzyl-2-(4-chloro-2-cyclopropylmethoxy-phenyl)-5,6-difluoro-1H-benzoimidazole;
4-[2-(1-Benzyl-5,6-difluoro-1H-benzoimidazol-2-yl)-5-chloro-phenoxymethyl]-benzoic acid;
{4-[2-(1-Benzyl-5,6-difluoro-1H-benzoimidazol-2-yl)-5-chloro-phenoxymethyl]-phenoxy}-acetic acid;
1-(3-Chloro-benzyl)-2-[4-chloro-2-(2-chloro-benzyloxy)-phenyl]-5,6-difluoro-1H-benzoimidazole;
1-(3-Chloro-benzyl)-2-(4-chloro-2-cyclopentylmethoxy-phenyl)-5,6-difluoro-1H-benzoimidazole;
1-(3-Chloro-benzyl)-2-(4-chloro-2-cyclopropylmethoxy-phenyl)-5,6-difluoro-1H-benzoimidazole;
4-{5-Chloro-2-[1-(3-chloro-benzyl)-5,6-difluoro-1H-benzoimidazol-2-yl]-phenoxymethyl}-benzoic acid;
(4-{5-Chloro-2-[1-(3-chloro-benzyl)-5,6-difluoro-1H-benzoimidazol-2-yl]-phenoxymethyl}-phenoxy)-acetic acid;
3-(4-{2-[4-Chloro-2-(2-chloro-benzyloxy)-phenyl]-5,6-difluoro-benzoimidazol-1-ylmethyl}-phenyl)-propionic acid;
3-{4-[2-(4-Chloro-2-cyclopentylmethoxy-phenyl)-5,6-difluoro-benzoimidazol-1-ylmethyl]-phenyl}-propionic acid;
3-{4-[2-(4-Chloro-2-cyclopropylmethoxy-phenyl)-5,6-difluoro-benzoimidazol-1-ylmethyl]-phenyl}-propionic acid;
3-[2-(4-Chloro-2-cyclopentylmethoxy-phenyl)-5,6-difluoro-benzoimidazol-1-ylmethyl]-benzoic acid;
4-[2-(4-Chloro-2-cyclopentylmethoxy-phenyl)-5,6-difluoro-benzoimidazol-1-ylmethyl]-benzoic acid;

{4-[2-(4-Chloro-2-cyclopentylmethoxy-phenyl)-5,6-difluoro-benzoimidazol-1-ylmethyl]-phenyl}-acetic acid;
{4-[2-(4-Chloro-2-cyclopentylmethoxy-phenyl)-5,6-difluoro-benzoimidazol-1-ylmethyl]-phenoxy}-acetic acid;
6-[2-(4-Chloro-2-cyclopentylmethoxy-phenyl)-5,6-difluoro-benzoimidazol-1-yl]-hexanoic acid;
4-[2-(4-Chloro-2-cyclopentylmethoxy-phenyl)-5,6-difluoro-benzoimidazol-1-ylmethyl]-cyclohexanecarboxylic acid;
2-(4-Chloro-2-cyclopentylmethoxy-phenyl)-5,6-difluoro-1-[3-(1H-tetrazol-5-yl)-benzyl]-1H-benzoimidazole;
2-(4-Chloro-2-cyclopentylmethoxy-phenyl)-5,6-difluoro-1-[4-(1H-tetrazol-5-yl)-benzyl]-1H-benzoimidazole;
2-(4-Chloro-2-cyclopentylmethoxy-phenyl)-5,6-difluoro-1-[3-fluoro-4-(1H-tetrazol-5-yl)-benzyl]-1H-benzoimidazole;
2-(4-Chloro-2-cyclopentylmethoxy-phenyl)-5,6-difluoro-1-[2-fluoro-4-(1H-tetrazol-5-yl)-benzyl]-1H-benzoimidazole;
2-(4-Chloro-2-methoxy-phenyl)-5,6-difluoro-1-[2-fluoro-4-(1H-tetrazol-5-yl)-benzyl]-1H-benzoimidazole;
2-{4-Chloro-2-[4-(1H-tetrazol-5-yl)-phenylethynyl]-phenyl}-1-cyclohexylmethyl-5,6-difluoro-1H-benzoimidazole;
2-(4-Chloro-2-{2-[4-(1H-tetrazol-5-yl)-phenyl]-ethyl}-phenyl)-1-cyclohexylmethyl-5,6-difluoro-1H-benzoimidazole;
2-(4-Chloro-2-{2-[4-(1H-tetrazol-5-yl)-phenyl]-ethyl}-phenyl)-1-cyclohexylmethyl-1H-benzoimidazole;
4-{2-[5-Chloro-2-(1-cyclohexylmethyl-1H-benzoimidazol-2-yl)-phenyl]-ethyl}-benzoic acid;
1-Cyclohexylmethyl-5,6-difluoro-2-(2-{2-[4-(1H-tetrazol-5-yl)-phenyl]-ethyl}-phenyl)-1H-benzoimidazole;
4-{2-[2-(1-Cyclohexylmethyl-5,6-difluoro-1H-benzoimidazol-2-yl)-phenyl]-ethyl}-benzoic acid;
4-{2-[2-(1-Cyclohexylmethyl-1H-benzoimidazol-2-yl)-phenyl]-ethyl}-benzoic acid;
(4-{2-[2-(1-Cyclohexylmethyl-1H-benzoimidazol-2-yl)-phenyl]-ethyl}-phenoxy)-acetic acid;
1-Cyclohexylmethyl-2-(2-{2-[4-(1H-tetrazol-5-yl)-phenyl]-ethyl}-phenyl)-1H-benzoimidazole;
1-(4,4-Difluoro-cyclohexylmethyl)-2-(2-{2-[4-(1H-tetrazol-5-yl)-phenyl]-ethyl}-phenyl)-1H-benzoimidazole;
1-(4-Methyl-cyclohexylmethyl)-2-(2-{2-[4-(1H-tetrazol-5-yl)-phenyl]-ethyl}-phenyl)-1H-benzoimidazole;
1-(2-Cyclohexyl-ethyl)-2-(2-{2-[4-(1H-tetrazol-5-yl)-phenyl]-ethyl}-phenyl)-1H-benzoimidazole;
N-[5-Chloro-2-(1-cyclohexylmethyl-5,6-difluoro-1H-benzoimidazol-2-yl)-phenyl]-2-fluoro-4-(1H-tetrazol-5-yl)-benzamide;
N-[5-Chloro-2-(1-cyclohexylmethyl-5,6-difluoro-1H-benzoimidazol-2-yl)-phenyl]-3-fluoro-4-(1H-tetrazol-5-yl)-benzamide;
2-(1-Cyclohexylmethyl-5,6-difluoro-1H-benzoimidazol-2-yl)-N-[2-fluoro-4-(1H-tetrazol-5-yl)-phenyl]-benzamide;
2-(4-Chloro-2-cyclohexylmethoxy-phenyl)-5,6-difluoro-1-[2-fluoro-4-(1H-tetrazol-5-yl)-benzyl]-1H-benzoimidazole;
2-[4-Chloro-2-(2-ethyl-butoxy)-phenyl]-5,6-difluoro-1-[2-fluoro-4-(1H-tetrazol-5-yl)-benzyl]-1H-benzoimidazole;
2-(4-Chloro-2-cyclopropylmethoxy-phenyl)-5,6-difluoro-1-[2-fluoro-4-(1H-tetrazol-5-yl)-benzyl]-1H-benzoimidazole;
2-[4-Chloro-2-(tetrahydro-pyran-4-ylmethoxy)-phenyl]-5,6-difluoro-1-[2-fluoro-4-(1H-tetrazol-5-yl)-benzyl]-1H-benzoimidazole;
2-(4-Chloro-2-propoxy-phenyl)-5,6-difluoro-1-[2-fluoro-4-(1H-tetrazol-5-yl)-benzyl]-1H-benzoimidazole;
2-(4-Chloro-2-cyclobutylmethoxy-phenyl)-5,6-difluoro-1-[2-fluoro-4-(1H-tetrazol-5-yl)-benzyl]-1H-benzoimidazole;
2-[4-Chloro-2-(tetrahydro-pyran-2-ylmethoxy)-phenyl]-5,6-difluoro-1-[2-fluoro-4-(1H-tetrazol-5-yl)-benzyl]-1H-benzoimidazole;
2-(2-Cyclopentylmethoxy-phenyl)-5,6-difluoro-1-[2-fluoro-4-(1H-tetrazol-5-yl)-benzyl]-1H-benzoimidazole;
2-(4-Chloro-2-cyclopentylmethoxy-phenyl)-1-[2-fluoro-4-(1H-tetrazol-5-yl)-benzyl]-1H-benzoimidazole; and
2-(4-Chloro-2-cyclohexyloxy-phenyl)-5,6-difluoro-1-[2-fluoro-4-(1H-tetrazol-5-yl)-benzyl]-1H-benzoimidazole.

Examples of especially preferred compounds according to formula (I) as described above are selected from the group consisting of:
2-(4-Chloro-2-cyclopentylmethoxy-phenyl)-1-cyclohexylmethyl-5,6-difluoro-1H-benzoimidazole;
2-(4-Chloro-2-cyclohexylmethoxy-phenyl)-1-cyclohexylmethyl-5,6-difluoro-1H-benzoimidazole;
4-[5-Chloro-2-(1-cyclohexylmethyl-5,6-difluoro-1H-benzoimidazol-2-yl)-phenoxymethyl]-benzoic acid;
{4-[5-Chloro-2-(1-cyclohexylmethyl-5,6-difluoro-1H-benzoimidazol-2-yl)-phenoxymethyl]-phenoxy}-acetic acid;
2-{4-Chloro-2-[4-(1H-tetrazol-5-yl)-benzyloxy]-phenyl}-1-cyclohexylmethyl-5,6-difluoro-1H-benzoimidazole;
2-{4-Chloro-2-[2-fluoro-4-(1H-tetrazol-5-yl)-benzyloxy]-phenyl}-1-cyclohexylmethyl-5,6-difluoro-1H-benzoimidazole;
2-{4-Chloro-2-[3-fluoro-4-(1H-tetrazol-5-yl)-benzyloxy]-phenyl}-1-cyclohexylmethyl-5,6-difluoro-1H-benzoimidazole;
1-Cyclohexylmethyl-5,6-difluoro-2-{2-[2-fluoro-4-(1H-tetrazol-5-yl)-phenoxymethyl]-phenyl}-1H-benzoimidazole;
2-{4-Chloro-2-[2-fluoro-4-(1H-tetrazol-5-yl)-benzyloxy]-phenyl}-1-(2-cyclohexyl-ethyl)-5,6-difluoro-1H-benzoimidazole;
2-{4-Chloro-2-[2-fluoro-4-(1H-tetrazol-5-yl)-benzyloxy]-phenyl}-1-(2,2-dimethyl-propyl)-5,6-difluoro-1H-benzoimidazole;
2-(4-Chloro-2-cyclopentylmethoxy-phenyl)-5,6-difluoro-1-[3-fluoro-4-(1H-tetrazol-5-yl)-benzyl]-1H-benzoimidazole;
2-(4-Chloro-2-cyclopentylmethoxy-phenyl)-5,6-difluoro-1-[2-fluoro-4-(1H-tetrazol-5-yl)-benzyl]-1H-benzoimidazole;
2-(4-Chloro-2-{2-[4-(1H-tetrazol-5-yl)-phenyl]-ethyl}-phenyl)-1-cyclohexylmethyl-1H-benzoimidazole;
N-[5-Chloro-2-(1-cyclohexylmethyl-5,6-difluoro-1H-benzoimidazol-2-yl)-phenyl]-2-fluoro-4-(1H-tetrazol-5-yl)-benzamide; and N-[5-Chloro-2-(1-cyclohexylmethyl-5,6-difluoro-1H-benzoimidazol-2-yl)-phenyl]-3-fluoro-4-(1H-tetrazol-5-yl)-benzamide.

Processes for the manufacture of compounds of formula (I) are an object of the invention.

The preparation of compounds of formula (I) of the present invention may be carried out in sequential or convergent synthetic routes. Syntheses of the compounds of the invention are shown in, but not limited to, the following schemes. The skills required for carrying out the reactions and purifications of the resulting products are known to those skilled in the art. The substituents and indices used in the following description of the processes have the significance given herein.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, 2nd Ed., 1991, Wiley N.Y.) can be introduced before the critical step, applying methods well known in the art. Such protecting groups can be removed at a later stage of the synthesis using standard methods described in the literature.

Compounds of formula II-A and III-A can be prepared according to Scheme 1.

Benzimidazoles of the general structure 3 are either commercially available or accessible by methods known in the art, e.g. via reaction (step a) of phenylene diamines derivatives 1 with 2-bromo-benzoic acids derivatives 2 using an acid such as polyphosphoric acid, in the presence or not of a solvent such as o-xylene. Compounds of the general structure 3 can be alkylated (step b) with compounds of general formula XVII using a base, e.g. sodium hydride or cesium carbonate, in a solvent such as N,N-dimethylformamide or acetone, to give intermediates 4. LG signifies a leaving group such as a halogen (e.g. bromine, chlorine or iodine) or a sulfonate group (e.g. mesylate, tosylate or triflate). If compounds of general formula XVII are commercially not available they can be prepared by methods known in the literature.

Intermediates 4 can be converted into compounds of formula II-A by e.g. Sonogashira-type coupling of 4 (step c) with alkynes in the presence of a base such as triethylamine and using a suitable catalyst system such as a mixture of bis (triphenylphosphine)palladium(II) dichloride and copper(I) iodide in a solvent such as tetrahydrofuran. Compounds of formula II-A can be further converted into compounds of formula III-A by reducing the carbon-carbon triple bond (step d) by e.g. hydrogenation using a catalyst such as palladium on charcoal in a solvent such as ethyl acetate or an alcohol such as methanol or ethanol or mixtures of said solvents.

Compounds of the general formula IV-A to IV-C can be prepared according to Scheme 2.

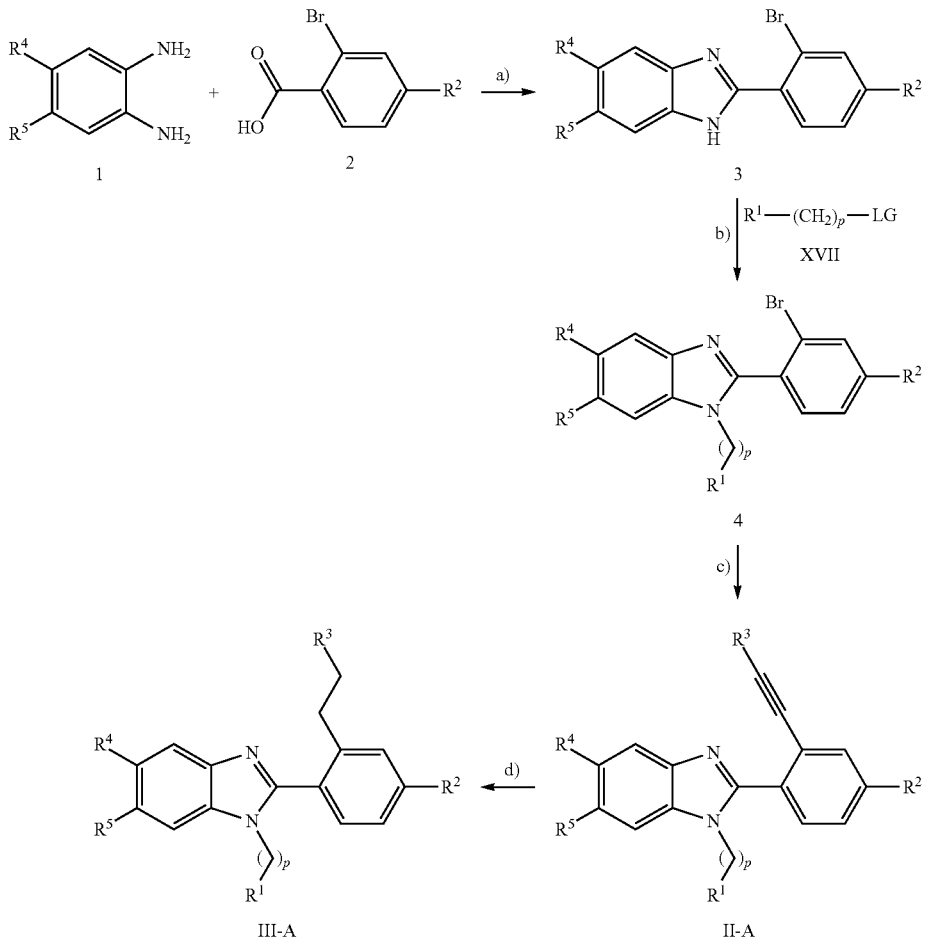

Scheme 2

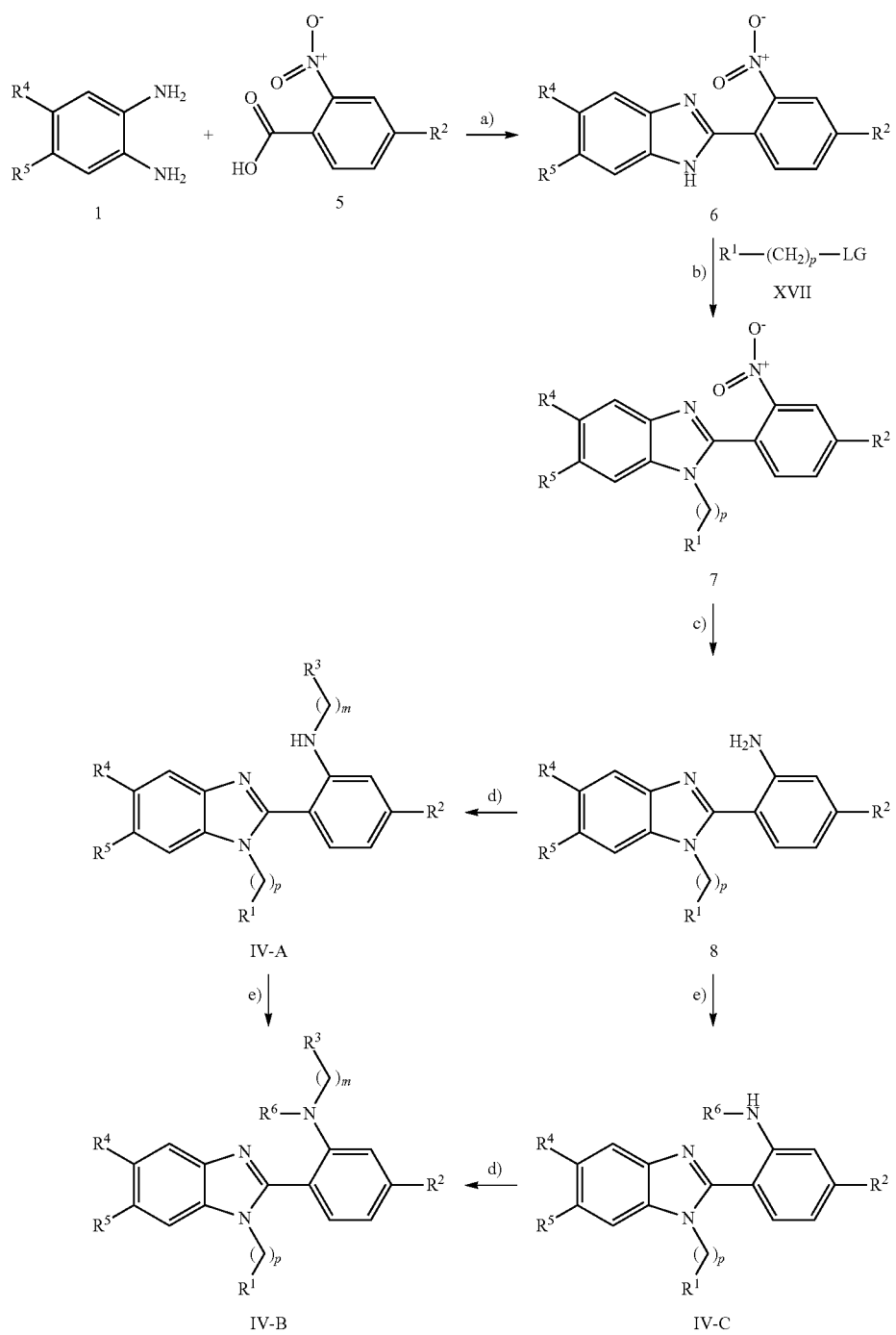

Benzimidazoles of the general structure 6 are either commercially available or accessible by methods known in the art and as described above (step a), e.g. by reaction of a phenylene diamines derivatives 1 with 2-nitro-benzoic acids derivatives 5. Compounds of general structure 6 can be alkylated with compounds of general formula XVII, wherein LG is as defined before, to give intermediates 7 applying the methods described before (step b).

Reduction of the nitro group in intermediates 7 to furnish intermediates 8 can be accomplished by methods described in literature and known to those skilled in the art such as catalytic hydrogenation using palladium on charcoal, platinum (IV) oxide or Raney nickel as catalyst in a solvent or a solvent mixture such as ethyl acetate or alcohols e.g. ethanol or using a reducing system such as tin dichloride in an acid e.g. hydrochloric acid (step c).

Compounds of formula IV-A can be synthesized for example by alkylation of intermediates 8 with compounds of formula $R^3$—$(CH_2)_m$—X or $R^3$—$(CH_2)_m$—OTf, wherein X is an halogen, e.g. chlorine or bromine, and —OTf means triflate, using a base such as N-ethyl morpholine, potassium carbonate, potassium tert-butoxide, sodium tert-butoxide or pyridine, in a solvent such as N,N-dimethylformamide or toluene, in the presence or not of a catalyst, e.g. bis(dibenzylideneacetone)palladium, copper(I) bromide, copper(I) iodide or copper, and in the presence or not of triphenylphosphine.

Compounds of formula IV-A can be also synthesized from intermediates 8 by reductive amination using an aldehyde or a ketone with a reducing agent such as sodium borohydride or sodium cyanoborohydride in a solvent such as methanol or ethanol.

Compounds of formula IV-A can be further converted into compounds of formula IV-B, wherein $R^6$ is alkyl by alkylation with compounds of formula $R^6$-LG, wherein LG is as defined before, or through reductive amination using an aldehyde of formula $R^6$—CHO or a ketone of formula $R^6$—C(O)-alkyl and a reducing agent such as sodium cyanoborohydride or sodium triacetoxyborohydride, in the presence or not of acetic acid and in a solvent such as 2-dichloroethane or tetrahydrofuran (step e).

Alternatively, compounds of formula IV-B, wherein $R^6$ is alkyl are accessible from compounds of formula IV-C (step d) which in turn can be alkylated from intermediates 8 (step e) applying the methods outlined before.

Compounds of the general formula V-A to V-C can be prepared according to Scheme 3.

art) in a solvent such as dichloromethane in the presence of a base such as Hünig's base (step a).

Alternatively, compounds of formula V-A can be synthesized via amide coupling of intermediates 8 with compounds of formula $R^3$—$(CH_2)_m$—COOH (either commercially available or accessible by methods described in the literature or by methods known in the art) in the presence of a coupling reagent such as N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a solvent e.g. N,N-dimethylformamide (DMF) or dioxane, in the presence or not of a base such as triethylamine, diisopropylethylamine or 4-(dimethylamino)pyridine (step a).

Compounds of formula V-A can be also synthesized by reacting intermediates 8 with compounds of formula $R^3$—$(CH_2)_m$—COOalkyl, wherein alkyl is e.g. methyl, and using a base such as lithium hexamethyldisilazane in a solvent such as tetrahydrofuran (step a).

Compounds of formula V-A can be further converted into compounds of formula V-B, wherein $R^7$ is alkyl by alkylation with compounds of formula $R^7$-LG, wherein LG is as defined before, or through reductive amination using an aldehyde of formula $R^7$—CHO or a ketone of formula $R^7$—C(O)-alkyl and a reducing agent such as sodium cyanoborohydride or sodium triacetoxyborohydride, in the presence or not of acetic acid and in a solvent such as 2-dichloroethane or tetrahydrofuran (step b).

Scheme 3

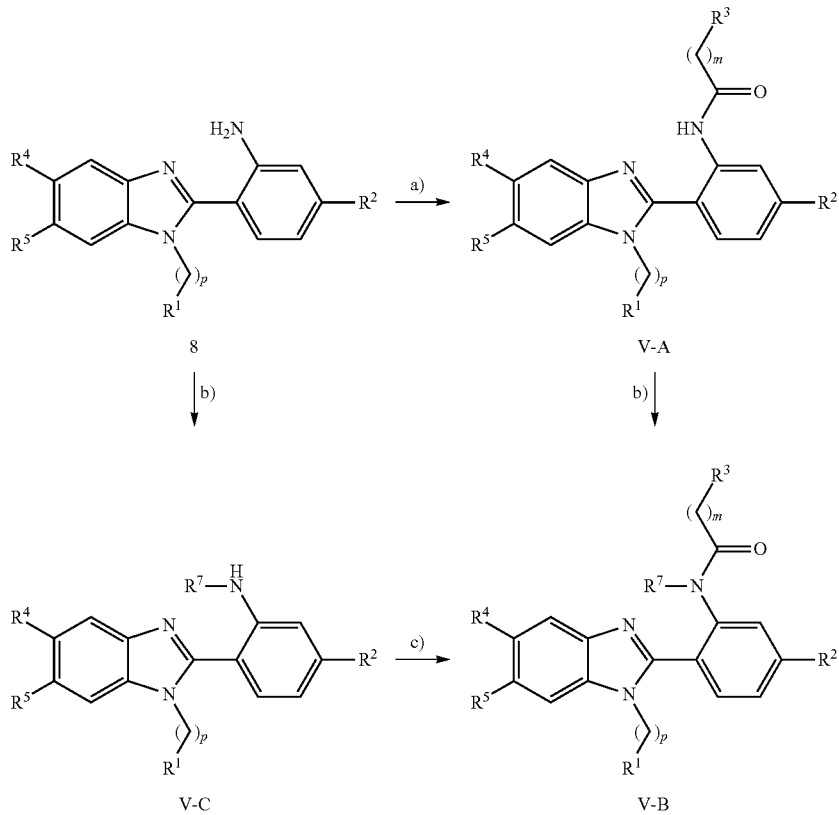

Compounds of formula V-A can be prepared by reaction of intermediates 8 with compounds of formula $R^3$—$(CH_2)_m$—C(O)—Cl (either commercially available or accessible by methods described in references or by methods known in the Alternatively, compounds of formula V-B, wherein $R^7$ is alkyl are accessible from compounds of formula V-C (step c) which in turn can be alkylated from intermediates 8 (step b) applying the methods outlined before.

Compounds of formula VI-A to VI-C can be prepared according to Scheme 4.

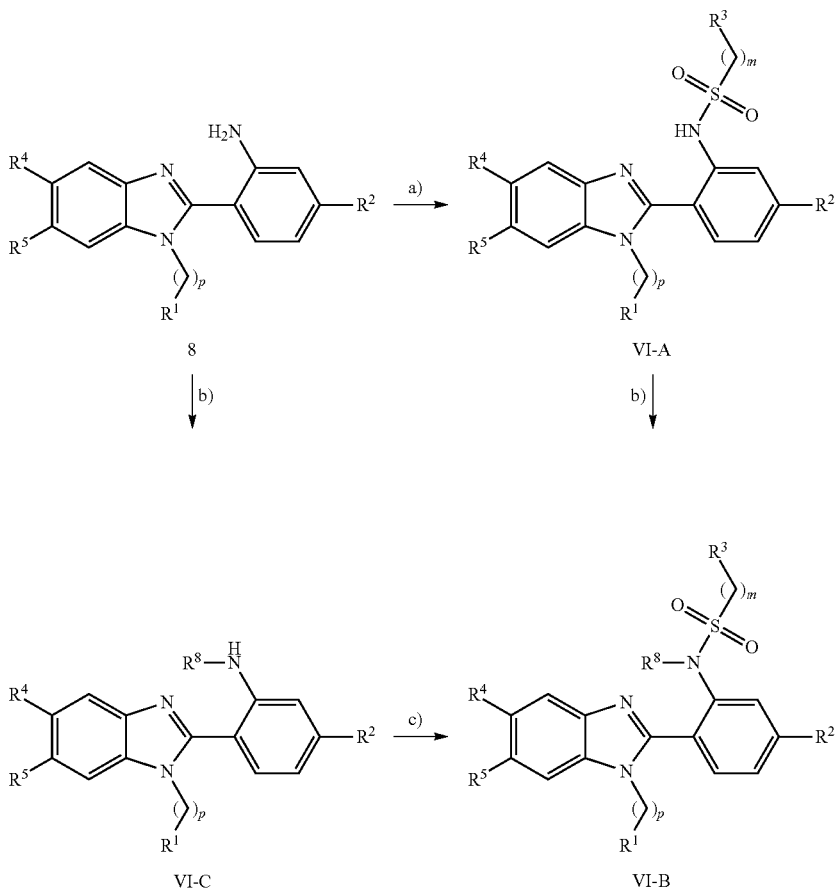

Compounds of formula VI-A can be prepared by reaction of intermediates 8 with compounds of formula R³—(CH₂)_m—S(O)₂—Cl (either commercially available or accessible by methods described in references or by methods known in the art) in a solvent such as dichloromethane in the presence of a base such as Hünig's base (step a).

Compounds of formula VI-A can be further converted into compounds of formula VI-B, wherein $R^8$ is alkyl by alkylation with compounds of formula $R^8$-LG, wherein LG is as defined before, or through reductive amination using an aldehyde of formula $R^8$—CHO or a ketone of formula $R^8$—C(O)-alkyl and a reducing agent such as sodium cyanoborohydride or sodium triacetoxyborohydride, in the presence or not of acetic acid and in a solvent such as 2-dichloroethane or tetrahydrofuran (step b).

Alternatively, compounds of formula VI-B, wherein $R^8$ is alkyl are accessible from compounds of formula VI-C (step c) which in turn can be alkylated from intermediates 8 (step b) applying the methods outlined before.

Compounds of formula VII-G and VII-H can be prepared as outlined in Scheme 5.

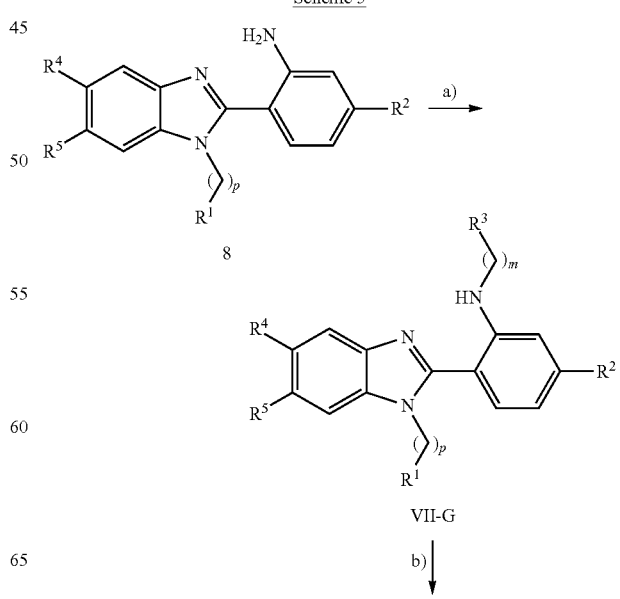

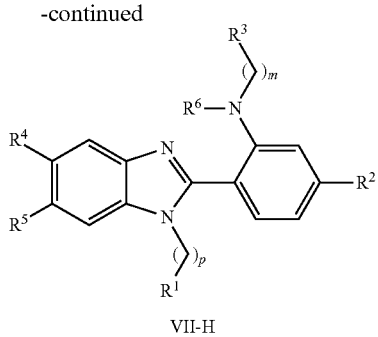

VII-H

Intermediates 8 can be converted to compounds of formula VII-G through alkylation with compounds of formula $R^3$—$(CH_2)_m$—X, wherein m is 1 or 2 and X is halogen, e.g. bromine or chlorine, in a solvent such as N,N-dimethylformamide and using a base such as cesium carbonate or sodium hydride (step a).

Alternatively, compounds of formula VII-G, wherein m is 1 or 2 can be synthesized from intermediates 8 via reductive amination using aldehydes or ketones using the methods described above. Furthermore, compounds of formula VII-G, wherein m is 1 or 2 can be synthesized from intermediates 8 by reaction with methyl or ethyl iodo- or bromo-benzoates, (R)-2,2'-bis(diphenylphosphino)-1,1'-binaphthyl, tris(dibenzylideneacetone)dipalladium and using a base such as sodium tert-butoxide and in a solvent such as toluene.

Compounds of formula VII-G can be transformed into compounds of formula VII-H, wherein $R^6$ is alkyl by alkylation or reductive amination as described before (step b).

Compounds of formula VII-G, wherein m is zero can be prepared from intermediates 8 by methods described in literature, for example using phenylboronic acids derivatives, copper(II) oxide and a base such as 1,8-diazabicyclo[5.4.0]undec-7-ene in a solvent such as methanol or dimethyl sulfoxide.

Compounds of formula VIII-A to VIII-C can be synthesized according to Scheme 6.

Scheme 6

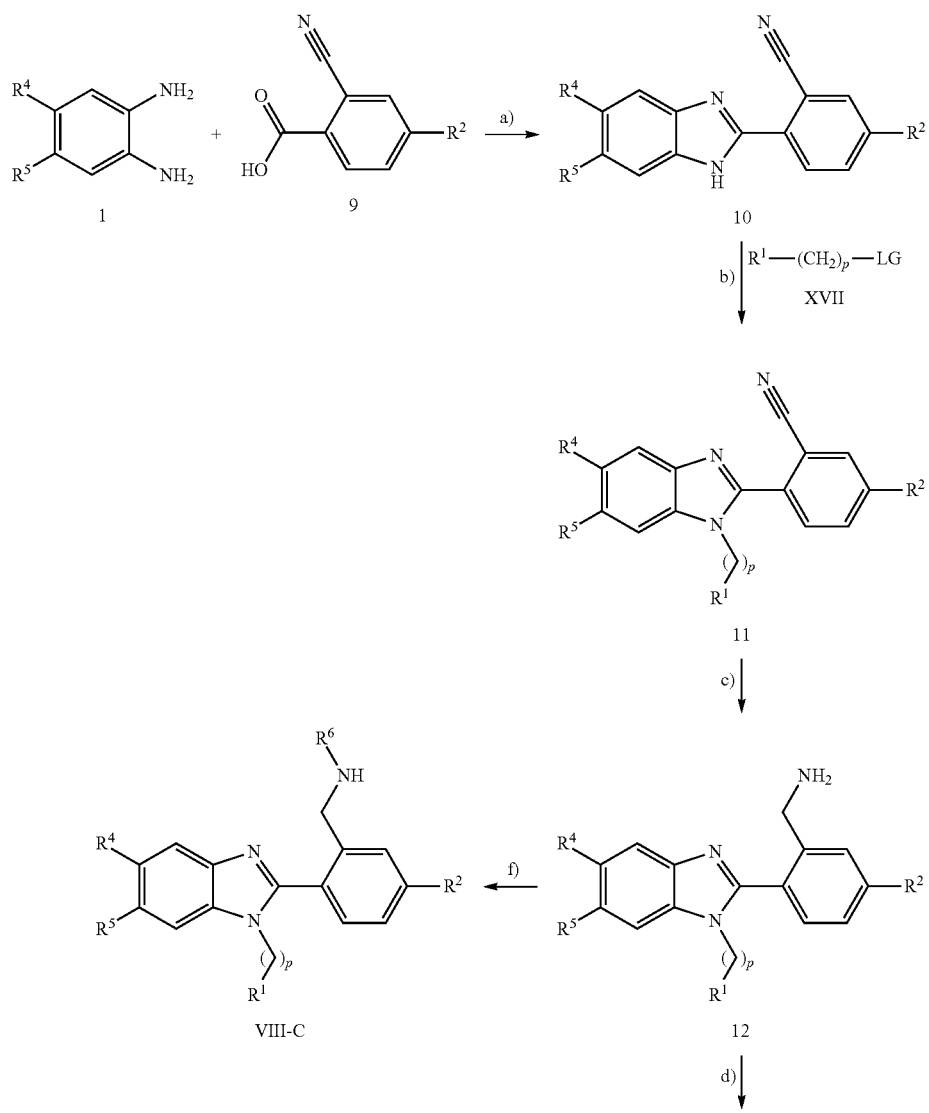

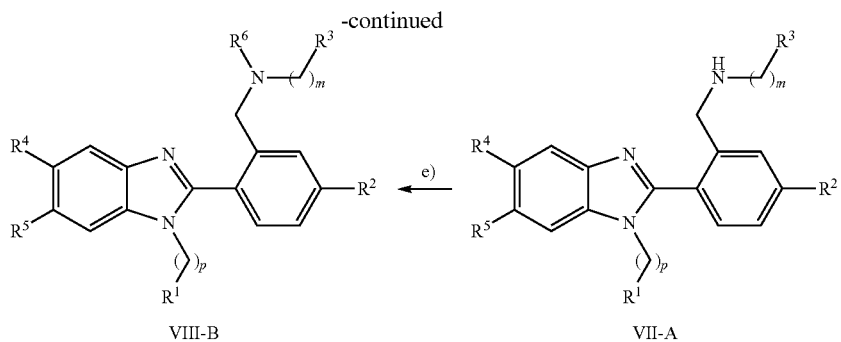

Benzimidazoles of the general structure 10 are either commercially available or accessible by methods known in the art and as described above (step a), e.g. by reaction of phenylene diamines derivatives 1 with 2-cyano-benzoic acids derivatives 9. Compounds of general structure 10 can be alkylated with compounds of formula XVII, wherein LG is as defined before, applying the methods described above to give intermediates 11 (step b).

Reduction of the cyano group in intermediates 11 by methods described in literature and known by those skilled in the art, for example by hydrogenation using a catalyst such as palladium or nickel in an appropriate solvent such as ethyl acetate, methanol, ethanol or mixtures of said solvents, or by treatment with lithium aluminium hydride in solvents such as diethyl ether, or by reduction with borane dimethyl sulfide complex in tetrahydrofuran, furnishes intermediates 12 (step c).

Compounds of formula VIII-A can be synthesized via alkylation or by reductive amination applying the conditions as described before (step d).

Compounds of formula VIII-A can be further converted into compounds of formula VIII-B, wherein $R^6$ is alkyl by alkylation or reductive amination reactions applying the methods described before (step e).

Compounds of formula VIII-C, wherein $R^6$ is alkyl can be synthesized from intermediates 12 by alkylation or reductive amination reactions using the conditions described before.

Compounds of formula VIII-A to and VIII-C can be also synthesized for example by treating compounds of formula XI-A to XI-C (Scheme 9) with a reducing agent such as lithium aluminium hydride, di-isobutylaluminium hydride or borane dimethyl sulfide or tetrahydrofuran complex in a solvent such as diethyl ether, tert-butyl methyl ether or tetrahydrofuran at temperatures between 0° C. and the boiling point of the solvent.

Compounds of formula IX-A to IX-C can be synthesized according to Scheme 7.

Scheme 7

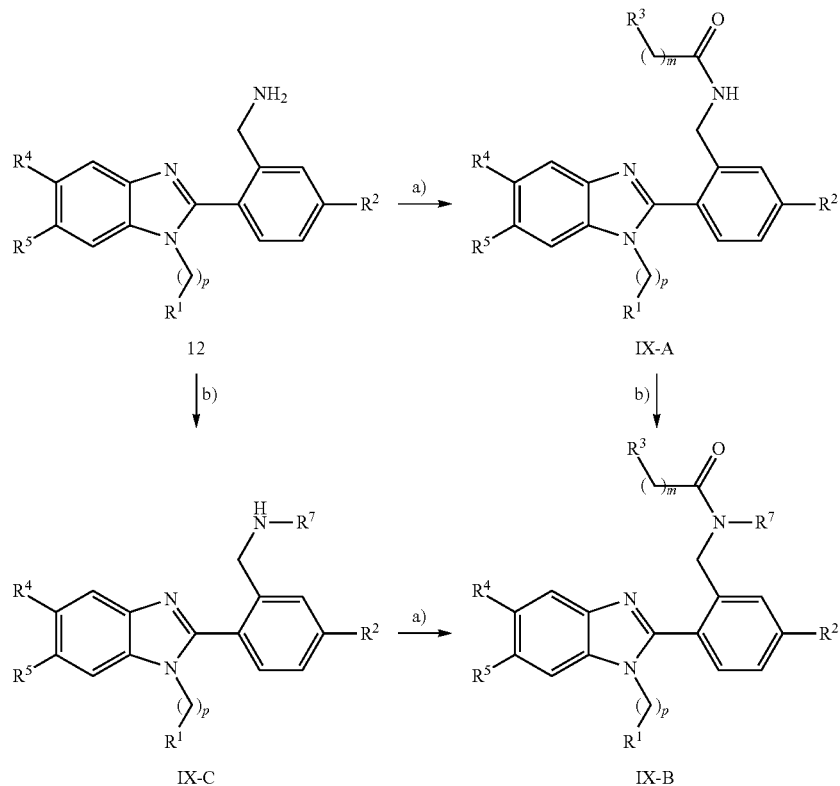

Compounds of formula IX-A can be synthesized by methods known by those skilled in the art or as described before (step a).

Compounds of formula IX-A can be further converted into compounds of formula IX-B, wherein $R^7$ is alkyl by alkylation or reductive amination reactions applying the methods described before (step b).

Compounds of formula IX-C, wherein $R^7$ is alkyl can be synthesized from intermediates 12 by alkylation or reductive amination reactions using the conditions described before (step b).

Compounds of formula IX-C, wherein $R^7$ is alkyl can be further converted into compounds of formula IX-B, wherein $R^7$ is alkyl by methods known by those skilled in the art or as described before (step a).

Compounds of formula X-A to X-C can be synthesized according to Scheme 8.

Compounds of formula X-A can be synthesized by methods known by those skilled in the art or as described before (step a).

Compounds of formula X-A can be further converted into compounds of formula X-B, wherein $R^8$ is alkyl by alkylation or reductive amination reactions applying the methods described before (step b).

Compounds of formula X-C, wherein $R^8$ is alkyl can be synthesized from intermediates 12 by alkylation or reductive amination reactions using the conditions described before (step b).

Compounds of formula X-C, wherein $R^7$ is alkyl can be further converted into compounds of formula X-B, wherein $R^8$ is alkyl by methods known by those skilled in the art or as described before (step a).

Compounds of formula XI-A to XI-C can be synthesized according to Scheme 9.

Scheme 8

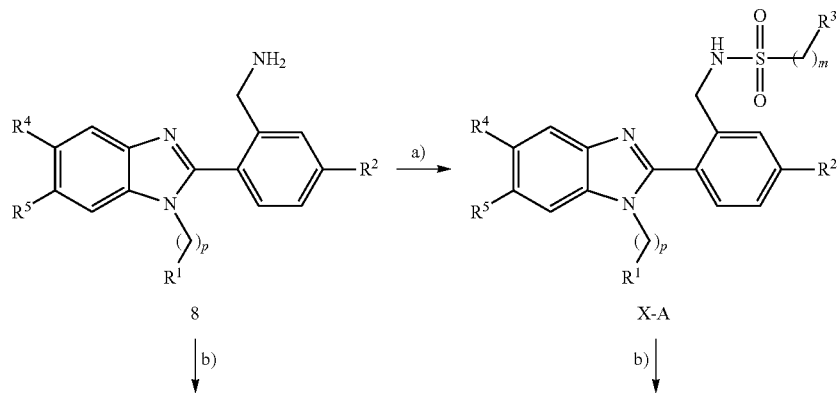

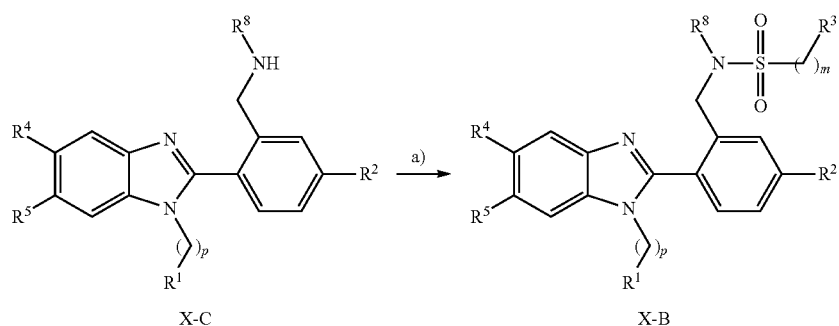

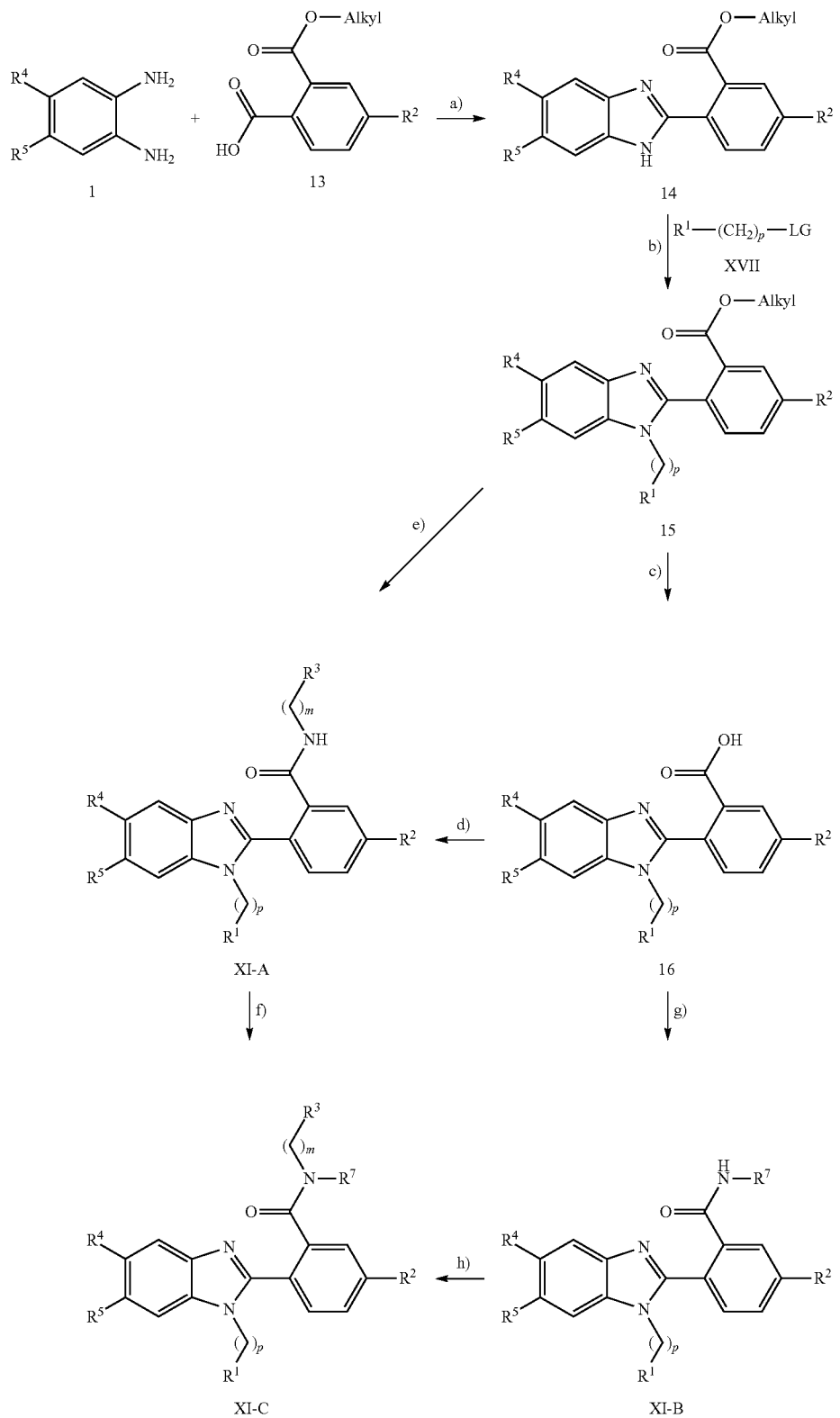
Alkyl is e.g. methyl or ethyl

Benzimidazoles of the general structure 14 are either commercially available or accessible by methods known in the art and as described above (step a), e.g. from phenylene diamines derivatives 1 and phthalic acid mono esters derivatives 13. Compounds of general structure 14 can be alkylated with compounds of formula XVII, wherein LG is as defined before, applying the methods described before to give intermediates 15 (step b).

Compounds of formula XI-A can be synthesized from intermediates 15 for example by cleaving the ester function by methods outlined before (step c) and coupling the resulting carboxylic acid intermediates 16 with amines of formula $R^3$—$(CH_2)_m$—$NH_2$ using methods described in literature, known to those skilled in the art or as described before (step d).

Alternatively compounds of formula XI-A can be obtained from intermediates 15 and amines of formula $R^3$—$(CH_2)_m$—$NH_2$ for example using an appropriate base such as lithium bis(trimethylsilyl)amide in a suitable solvent such as tetrahydrofuran (step e).

Alternatively, intermediates 15 can be reacted with amines of formula $R^3$—$(CH_2)_m$—$NH_2$ using trimethylaluminium in a suitable solvent such as toluene (step e). Intermediates 16 can be converted into compounds of formula XI-B via amide coupling with compounds of formula $R^7$—$NH_2$ (either commercially available or accessible by methods described in literature) under the conditions described before (step g).

Compounds of formula XI-B can be further converted into compounds of formula VI-C via reductive amination or alkylation applying the methods outlined above (step h).

Compounds of formula XI-A can be further converted into compounds of formula XI-C, wherein $R^7$ is alkyl via reductive amination or alkylation applying the methods outlined above (step f).

Compounds of formula XII-A can be prepared according to Scheme 10.

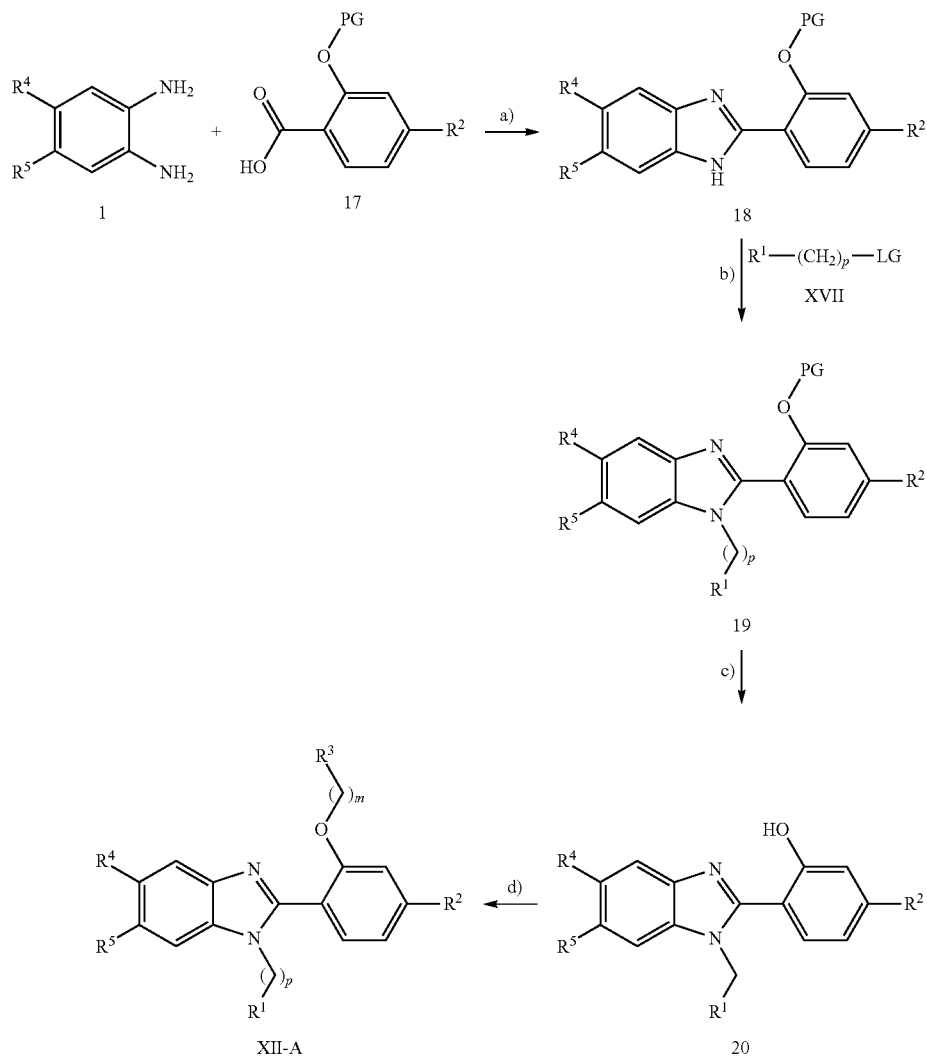

Scheme 10

PG = Protecting group, e.g. methyl, ethyl, tert-butyl or benzyl

Benzimidazoles of the general structure 18 are either commercially available or accessible by methods known in the art and as described above (step a), e.g. from phenylene diamines derivatives 1 and O-protected hydroxy-benzoic acids derivatives 17. Compounds of general structure 18 can be alkylated with compounds of formula XVII, wherein LG is as defined before, under the conditions described before to give intermediates 19 (step b).

The protecting group (PG) in intermediates 19 can be cleaved off by methods known to those skilled in the art e.g. in case PG is methyl then treatment of intermediates 19 with, e.g. boron tribromide in a solvent such as dichloromethane) furnishes intermediates 20 (step c).

Intermediates 20 can be converted into compounds of formula XII-A by e.g. alkylation with $R^3$—$(CH_2)_m$-LG, wherein m is 1 or 2 and LG is as defined before, using a base such as sodium hydride or cesium carbonate and in a solvent such as N,N-dimethylformamide or acetone (step d).

For compounds of formula XII-A, wherein m is zero, the formation of the ether bond can be accomplished by, e.g. Mitsunobu coupling of intermediate 20 and a compound of formula $R^3$—$(CH_2)_m$—OH (step d) using an activating system such as diethyl- or di-tert-butyl azodicarboxylate and triphenyl- or tributyl-phosphine in a solvent such as tetrahydrofuran according to methods known to the man skilled in the art and described in the literature.

Alternatively, compounds of formula VII-A, wherein m is zero can be obtained by either nucleophilic substitution or by nucleophilic aromatic substitution, for example by reacting compounds of formula $R^3$—X, wherein X is halogen, with intermediate 20 using a base such as sodium hydride in a solvent such as N,N-dimethylformamide (step d). Reactions of this type are known to those skilled in the art and are described in the literature.

Compounds of formula of formula XIII-A can be synthesized according to Scheme 11.

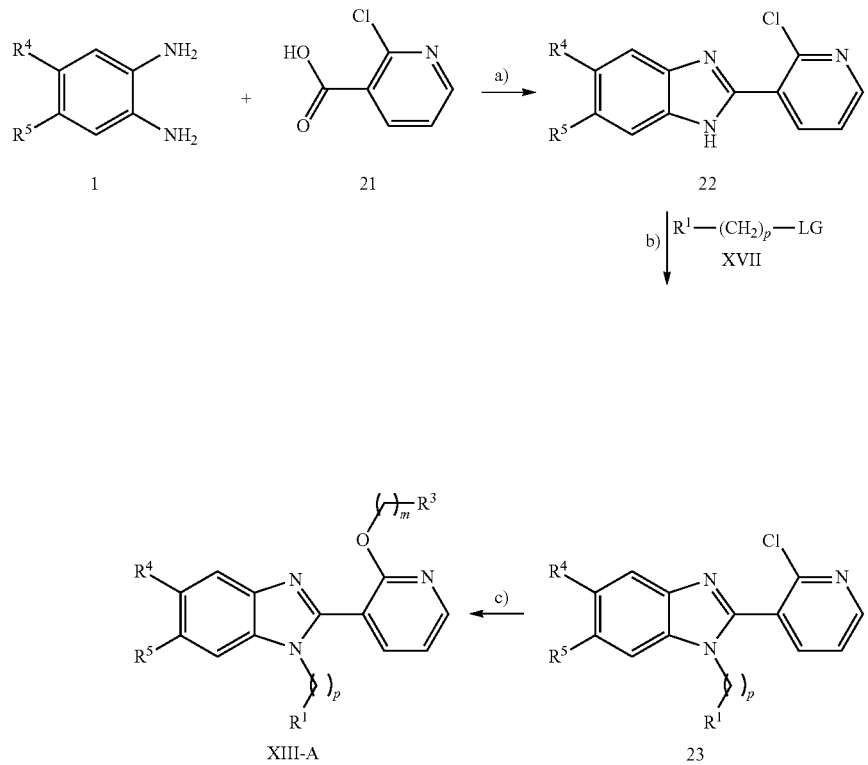

Scheme 11

Benzimidazoles of the general structure 22 are either commercially available or accessible by methods known in the art and as described above (step a), e.g. from phenylene diamines derivatives 1 and 2-chloro-pyridines derivatives 21. Compounds of general structure 22 can be alkylated with compounds of formula XVII, wherein LG is as defined before, under the conditions described before to give intermediates 23 (step b).

Compounds of formula XIII-A can be synthesized from intermediates 23 for example by nucleophilic substitution using compounds of formula $R^3$—$(CH_2)_m$—OH and a base such as sodium hydride or cesium carbonate in a solvent such as N,N-dimethylformamide or dimethylsulfoxide.

Compounds of formula XIV-A can be prepared according to Scheme 12.

Scheme 12

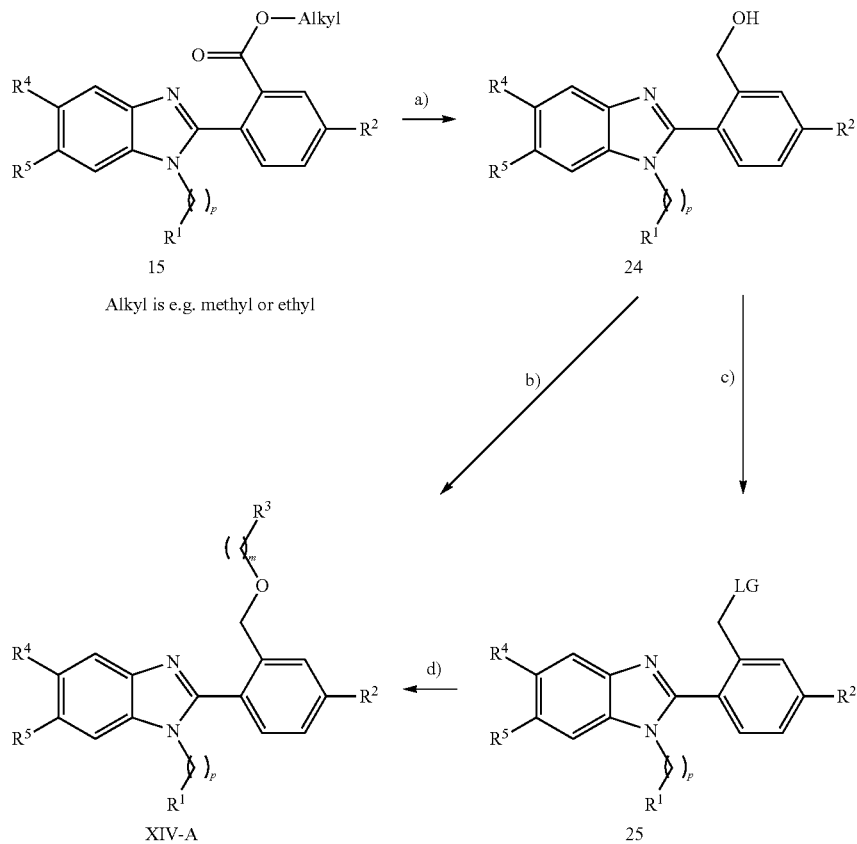

Alkyl is e.g. methyl or ethyl

The ester group in intermediates 15 (accessible as described in Scheme 9) can be converted to the primary alcohol to give intermediates 24 (step a) using a suitable reducing agent in a solvent such as lithium aluminum hydride or diisobutylaluminum hydride in diethyl ether or tetrahydrofuran, or sodium borohydride in methanol.

Compounds of formula XIV-A, wherein m is zero can be prepared from intermediates 24 and alcohols of the type $R^3$—OH using Mitsunobu couplings as described above (step b).

Compounds of formula XIV-A, wherein m is 1 or 2 can be synthesized from intermediates 24 and compounds of formula $R^3$—$(CH_2)_m$-LG, wherein LG is as defined before, and a base such as sodium hydride or cesium carbonate in a solvent such as N,N-dimethylformamide or dimethylsulfoxide (step b).

Alternatively, compounds of formula XIV-A can be also obtained by converting the alcohol group in intermediates 24 into a leaving group LG such as a halogen (e.g. bromine, chlorine or iodine) or a sulfonate group (e.g. mesylate, tosylate or triflate) to give intermediates 25 (step c). Subsequent reaction of intermediates 25 with alcohols of formula $R^3$—$(CH_2)_m$—OH using a base such as sodium hydride or cesium carbonate in a solvent such as N,N-dimethylformamide or acetone (step d).

Compounds of formula XV-A can be prepared according to Scheme 13.

Scheme 13

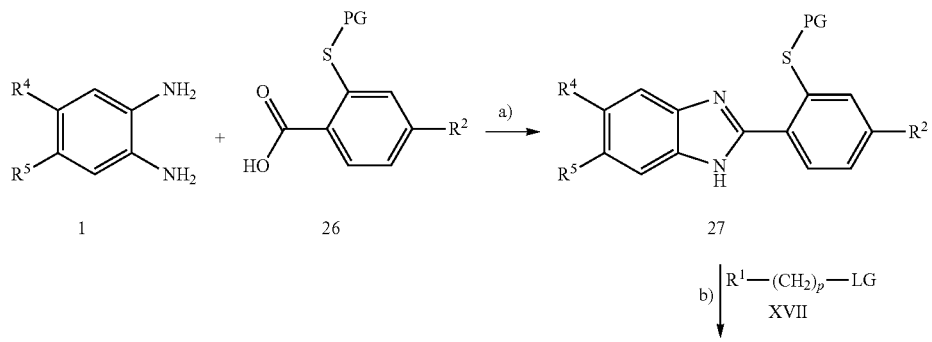

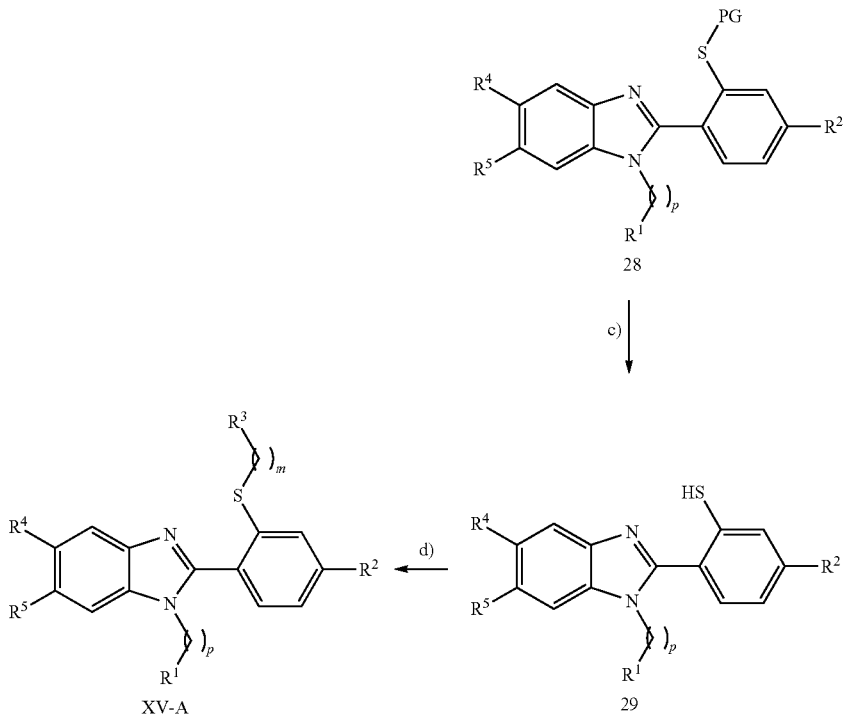

Benzimidazoles of the general structure 27 are either commercially available or accessible by methods known in the art and as described above (step a), e.g. from phenylene diamines derivatives 1 and S-protected 2-mercapto-benzoic acids derivatives 26, wherein PG is e.g. benzyl or tert-butoxycarbonyl thioester. Compounds of general structure 27 can be alkylated with compounds of formula XVII, wherein LG is as defined before, under the conditions described before to give intermediates 28 (step b).

Intermediates 29 are accessible via cleavage of the sulfur protecting group in intermediates 28 by methods known to those skilled in the art (step c).

Compounds of formula XV-A can be synthesized for example through alkylation of intermediates 29 with compounds of formula $R^3$—$(CH_2)_m$-LG under the conditions described before (step d), wherein LG is as defined before.

Compounds of formula X-A can be also synthesized from intermediates 29 for example via Mitsunobu reaction as described before.

Alternatively, compounds of formula XV-A, wherein m is zero can also be synthesized via nucleophilic aromatic substitution by reacting a compound of formula $R^3$—X, wherein X is halogen, with intermediates 29, using a base such as sodium hydride, sodium tert-butoxide, potassium tert-butoxide or potassium carbonate in a solvent such as N,N-dimethylformamide, ethanol, dimethylsulfoxide or N-methylpyrrolidine, with or without a catalyst such as copper(I) iodide or tetrakis(triphenyl)phosphine palladium(0) (step d).

Compounds of formula XVI-A can be prepared according to Scheme 14.

Scheme 14

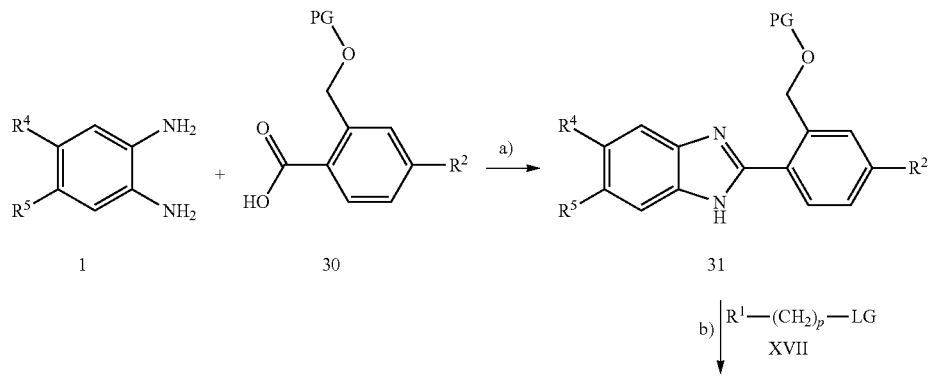

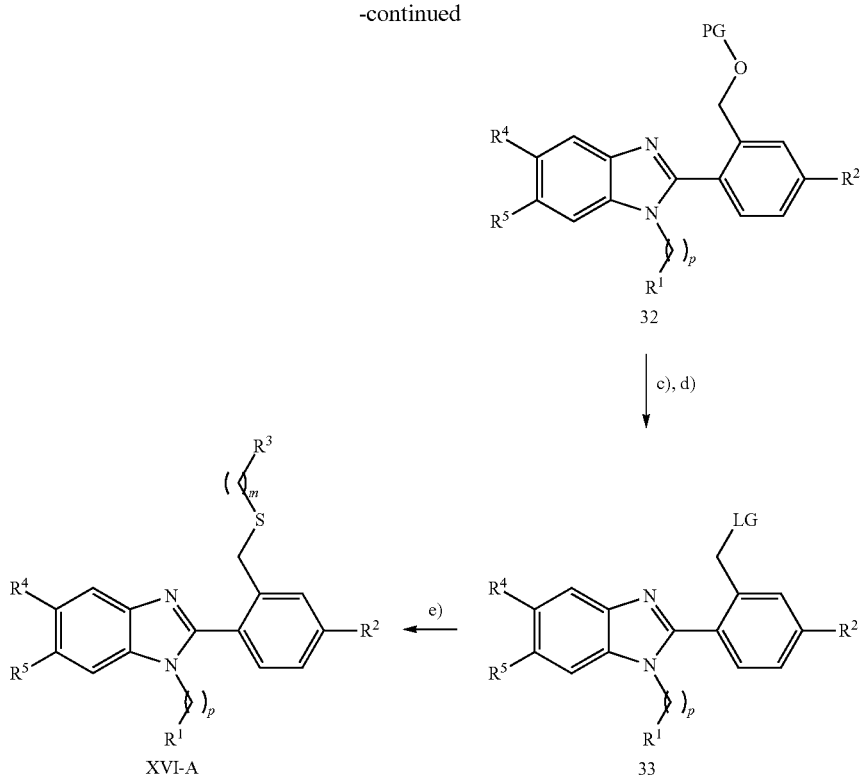

Benzimidazoles of the general structure 31 are either commercially available or accessible by methods known in the art and as described above (step a), e.g. from phenylene diamines derivatives 1 and 2-hydroxymethyl benzoic acids derivatives 30, wherein the protecting group (PG) is e.g. triisopropylsilyl or a 1,3-dioxane group.

Compounds of general structure 31 can be alkylated with compounds of formula XVII, wherein LG is as defined before, under the conditions described before to give intermediates 32 (step b).

Alternatively, intermediates 32 are also accessible via protection of the hydroxy group in intermediates 24 (as described in Scheme 12) by methods described in literature. Intermediates 32 can be converted into intermediates 33 by removal of the protecting group (PG) (e.g. in case PG is triisopropylsilyl then intermediates 32 are treated with, e.g. tetrabutylammonium fluoride in tetrahydrofuran to provide the free hydroxy function (step c)), and transforming the hydroxy group into a leaving group LG such as a halogen (e.g. bromine, chlorine or iodine) or a sulfonate group (e.g. mesylate, tosylate or triflate) using the conditions described before (step d).

Intermediates 33 can be reacted with compounds of formula $R^3$—$(CH_2)_m$—SH (either commercially available or accessible by methods know to those skilled in the art) to furnish compounds of formula XVI-A by using a base such as cesium or potassium carbonate and a suitable solvent such as N,N-dimethylformamide or acetone (step e).

Alternatively, compounds of formula XVI-A can be also obtained from the unprotected hydroxy derivative of intermediates 32 (step c) and compounds of formula $R^3$—$(CH_2)_m$—SH (either commercially available or accessible by methods know to those skilled in the art) applying Mitsunobu reaction conditions as described before.

Compounds of formula XVI-A can also be prepared according to Scheme 15.

Scheme 15

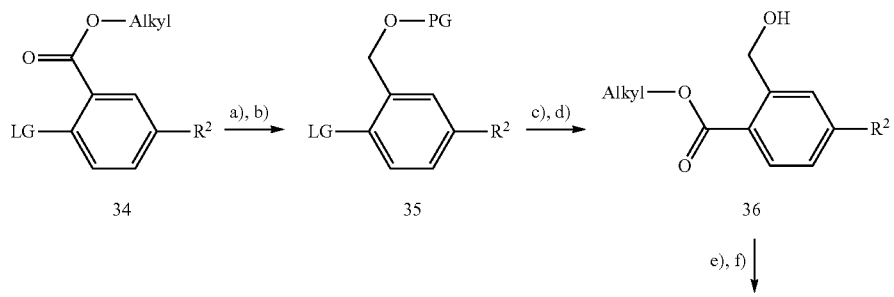

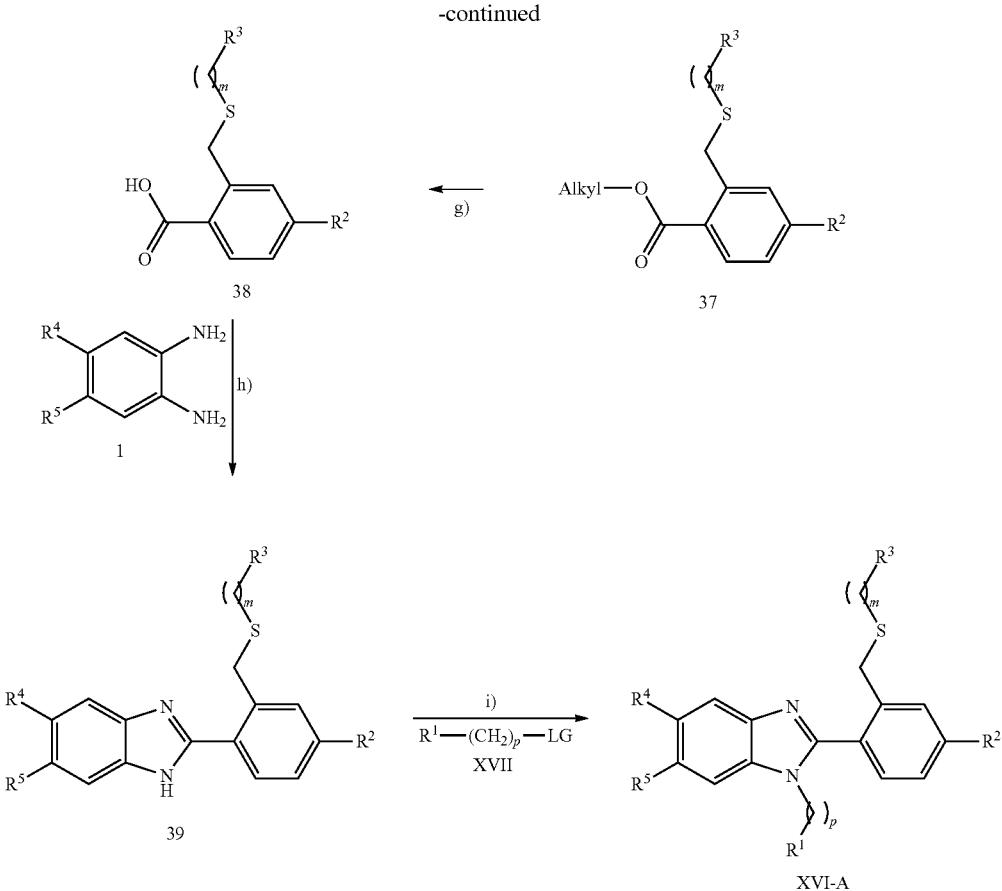

Intermediates 34 are either commercially available or synthesized by methods known to those skilled in the art. Compounds of general structure 34 can be converted into intermediates 35 by reduction of the ester group to the primary alcohol (step a) and protecting the primary alcohol group with a protecting group (PG) (e.g. tri-isopropylsilyl or benzyl) stable towards the subsequent reaction steps by methods described in literature (step b).

The leaving group LG such as a halogen (e.g. bromine, chlorine or iodine) or a sulfonate group (e.g. mesylate, tosylate or triflate) in intermediates 35 can be exchanged into an ester function (step c) by methods known to those skilled in the art such as carbonylation reaction using carbon monoxide, a transition metal catalyst such as bis(triphenylphosphine)palladium(II) dichloride or palladium(II) acetate with triphenylphosphine, a base such as triethylamine and an alcohol such as methanol (to yield the methyl ester), optionally in a solvent such as toluene or N,N-dimethylformamide.

Alternatively, the ester formation can be accomplished by metal-halogen exchange (e.g. using n- or tert-butyl lithium in an appropriate solvent or solvent mixture such as tetrahydrofuran, diethyl ether or n-hexane) and quenching the so-formed lithium species with e.g. methyl chloroformate (step c).

The protecting group (PG) in intermediates 35 can then be removed by methods known in the art to furnish intermediates 36 (step d). Intermediates 36 can be converted to intermediates 37 for example by transforming the alcohol function into a leaving group LG such as a halogen (e.g. bromine, chlorine or iodine) or a sulfonate group (e.g. mesylate, tosylate or triflate) (step e) according to methods known in the literature or as described before and subsequently reacting the newly formed intermediates with compounds of formula $R^3$—$(CH_2)_m$—SH (either commercially available or accessible by methods described in literature) by using a suitable base and solvent such as cesium or potassium carbonate in N,N-dimethylformamide or acetone (step f).

Alternatively, intermediates 37 can be obtained from intermediates 36 and compounds of formula $R^3$—$(CH_2)_m$—SH applying Mitsunobu reaction conditions as described before. The ester function in intermediates 37 can be cleaved (step g) by methods known in the art and to give intermediates 38 that are condensed for example with phenylene diamines 1 to furnish intermediates 39.

Alkylation of intermediates 39 with compounds of formula XVII, wherein LG is as defined before, using the conditions described before furnishes compounds of formula XI-A (step i).

Compounds of the general formula (I) can also be synthesized according to Scheme 16.

Scheme 16

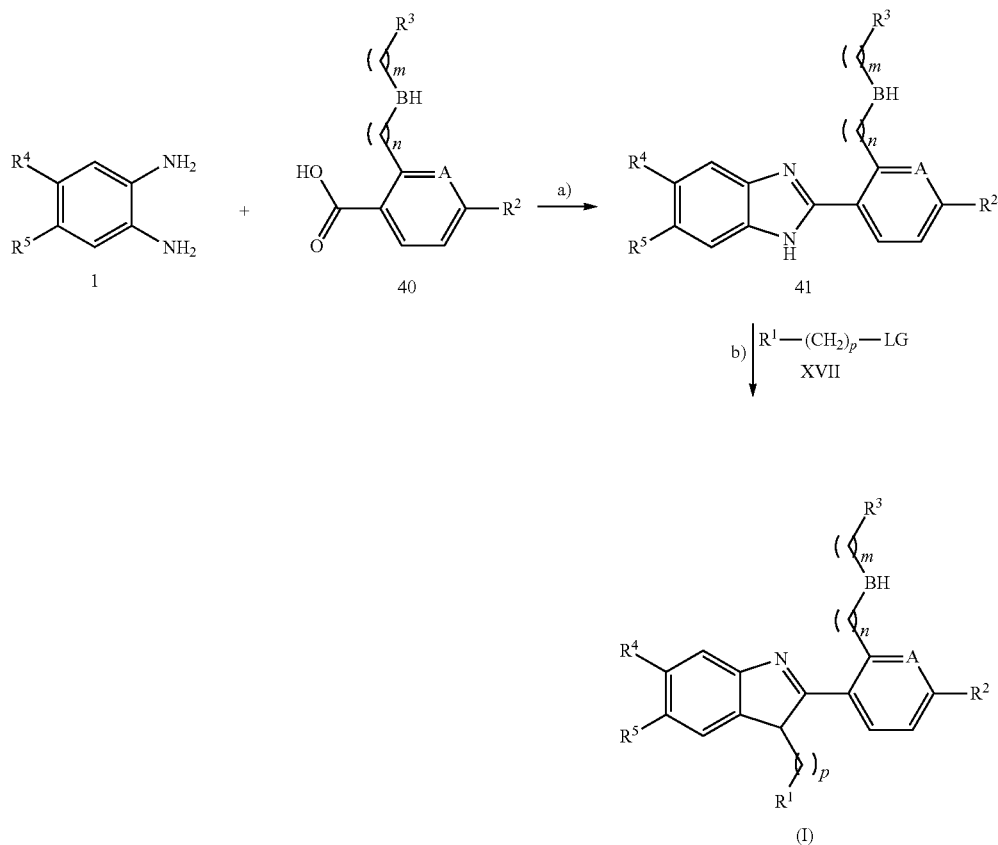

Condensation of phenylene diamines derivatives 1 with phenyl- or pyridyl-carboxylic acids derivatives 40 (either commercially available or synthesized by methods described before) provides benzimidazoles 41 (step a) which can be alkylated with compounds of formula XVII, wherein LG is as defined before, under the conditions described before (step b).

Compounds of the general formula (I), wherein $R^1$ or $R^3$ carries a carboxylic acid function can be synthesized according to Scheme 17.

Scheme 17

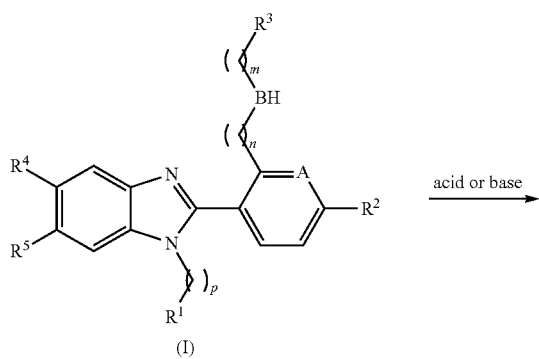

-continued

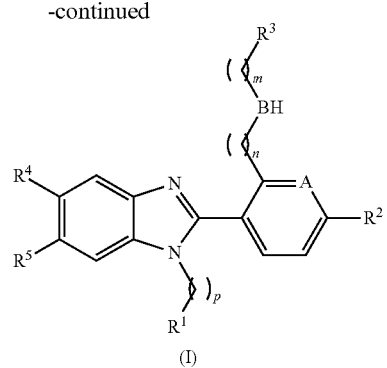

Compounds of formula (I), wherein $R^1$ or $R^3$ carries a carboxylic esters function (e.g. methyl, ethyl or tert-butyl esters) can be hydrolyzed under basic conditions with e.g. lithium hydroxide or sodium hydroxide in solvents such as methanol, water or tetrahydrofuran or mixtures of said solvents or under acidic conditions with e.g. hydrochloric acid or formic acid in a solvent such as alcohols (e.g. isopropanol) or tetrahydrofuran. Alternatively, compounds of the general formula (I), wherein $R^1$ or $R^3$ carries a carboxylic acid function can be synthesized from compound of formula (I) wherein $R^1$ or $R^3$ carries a cyano group by hydrolyzing the cyano function to the carboxylic acid under basic conditions with e.g. aqueous sodium hydroxide or aqueous lithium hydroxide, or under acidic conditions with e.g. hydrochloric or sulphuric acid in water.

Compounds of the general formula (I), wherein $R^1$ or $R^3$ carries a tetrazolyl group can be synthesized according to Scheme 18.

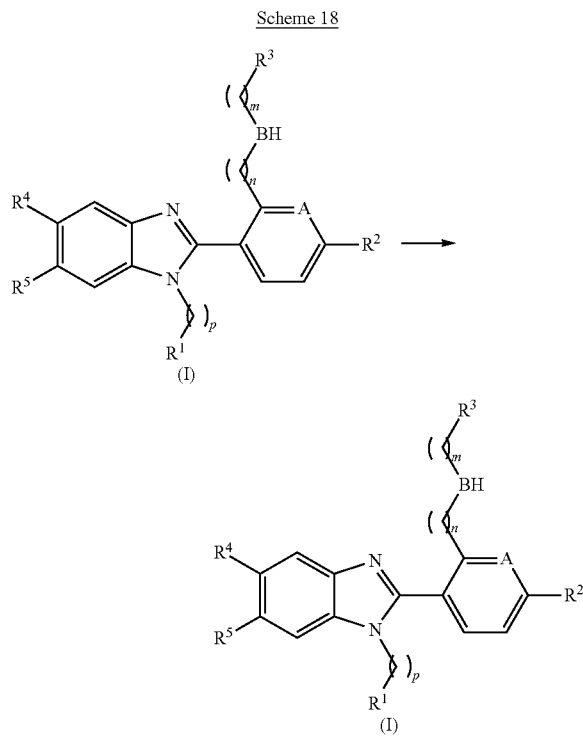

Scheme 18

Compounds of formula (I), wherein $R^1$ or $R^3$ carries a cyano group can be converted to compounds of formula (I), wherein $R^1$ or $R^3$ carries a tetrazolyl group using standard procedures such as reaction with sodium azide in the presence of a Lewis acid or ammonium chloride in water or organic solvents like dichloromethane or N,N-dimethylformamide.

Preferred is a process to prepare a compound according to formula (I) as described before

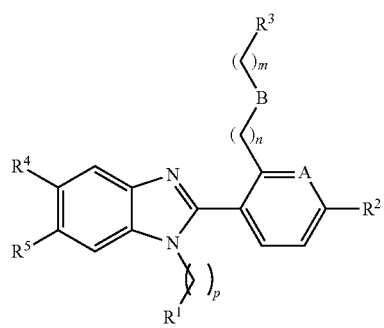

comprising
a) reaction of a compound of formula (XVIII) in the presence of a compound of formula (XIX);

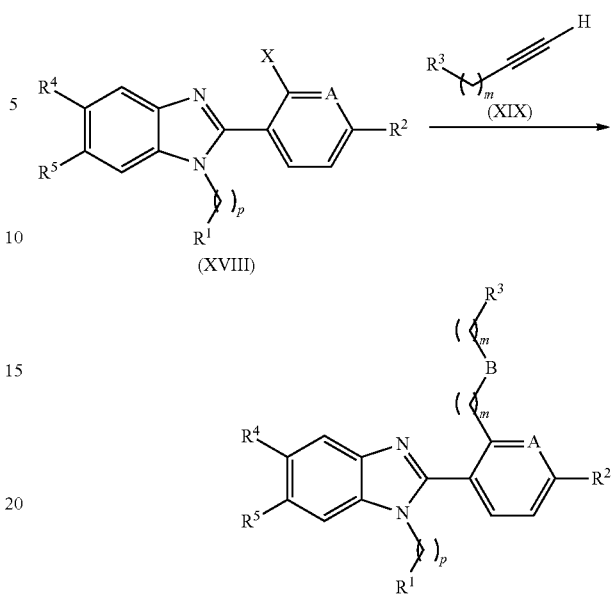

Preferred reaction is a Sonogashira-type coupling. Preferably in the presence of a base, particularly triethylamine, a catalyst system, particularly bis(triphenylphosphine)palladium(II) chloride and copper(I) iodide, in a solvent, particularly tetrahydrofuran, and at a temperature between RT and reflux of solvent, particularly at reflux of solvent, wherein $R^1$, $R^2$, $R^3$, $R^4$, $R^5$, m and p are defined as before, A is carbon, B is —C≡C—, n is zero and X is halogen, particularly bromine;

b) reaction of a compound of formula (XX) in the presence of dihydrogen;

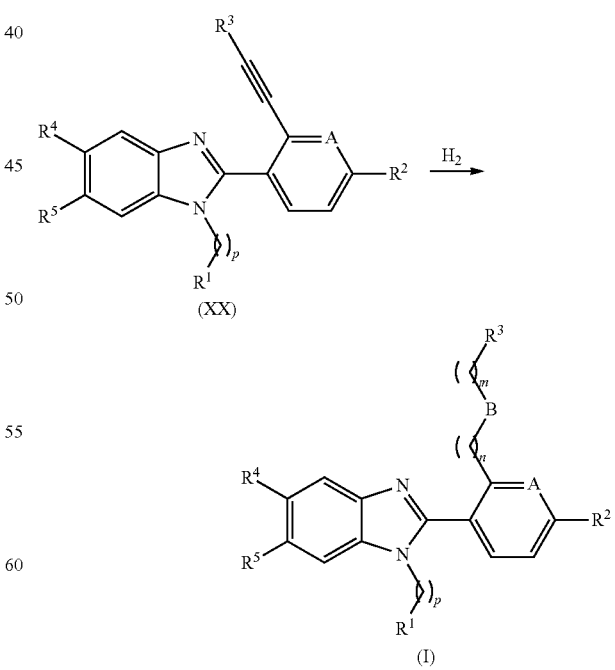

Preferably in the presence of a catalyst, particularly palladium on charcoal, in a solvent, particularly ethyl acetate, alcohols, particularly methanol, ethanol or a mixture of above mentioned solvents, at a temperature between −10° C. and reflux of solvent, particularly at RT, wherein $R^1$, $R^2$, $R^3$, $R^4$, $R^5$ and p are defined as before, A is carbon, B is —$CR^9R^{10}$—, $R^9$ is hydrogen, $R^{10}$ is hydrogen and the sum of m and n is 1;

c) reaction of a compound of formula (XXI) in the presence of a compound of formula (XXII);

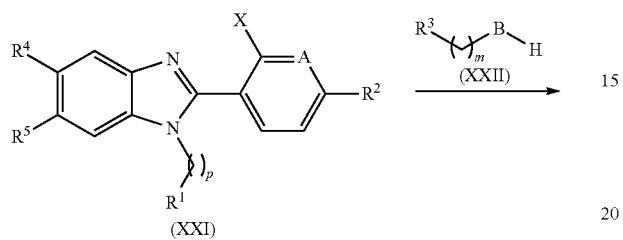

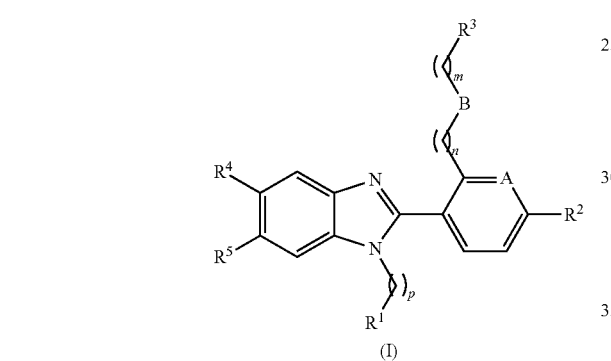

Preferably in the presence of a base, particularly sodium hydride or cesium carbonate, in a solvent, particularly N,N-dimethylformamide or dimethylsulfoxide, and at a temperature comprised between −10° C. and reflux of solvent, particularly at RT, wherein $R^1$, $R^2$, $R^3$, $R^4$, $R^5$, m and p are defined as before, A is nitrogen, B is —O—, n is zero and X is halogen, particularly chlorine;

d) reaction of a compound of formula (XXIII) in the presence of a compound of formula (XXII);

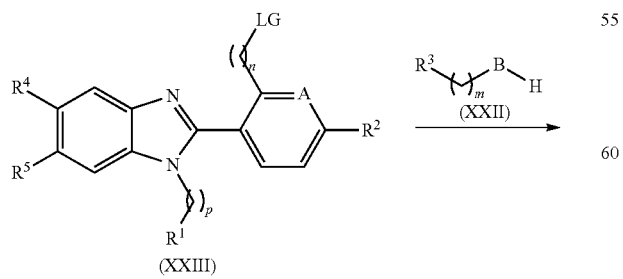

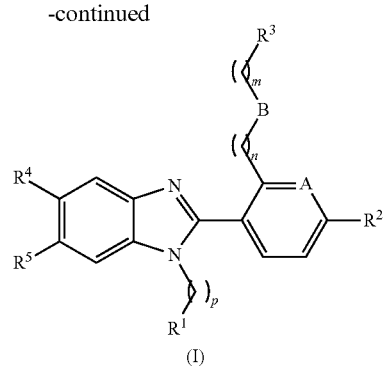

Preferably in the presence of a base, particularly sodium hydride or cesium carbonate, in a solvent, particularly N,N-dimethylformamide, acetone or dimethylsulfoxide, and at a temperature comprised between −10° C. and reflux of solvent, particularly at RT, wherein $R^1$, $R^2$, $R^3$, $R^4$, $R^5$, m and p are defined as before, LG is leaving group, a preferred leaving group is a halogen, particularly chlorine, A is carbon, B is —O— or —S— and n is 1 or 2;

e) reaction of a compound of formula (XXIV) in the presence of a compound of formula (XXV);

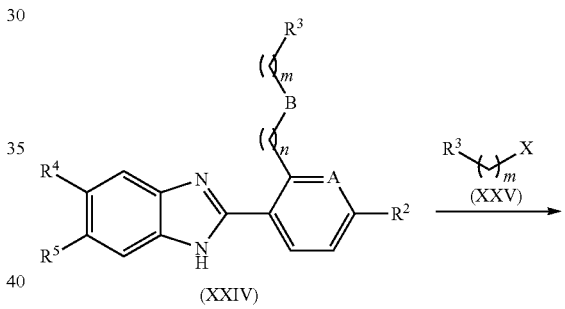

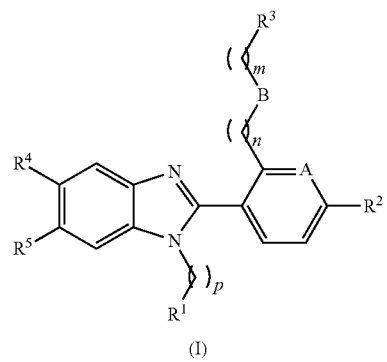

Preferably in the presence of a base, particularly sodium hydride or cesium carbonate, in a solvent, particularly N,N-dimethylformamide or acetone, and at a temperature comprised between −10° C. and reflux of solvent, particularly at RT, wherein A, B, $R^1$, $R^2$, $R^3$, $R^4$, $R^5$, m, n and p are defined as before and X is halogen, particularly chlorine;

f) reaction of a compound of formula (XXVI) in the presence of a compound of formula (XXV);

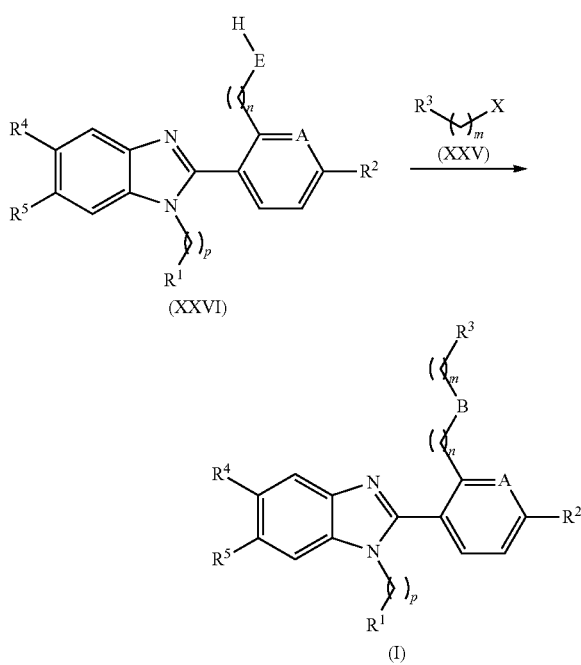

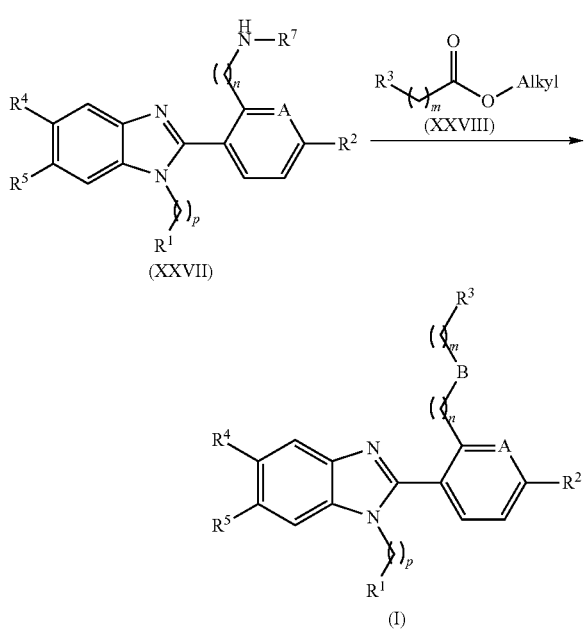

Preferably in the presence of a base, particularly sodium hydride or cesium carbonate, in a solvent, particularly N,N-dimethylformamide or acetone, and at a temperature comprised between −10° C. and reflux of solvent, particularly between RT and 60° C., wherein A, $R^1$, $R^2$, $R^3$, $R^4$, $R^5$, m, n and p are defined as before, X is halogen, particularly chlorine, E is —O—, —S—, —$NR^6$— or —C(O)$NR^7$— and B is —O—, —S—, —$NR^6$— or C(O)$NR^7$—; or g) reaction of a compound of formula (XXVII) in the presence of a compound of formula (XXVIII);

Preferably in the presence of a base, particularly lithium bis(trimethylsilyl)amide, in a solvent, particularly tetrahydrofuran, and at a temperature comprised between −70° C. and reflux of solvent, particularly between −30° C. and RT; wherein preferred alkyl are methyl or ethyl, A, $R^1$, $R^2$, $R^3$, $R^4$, $R^5$, m, n and p are defined as before and B is —C(O)$NR^7$—.

Preferred intermediates are selected from:

5-Chloro-2-(1-cyclohexylmethyl-5,6-difluoro-1H-benzoimidazol-2-yl)-phenol;
2-(4-Chloro-2-methoxy-phenyl)-5,6-difluoro-1H-benzoimidazole;
4-[5-Chloro-2-(1-cyclohexylmethyl-5,6-difluoro-1H-benzoimidazol-2-yl)-phenoxymethyl]-benzoic acid methyl ester;
{4-[5-Chloro-2-(1-cyclohexylmethyl-5,6-difluoro-1H-benzoimidazol-2-yl)-phenoxymethyl]-phenoxy}-acetic acid methyl ester;
4-[5-Chloro-2-(1-cyclohexylmethyl-5,6-difluoro-1H-benzoimidazol-2-yl)-phenoxymethyl]-benzonitrile;
4-[5-Chloro-2-(1-cyclohexylmethyl-5,6-difluoro-1H-benzoimidazol-2-yl)-phenoxymethyl]-3-fluoro-benzonitrile;
4-[5-Chloro-2-(1-cyclohexylmethyl-5,6-difluoro-1H-benzoimidazol-2-yl)-phenoxymethyl]-2-fluoro-benzonitrile;
4-[2-(1-Cyclohexylmethyl-5,6-difluoro-1H-benzoimidazol-2-yl)-benzyloxy]-3-fluoro-benzonitrile;
4-[2-(5,6-Difluoro-1H-benzoimidazol-2-yl)-benzyloxy]-3-fluoro-benzonitrile;
2-(4-Cyano-2-fluoro-phenoxymethyl)-benzoic acid;
2-(4-Cyano-2-fluoro-phenoxymethyl)-benzoic acid methyl ester;
4-{5-Chloro-2-[1-(2-cyclohexyl-ethyl)-5,6-difluoro-1H-benzoimidazol-2-yl]-phenoxymethyl}-3-fluoro-benzonitrile;
5-Chloro-2-[1-(2-cyclohexyl-ethyl)-5,6-difluoro-1H-benzoimidazol-2-yl]-phenol;
2-(4-Chloro-2-methoxy-phenyl)-1-(2-cyclohexyl-ethyl)-5,6-difluoro-1H-benzoimidazole;
4-{5-Chloro-2-[1-(2,2-dimethyl-propyl)-5,6-difluoro-1H-benzoimidazol-2-yl]-phenoxymethyl}-3-fluoro-benzonitrile;
5-Chloro-2-[1-(2,2-dimethyl-propyl)-5,6-difluoro-1H-benzoimidazol-2-yl]-phenol;
2-(4-Chloro-2-methoxy-phenyl)-1-(2,2-dimethyl-propyl)-5,6-difluoro-1H-benzoimidazole;
4-[2-(4-Chloro-2-cyclopentylmethoxy-phenyl)-5,6-difluoro-benzoimidazol-1-ylmethyl]-2-fluoro-benzonitrile;
4-[2-(4-Chloro-2-hydroxy-phenyl)-5,6-difluoro-benzoimidazol-1-ylmethyl]-2-fluoro-benzonitrile;
4-[2-(4-Chloro-2-methoxy-phenyl)-5,6-difluoro-benzoimidazol-1-ylmethyl]-2-fluoro-benzonitrile;
4-{2-[5-Chloro-2-(1-cyclohexylmethyl-5,6-difluoro-1H-benzoimidazol-2-yl)-phenyl]-ethyl}-benzonitrile;
4-[5-Chloro-2-(1-cyclohexylmethyl-5,6-difluoro-1H-benzoimidazol-2-yl)-phenylethynyl]-benzonitrile;
2-(2-Bromo-4-chloro-phenyl)-1-cyclohexylmethyl-5,6-difluoro-1H-benzoimidazole;
2-(2-Bromo-4-chloro-phenyl)-5,6-difluoro-1H-benzoimidazole;
5-Chloro-2-(1-cyclohexylmethyl-5,6-difluoro-1H-benzoimidazol-2-yl)-phenylamine;
2-(4-Chloro-2-nitro-phenyl)-1-cyclohexylmethyl-5,6-difluoro-1H-benzoimidazole;
2-(4-Chloro-2-nitro-phenyl)-5,6-difluoro-1H-benzoimidazole;
2-Fluoro-4-(1H-tetrazol-5-yl)-benzoic acid methyl ester;
2-Fluoro-4-(1H-tetrazol-5-yl)-benzoic acid;
3-Fluoro-4-(1H-tetrazol-5-yl)-benzoic acid methyl ester;
3-Fluoro-4-(1H-tetrazol-5-yl)-benzoic acid; and
2-(5,6-Difluoro-1H-benzoimidazol-2-yl)-benzoic acid methyl ester.

Compounds according to formula (I) as described above for use as therapeutically active substance are a further object of the invention.

Likewise an object of the present invention is a pharmaceutical composition comprising a compound according to formula (I) and a therapeutically inert carrier.

Also an object of the present invention are compounds according to formula (I) as described above for the preparation of a medicament for the treatment or prophylaxis of illnesses which are caused by disorders associated e.g. with the farnesoid X receptor.

Further preferred are compounds according to formula (I) as described above for the preparation of a medicament for the treatment or prophylaxis of atherosclerosis, metabolic syndrome, diabetes, diabetic nephropathy, obesity, dyslipidemia, particularly high LDL-cholesterol, high triglycerides and low HDL-cholesterol, diseases of cholesterol absorption, cholesterol gallstone disease, coronary heart disease, peripheral artery disease, stroke, cholestasis and fibrosis of the liver, non-alcoholic steatohepatitis, non-alcoholic fatty liver disease.

Also further preferred are compounds according to formula (I) as described above for the preparation of a medicament for the treatment or prophylaxis of psoriasis, cancer, particularly gastrointestinal cancer, osteoporosis, Parkinson's disease or Alzheimer's disease.

Particularly preferred are compounds of the formula (I) as described above for the preparation of a medicament for the treatment or prophylaxis of atherosclerosis, diabetes, non-alcoholic steatohepatitis or diabetic nephropathy.

More preferred are compounds of the formula (I) as described above for the preparation of a medicament for the treatment or prophylaxis of diabetes.

Moreover preferred are compounds of the formula (I) as described above for the preparation of a medicament for the treatment or prophylaxis of type II diabetes.

Also more preferred are compounds of the formula (I) as described above for the preparation of a medicament for the treatment or prophylaxis of diabetic nephropathy.

A further preferred embodiment of the present invention is the use of a compound according to formula (I) as described above for the preparation of a medicament for the treatment or prophylaxis of atherosclerosis, metabolic syndrome, diabetes, diabetic nephropathy, obesity, dyslipidemia, particularly high LDL-cholesterol, high triglycerides and low HDL-cholesterol, diseases of cholesterol absorption, cholesterol gallstone disease, coronary heart disease, peripheral artery disease, stroke, cholestasis and fibrosis of the liver, non-alcoholic steatohepatitis, non-alcoholic fatty liver disease.

Also a further preferred embodiment of the present invention is the use of a compound according to formula (I) as described above for the preparation of a medicament for the treatment or prophylaxis of psoriasis, cancer, particularly gastrointestinal cancer, osteoporosis, Parkinson's disease or Alzheimer's disease.

Particularly preferred is the use of a compound according to formula (I) as described above for the preparation of medicaments for the treatment or prophylaxis of atherosclerosis, diabetes, non-alcoholic steatohepatitis or diabetic nephropathy.

More preferred is the use of a compound according to formula (I) as described above for the preparation of medicaments for the treatment or prophylaxis of diabetes.

Moreover preferred is the use of a compound according to formula (I) as described above for the preparation of medicaments for the treatment or prophylaxis of type II diabetes.

Another more preferred is the use of a compound according to formula (I) as described above for the preparation of medicaments for the treatment or prophylaxis of diabetic nephropathy.

A further object of the present invention comprises a compound according to formula (I) as described above, when manufactured according to any one of the described processes.

Also an object of the invention is a method for the treatment or prophylaxis of atherosclerosis, metabolic syndrome, diabetes, diabetic nephropathy, obesity, dyslipidemia, particularly high LDL-cholesterol, high triglycerides and low HDL-cholesterol, diseases of cholesterol absorption, cholesterol gallstone disease, coronary heart disease, peripheral artery disease, stroke, cholestasis and fibrosis of the liver, non-alcoholic steatohepatitis, non-alcoholic fatty liver disease, psoriasis, cancer, particularly gastrointestinal cancer, osteoporosis, Parkinson's disease or Alzheimer's disease, which method comprises administering an effective amount of a compound according to formula (I) as described above.

Particularly preferred is a method for the treatment or prophylaxis of atherosclerosis, diabetes, non-alcoholic steatohepatitis or diabetic nephropathy, which method comprises administering an effective amount of a compound according to formula (I) as described above.

More preferred is a method for the treatment or prophylaxis of diabetes, which method comprises administering an effective amount of a compound according to formula (I) as described above.

Moreover preferred is a method for the treatment or prophylaxis of type II diabetes, which method comprises administering an effective amount of a compound according to formula (I) as described above Also more preferred is a method for the treatment or prophylaxis of diabetic nephropathy, which method comprises administering an effective amount of a compound according to formula (I) as described above.

Assay Procedures

The following tests were carried out in order to determine the activity of the compounds of formula (I). Background information on the binding assay can be found in: Nichols J S et al. "Development of a scintillation proximity assay for peroxisome proliferator-activated receptor gamma ligand binding domain", (1998) Anal. Biochem. 257: 112-119.

Bacterial and mammalian expression vectors were constructed to produce glutathione-s-transferase (GST) and Gal4 DNA binding domain (GAL) proteins fused to the ligand binding domain (LBD) of human FXR (aa 193-473). To accomplish this, the portions of the sequences encoding the FXR LBD were amplified by polymerase chain reaction (PCR) from a full-length clone by PCR and then subcloned into the plasmid vectors. The final clone was verified by DNA sequence analysis.

The induction, expression, and subsequent purification of GST-LBD fusion protein was performed in *E. coli* strain BL21 (pLysS) cells by standard methods (Current Protocols in Molecular Biology, Wiley Press, ed. Ausubel et al.).

Radioligand Binding Assay

Binding of test substances to the FXR ligand binding domain was assessed in a radioligand displacement assay. The assay was performed in a buffer consisting of 50 mM Hepes, pH 7.4, 10 mM NaCl, 5 mM $MgCl_2$, 0.01% CHAPS. For each reaction well in a 96-well plate, 40 nM of GST-FXR LBD fusion protein was bound to 10 g glutathione ytrium silicate SPA beads (PharmaciaAmersham) in a final volume of 50 l by shaking. A radioligand (e.g., 20 nM of 2,N-dicyclohexyl-2-[2-(2,4 dimethoxy-phenyl)-benzoimidazol-1-yl]-acetamide) and test compounds were added, and scintillation proximity counting was performed. All binding assays were performed in 96-well plates and the amount of bound ligand was measured on a Packard TopCount using OptiPlates (Packard). Dose response curves were performed within a range of test compound concentrations from $6\times10^{-9}$ M to $2.5\times10^{-5}$ M and $IC_{50}$ values were calculated.

| Examples | Radioligand Binding Assay $IC_{50}$ (uM) |
|---|---|
| 1 | 0.2 |
| 2 | 2.9 |
| 3 | 0.7 |
| 4 | 5.8 |
| 5 | 12.1 |
| 6 | 1.8 |
| 7 | 3.8 |
| 8 | 5.6 |
| 9 | 10.5 |
| 10 | 12.8 |
| 11 | 0.8 |
| 12 | 1.5 |
| 13 | 3.6 |
| 14 | 5.2 |
| 15 | 2.6 |
| 16 | 66.1 |
| 17 | 10.2 |
| 18 | 30.4 |
| 19 | 0.3 |
| 20 | 0.2 |
| 21 | 0.3 |
| 22 | 0.2 |
| 23 | 0.2 |
| 24 | 0.7 |
| 25 | 0.1 |
| 26 | 2.1 |
| 27 | 0.5 |
| 28 | 0.2 |
| 29 | 0.7 |
| 30 | 0.4 |
| 31 | 0.05 |
| 32 | 0.01 |
| 33 | 0.04 |
| 34 | 0.03 |
| 35 | 0.05 |
| 36 | 0.09 |
| 37 | 0.2 |
| 38 | 0.2 |
| 39 | 0.03 |
| 40 | 0.004 |
| 41 | 0.2 |
| 42 | 0.04 |
| 43 | 0.09 |
| 44 | 0.1 |
| 45 | 0.1 |
| 46 | 0.4 |
| 47 | 0.9 |
| 48 | 0.4 |
| 49 | 1.1 |
| 50 | 1.9 |
| 51 | 0.5 |
| 52 | 0.8 |
| 53 | 1.7 |
| 54 | 1.2 |
| 55 | 2.6 |
| 56 | 0.5 |
| 57 | 0.2 |
| 58 | 0.03 |
| 59 | 0.3 |
| 60 | 1.3 |
| 61 | 0.5 |
| 62 | 0.4 |
| 63 | 0.7 |
| 64 | 0.2 |
| 65 | 3.7 |
| 66 | 1.8 |
| 67 | 0.09 |
| 68 | 0.04 |
| 69 | 0.08 |
| 70 | 0.01 |
| 71 | 1.1 |
| 72 | 3.6 |
| 73 | 0.01 |
| 74 | 0.03 |
| 75 | 0.03 |
| 76 | 0.1 |
| 77 | 0.03 |
| 78 | 0.09 |
| 79 | 0.08 |
| 80 | 0.03 |
| 81 | 0.04 |
| 82 | 0.01 |
| 83 | 0.01 |
| 84 | 0.0002 |
| 85 | 0.0006 |
| 86 | 0.003 |
| 87 | 0.02 |
| 88 | 0.01 |
| 89 | 0.06 |
| 90 | 1.6 |
| 91 | 0.05 |
| 92 | 0.02 |
| 93 | 0.06 |
| 94 | 0.04 |
| 95 | 0.01 |
| 96 | 0.02 |

In the foregoing Radioligand Binding assay, compounds according to formula (I) as described above have $IC_{50}$ values between 0.0000001 uM and 1000 uM, preferred compounds have $IC_{50}$ values between 0.0001 uM and 50 uM, particularly preferred compounds have $IC_{50}$ values between 0.0001 uM and 0.5 uM (uM means microMolar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula (I) and their pharmaceutically acceptable salts can be used for the prophylaxis or treatment of atherosclerosis, diabetes, non-alcoholic steatohepatitis or diabetic nephropathy. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

1-Cyclohexylmethyl-2-(2-cyclopentylmethoxy-pyridin-3-yl)-5,6-difluoro-1H-benzoimidazole

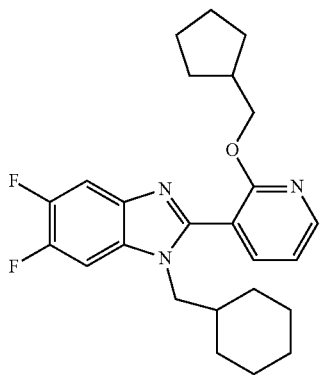

To a suspension of sodium hydride (20 mg, 0.51 mmol, 60%) in dry N,N-dimethylformamide (5 ml) at 25° C. was slowly added a solution of cyclopentyl-methanol (30 mg, 0.30 mmol; CAS Reg. No. 3637-61-4) in dry N,N-dimethylformamide (5 ml) and the suspension was stirred for 0.5 h. A solution of 2-(2-chloro-pyridin-3-yl)-1-cyclohexylmethyl-5,6-difluoro-1H-benzoimidazole (90 mg, 0.25 mmol) in N,N-dimethylformamide (5 ml) was then added drop wise to the above solution and further stirred for 16 h at 25° C. The reaction mixture was quenched with saturated aqueous solution of ammonium chloride. The solvents were removed under reduced pressure. The crude material dissolved in ethyl acetate, washed with water and brine, dried over sodium sulfate, filtered, and evaporated under reduced pressure. The crude product was purified by column chromatography over silica gel (20-30% ethyl acetate/n-hexane) to afford the title compound as a colorless solid (54%). MS (Turbo Spray): m/z=426.3 (M+H).

Intermediates a) 2-(2-Chloro-pyridin-3-yl)-1-cyclohexylmethyl-5,6-difluoro-1H-benzoimidazole To a suspension of sodium hydride (0.40 g, 60%, 10 mmol) in dry N,N-dimethylformamide (10 ml) at 25° C. was slowly added a solution of 2-(2-chloro-pyridin-3-yl)-5,6-difluoro-1H-benzoimidazole (1.33 g, 5 mmol) in dry N,N-dimethylformamide (5 ml), and was allowed to stir for 0.5 h. A solution of bromomethyl-cyclohexane (1.06 g, 6 mmol; CAS Reg. No. 2550-36-9) in N,N-dimethylformamide (5 ml) was then added drop wise to the above solution, and further stirred for 16 h at 25° C. The reaction mixture was quenched with saturated aqueous solution of ammonium chloride. The solvents were removed under reduced pressure. The crude material was dissolved in ethyl acetate, washed with water, and then with brine, dried over sodium sulfate, filtered, and evaporated under reduced pressure. The crude product was purified by column chromatography over silica gel (20% ethyl acetate/n-hexane) to afford the title compound as a colorless solid (51%). MS (Turbo Spray): m/z=362.2 (M+H).

b) 2-(2-Chloro-pyridin-3-yl)-5,6-difluoro-1H-benzoimidazole

To a suspension of 2-chloro-nicotinic acid (4.10 g, 0.026 mol; CAS Reg. No. 2942-59-8) in polyphosphoric acid (50 g) was added 4,5-difluoro-benzene-1,2-diamine (3.86 g, 0.026 mol; CAS Reg. No. 76179-40-3) and the resulting mixture was heated to 180° C. for 1 h. The reaction mixture was then cooled and neutralized with ice cold 10% aqueous sodium carbonate solution, and then extracted with ethyl acetate. The combined organic layer was dried over sodium sulfate, filtered, and evaporated under reduced pressure. The crude residue thus obtained was purified by column chromatography over silica gel (25% ethyl acetate/n-hexane) to give the title compound as a brown solid (48%). MS (Turbo Spray): m/z=266.1 (M+H).

Example 2

1-Cyclohexylmethyl-2-(2-cyclopropylmethoxy-pyridin-3-yl)-5,6-difluoro-1H-benzoimidazole

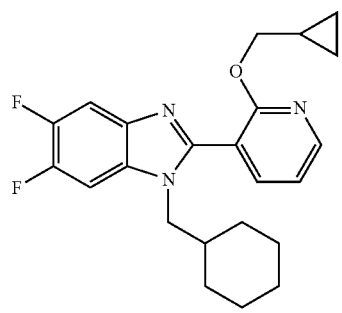

The title compound was prepared in analogy to Example 1, from 2-(2-chloro-pyridin-3-yl)-1-cyclohexylmethyl-5,6-difluoro-1H-benzoimidazole (Example 1, intermediate a) and cyclopropyl-methanol (CAS Reg. No. 2516-33-8). Colorless semi-solid (16%). MS (Turbo Spray): m/z=398.3 (M+H).

Example 3

2-[2-(2-Chloro-benzyloxy)-pyridin-3-yl]-1-cyclohexylmethyl-5,6-difluoro-1H-benzoimidazole

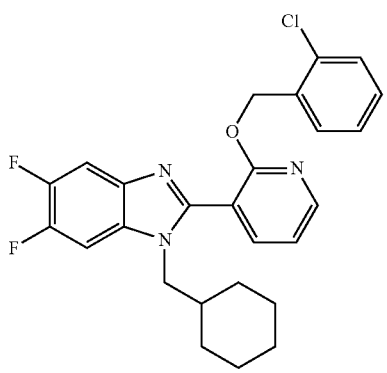

The title compound was prepared in analogy to Example 1, from 2-(2-chloro-pyridin-3-yl)-1-cyclohexylmethyl-5,6-difluoro-1H-benzoimidazole (Ex. 1, intermediate a) and (2-chloro-phenyl)-methanol (CAS Reg. No. 17849-38-6). Light yellow solid (48%). MS (Turbo Spray): m/z=468.2 (M+H).

Example 4

4-[3-(1-Cyclohexylmethyl-5,6-difluoro-1H-benzoimidazol-2-yl)-pyridin-2-yloxymethyl]-benzoic acid

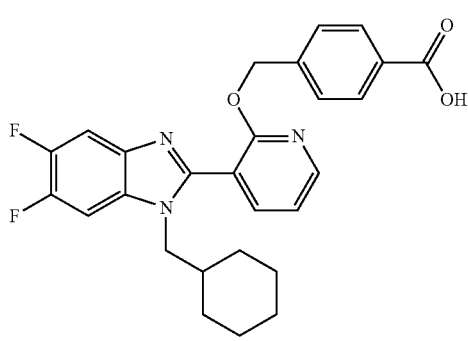

A solution of 4-[3-(1-cyclohexylmethyl-5,6-difluoro-1H-benzoimidazol-2-yl)-pyridin-2-yloxymethyl]-benzoic acid methyl ester (84 mg, 0.17 mmol) in tetrahydrofuran (20 ml) and water (10 ml) was treated with an aqueous solution of lithium hydroxide monohydrate (36 mg, 0.86 mmol) and stirred at 25° C. for 2 h. The solvent removed in vacuo, the resulting crude material diluted with water (5 ml) and acidified with 2M aqueous hydrochloric acid solution. The aqueous layer was extracted with ethyl acetate, washed with water, brine, dried over sodium sulfate, filtered and evaporated under reduced pressure. The crude product was purified by column chromatography over silica gel (50% ethyl acetate/n-hexane) to afford the final compound as an off-white powder (26%). MS (Turbo Spray): m/z=478.4 (M+H).

Intermediate

4-[3-(1-Cyclohexylmethyl-5,6-difluoro-1H-benzoimidazol-2-yl)-pyridin-2-yloxymethyl]-benzoic acid methyl ester A solution of 4-hydroxymethyl-benzoic acid methyl ester (0.14 g, 0.84 mmol; CAS Reg. No. 6908-41-4), palladium (II) acetate (19 mg, 0.084 mmol; CAS Reg. No.) and 2,2'-bis (diphenylphosphino)-1,1'-binaphthyl (52 mg, 0.084 mmol; CAS Reg. No.) in dry toluene (10 ml) was stirred at 25° C. for 5 min. under argon atmosphere. To the resulting deep red solution was then added a solution of 2-(2-chloro-pyridin-3-yl)-1-cyclohexylmethyl-5,6-difluoro-1H-benzoimidazole (Ex. 1, intermediate a, 0.30 g, 0.84 mmol) in toluene (5 ml) and cesium carbonate (0.82 g, 2.52 mmol). The flask was purged with argon, and the reaction mixture was heated at 100° C. for 12 h. The solid was filtered, the filtrate concentrated in vacuo and the residue was purified by column chromatography over silica gel (15-20% ethyl acetate/n-hexane) to afford the title compound as brown sticky solid (60%). MS (Turbo Spray): m/z=492.3 (M+H).

Example 5

{4-[3-(1-Cyclohexylmethyl-5,6-difluoro-1H-benzoimidazol-2-yl)-pyridin-2-yloxymethyl]-phenoxy}-acetic acid

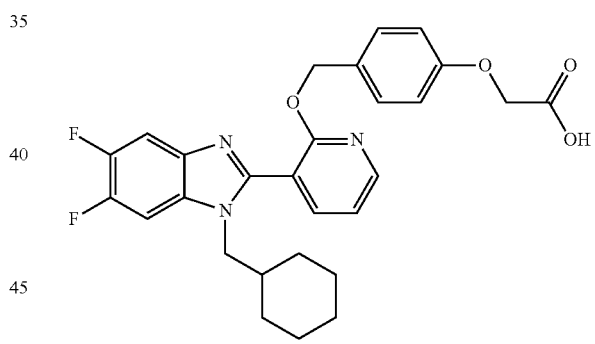

The title compound was prepared in analogy to Example 4, from {-4-[3-(1-cyclohexylmethyl-5,6-difluoro-1H-benzoimidazol-2-yl)-pyridin-2-yloxymethyl]-phenoxy}-acetic acid methyl ester. Off-white powder (42%). MS (Turbo Spray): m/z=508.4 (M+H).

Intermediates a) {4-[3-(1-Cyclohexylmethyl-5,6-difluoro-1H-benzoimidazol-2-yl)-pyridin-2-yloxymethyl]-phenoxy}-acetic acid methyl ester To a stirred solution of 3-(1-cyclohexylmethyl-5,6-difluoro-1H-benzoimidazol-2-yl)-pyridin-2-ol (58 mg, 0.17 mmol) in acetone (10 ml) was added cesium carbonate (0.085 g, 0.26 mmol) followed by (4-bromomethyl-phenoxy)-acetic acid methyl ester (49 mg, 0.19 mmol; CAS Reg. No. 104508-23-8) and the reaction mixture was refluxed for 2 h. The reaction mixture was filtered, and the filtrate was evaporated under reduced pressure. The residue was purified by column chromatography using silica gel (50-60% ethyl acetate/n-hexane) to yield the desired compound as a brown solid (50%). MS (Turbo Spray): m/z=522.5 (M+H).

b) 3-(1-Cyclohexylmethyl-5,6-difluoro-1H-benzoimidazol-2-yl)-pyridin-2-ol

To a stirred solution of 1-cyclohexylmethyl-5,6-difluoro-2-[2-(4-methoxy-benzyloxy)-pyridin-3-yl]-1H-benzoimidazole (2.32 g, 5 mmol) in dichloromethane (40 ml) was added boron tri bromide (1M solution in dichloromethane; 21 ml, 21 mmol) at 25° C., and the resulting mixture was allowed to stir for 16 h at the same temperature. The reaction mixture was then quenched with saturated aqueous solution of sodium bi carbonate solution, further diluted with dichloromethane (30 ml). Organic layer was washed with water, and then with brine, dried over sodium sulfate, filtered, and evaporated under reduced pressure to afford the crude material. Crude product was purified by column chromatography using silica gel (5-10% ethyl acetate/n-hexane) to give the title compound as a colorless solid (39%). MS (Turbo Spray): m/z=344.3 (M+H).

c) 1-Cyclohexylmethyl-5,6-difluoro-2-[2-(4-methoxy-benzyloxy)-pyridin-3-yl]-1H-benzoimidazole The title compound was prepared in analogy to Example 4, intermediate, from 2-(2-chloro-pyridin-3-yl)-1-cyclohexylmethyl-5,6-difluoro-1H-benzoimidazole (Ex. 1, intermediate a) and (4-methoxy-phenyl)-methanol (CAS Reg. No. 105-13-5). Colorless solid (31%). MS (Turbo Spray): m/z=464.2 (M+H).

Example 6

1-Benzyl-2-[2-(2-chloro-benzyloxy)-pyridin-3-yl]-5,6-difluoro-1H-benzoimidazole

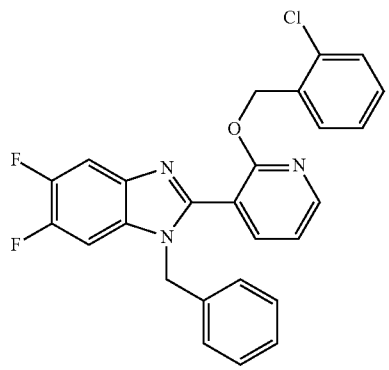

The title compound was prepared in analogy to Example 1, from 1-benzyl-2-(2-chloro-pyridin-3-yl)-5,6-difluoro-1H-benzoimidazole and (3-chloro-phenyl)-methanol (CAS Reg. No. 873-63-2). Colorless solid (47%). MS (Turbo Spray): m/z=462.1 (M+H).

Intermediate

1-Benzyl-2-(2-chloro-pyridin-3-yl)-5,6-difluoro-1H-benzoimidazole

The title compound was prepared in analogy to Example 1, intermediate a, from 2-(2-chloro-pyridin-3-yl)-5,6-difluoro-1H-benzoimidazole and bromomethyl-benzene (CAS Reg. No. 100-39-0). Colorless solid (52%). MS (Turbo Spray): m/z=356.3 (M+H).

Example 7

1-Benzyl-2-(2-cyclopentylmethoxy-pyridin-3-yl)-5,6-difluoro-1H-benzoimidazole

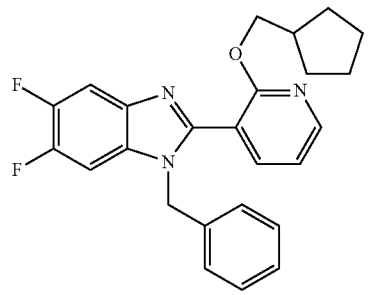

The title compound was prepared in analogy to Example 1, from 1-benzyl-2-(2-chloro-pyridin-3-yl)-5,6-difluoro-1H-benzoimidazole (Example 6, intermediate) and cyclopentyl-methanol (CAS Reg. No. 3637-61-4). Light yellow powder (42%). MS (Turbo Spray): m/z=419.9 (M+H).

Example 8

1-Benzyl-2-(2-cyclopropylmethoxy-pyridin-3-yl)-5,6-difluoro-1H-benzoimidazole

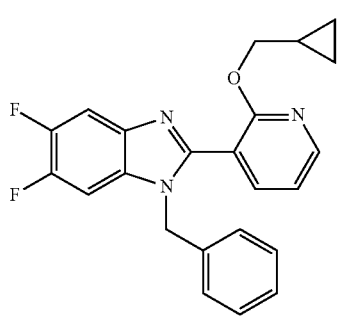

The title compound was prepared in analogy to Example 1, from 1-benzyl-2-(2-chloro-pyridin-3-yl)-5,6-difluoro-1H-benzoimidazole (Example 6, intermediate) and cyclopropyl-methanol (CAS Reg. No. 2516-33-8). Colorless powder (23%). MS (Turbo Spray): m/z=392.2 (M+H).

Example 9

4-[3-(1-Benzyl-5,6-difluoro-1H-benzoimidazol-2-yl)-pyridin-2-yloxymethyl]-benzoic acid

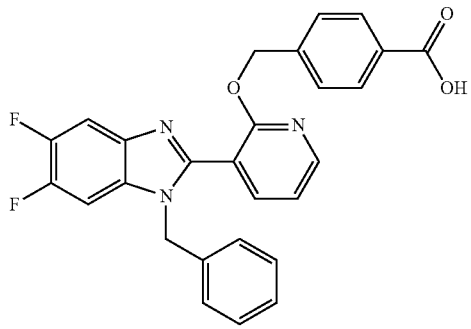

The title compound was prepared in analogy to Example 4, from 4-[3-(1-benzyl-5,6-difluoro-1H-benzoimidazol-2-yl)-pyridin-2-yloxymethyl]-benzoic acid methyl ester. Off-white sticky solid (41%). MS (Turbo Spray): m/z=472.4 (M+H).

Intermediate

4-[3-(1-Benzyl-5,6-difluoro-1H-benzoimidazol-2-yl)-pyridin-2-yloxymethyl]-benzoic acid methyl ester The title compound was prepared in analogy to Example 4, intermediate, from 1-benzyl-2-(2-chloro-pyridin-3-yl)-5,6-difluoro-1H-benzoimidazole (Example 6, intermediate) and 4-hydroxymethyl-benzoic acid methyl ester (CAS Reg. No. 6908-41-4). Brown sticky solid (15%). MS (Turbo Spray): m/z=386.2 (M+H).

Example 10

{4-[3-(1-Benzyl-5,6-difluoro-1H-benzoimidazol-2-yl)-pyridin-2-yloxymethyl]-phenoxy}-acetic acid

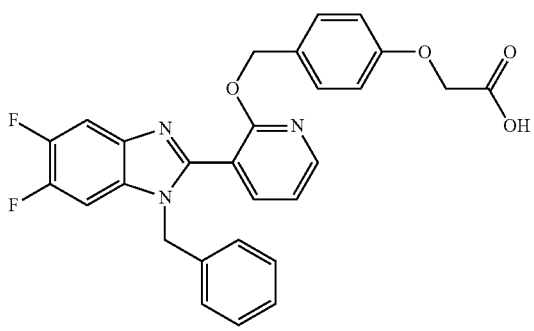

The title compound was prepared in analogy to Example 4, from {4-[3-(1-benzyl-5,6-difluoro-1H-benzoimidazol-2-yl)-pyridin-2-yloxymethyl]-phenoxy}-acetic acid methyl ester. Colorless powder (28%). MS (Turbo Spray): m/z=502.2 (M+H).

Intermediates a) {4-[3-(1-Benzyl-5,6-difluoro-1H-benzoimidazol-2-yl)-pyridin-2-yloxymethyl]-phenoxy}-acetic acid methyl ester The title compound was prepared in analogy to Example 5, intermediate a, from 3-(1-benzyl-5,6-difluoro-1H-benzoimidazol-2-yl)-pyridin-2-ol and (4-bromomethyl-phenoxy)-acetic acid methyl ester (CAS Reg. No. 104508-23-8). Brown solid (65%). MS (Turbo Spray): m/z=516.3 (M+H).

b) 3-(1-Benzyl-5,6-difluoro-1H-benzoimidazol-2-yl)-pyridin-2-ol

The title compound was prepared in analogy to Example 5, intermediate b, from 1-benzyl-5,6-difluoro-2-[2-(4-methoxy-benzyloxy)-pyridin-3-yl]-1H-benzoimidazole. Colorless solid (29%). MS (Turbo Spray): m/z=338.3 (M+H).

c) 1-Benzyl-5,6-difluoro-2-[2-(4-methoxy-benzyloxy)-pyridin-3-yl]-1H-benzoimidazole The title compound was prepared in analogy to Example 5, intermediate c, from 1-benzyl-2-(2-chloro-pyridin-3-yl)-5,6-difluoro-1H-benzoimidazole (Example 6, intermediate) and (4-methoxy-phenyl)-methanol (CAS Reg. No. 105-13-5). Colorless solid (72%). MS (Turbo Spray): m/z=458.1 (M+H).

Example 11

1-(3-Chloro-benzyl)-2-[2-(2-chloro-benzyloxy)-pyridin-3-yl]-5,6-difluoro-1H-benzoimidazole

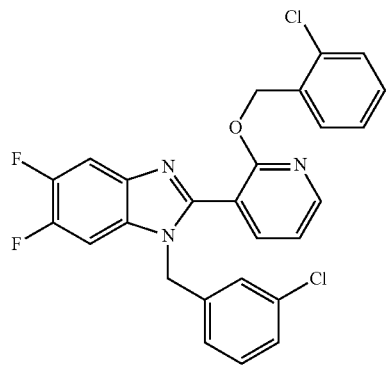

The title compound was prepared in analogy to Example 1, from 1-(3-chloro-benzyl)-2-(2-chloro-pyridin-3-yl)-5,6-difluoro-1H-benzoimidazole and (3-chloro-phenyl)-methanol (CAS Reg. No. 873-63-2). Colorless powder (31%). MS (Turbo Spray): m/z=496.1 (M+H).

Intermediate

1-(3-Chloro-benzyl)-2-(2-chloro-pyridin-3-yl)-5,6-difluoro-1H-benzoimidazole The title compound was prepared in analogy to Example 1, intermediate a, from 2-(2-chloro-pyridin-3-yl)-5,6-difluoro-1H-benzoimidazole (Example 1, intermediate b) and 1-bromomethyl-3-chloro-benzene (CAS Reg. No. 766-80-3). Colorless powder (55%). MS (Turbo Spray): m/z=389.9 (M+H).

Example 12

1-(3-Chloro-benzyl)-2-(2-cyclopentylmethoxy-pyridin-3-yl)-5,6-difluoro-1H-benzoimidazole

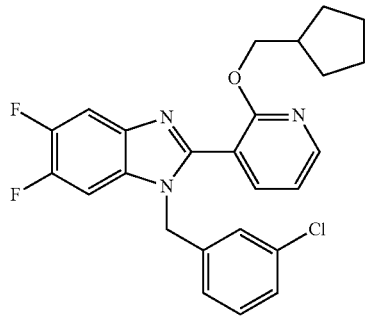

The title compound was prepared in analogy to Example 1, from 1-(3-chloro-benzyl)-2-(2-chloro-pyridin-3-yl)-5,6-difluoro-1H-benzoimidazole (Example 11, intermediate) and cyclopentyl-methanol (CAS Reg. No. 3637-61-4). Colorless powder (52%). MS (Turbo Spray): m/z=454.1 (M+H).

Example 13

1-(3-Chloro-benzyl)-2-(2-cyclopropylmethoxy-pyridin-3-yl)-5,6-difluoro-1H-benzoimidazole

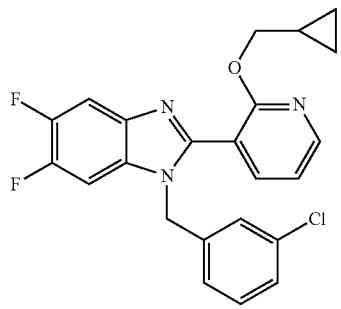

The title compound was prepared in analogy to Example 1, from 1-(3-chloro-benzyl)-2-(2-chloro-pyridin-3-yl)-5,6-difluoro-1H-benzoimidazole (Example 11, intermediate) and cyclopropyl-methanol (CAS Reg. No. 2516-33-8). Colorless powder (20%). MS (Turbo Spray): m/z=426.2 (M+H).

Example 14

4-{3-[1-(3-Chloro-benzyl)-5,6-difluoro-1H-benzoimidazol-2-yl]-pyridin-2-yloxymethyl}-benzoic acid

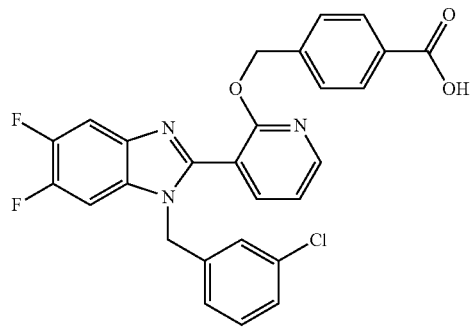

The title compound was prepared in analogy to Example 4, from 4-{3-[1-(3-chloro-benzyl)-5,6-difluoro-1H-benzoimidazol-2-yl]-pyridin-2-yloxymethyl}-benzoic acid methyl ester. Colorless powder (46%). MS (Turbo Spray): m/z=506.1 (M+H).

Intermediate

4-{3-[1-(3-Chloro-benzyl)-5,6-difluoro-1H-benzoimidazol-2-yl]-pyridin-2-yloxymethyl}-benzoic acid methyl ester The title compound was prepared in analogy to Example 4, intermediate, from 1-(3-chloro-benzyl)-2-(2-chloro-pyridin-3-yl)-5,6-difluoro-1H-benzoimidazole (Example 11, intermediate) and 4-hydroxymethyl-benzoic acid methyl ester (CAS Reg. No. 6908-41-4). Colorless sticky solid (34%). MS (Turbo Spray): m/z=519.9 (M+H).

Example 15

(4-{3-[1-(3-Chloro-benzyl)-5,6-difluoro-1H-benzoimidazol-2-yl]-pyridin-2-yloxymethyl}-phenoxy)-acetic acid

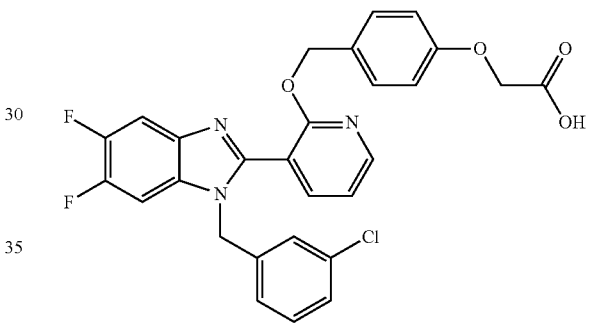

The title compound was prepared in analogy to Example 4, from (4-{3-[1-(3-chloro-benzyl)-5,6-difluoro-1H-benzoimidazol-2-yl]-pyridin-2-yloxymethyl}-phenoxy)-acetic acid methyl ester. Light yellow powder (51%). MS (Turbo Spray): m/z=536.1 (M+H).

Intermediates a) (4-{3-[1-(3-Chloro-benzyl)-5,6-difluoro-1H-benzoimidazol-2-yl]-pyridin-2-yloxymethyl}-phenoxy)-acetic acid methyl ester The title compound was prepared in analogy to Example 5, intermediate a, from 3-[1-(3-chloro-benzyl)-5,6-difluoro-1H-benzoimidazol-2-yl]-pyridin-2-ol and (4-bromomethyl-phenoxy)-acetic acid methyl ester (CAS Reg. No. 104508-23-8). Colorless powder (67%). MS (Turbo Spray): m/z=550.1 (M+H).

b) 3-[1-(3-Chloro-benzyl)-5,6-difluoro-1H-benzoimidazol-2-yl]-pyridin-2-ol

The title compound was prepared in analogy to Example 5, intermediate b, from 1-(3-chloro-benzyl)-5,6-difluoro-2-[2-(4-methoxy-benzyloxy)-pyridin-3-yl]-1H-benzoimidazole. Colorless powder (27%). MS (Turbo Spray): m/z=372.3 (M+H).

c) 1-(3-Chloro-benzyl)-5,6-difluoro-2-[2-(4-methoxy-benzyloxy)-pyridin-3-yl]-1H-benzoimidazole The title compound was prepared in analogy to Example 5, intermediate c, from 1-(3-chloro-benzyl)-2-(2-chloro-pyridin-3-yl)-5,6-difluoro-1H-benzoimidazole (Example 11, intermediate) and (4-methoxy-phenyl)-methanol (CAS Reg. No. 105-13-5). Off-white powder (87%). MS (Turbo Spray): m/z=492.3 (M+H).

Example 16

3-{4-[2-(2-Cyclopropylmethoxy-pyridin-3-yl)-5,6-difluoro-benzoimidazol-1-ylmethyl]-phenyl}-propionic acid

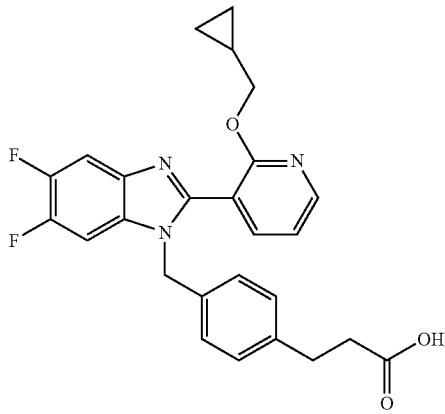

The title compound was synthesized in analogy to Example 4, from 3-{4-[2-(2-cyclopropylmethoxy-pyridin-3-yl)-5,6-difluoro-benzoimidazol-1-ylmethyl]-phenyl}-propionic acid methyl ester. Off-white powder (35%). MS (Turbo Spray): m/z=464.4 (M+H).

Intermediates a) 3-{4-[2-(2-Cyclopropylmethoxy-pyridin-3-yl)-5,6-difluoro-benzoimidazol-1-ylmethyl]-phenyl}-propionic acid methyl ester To a stirred solution of 3-{4-[5,6-difluoro-2-(2-hydroxy-pyridin-3-yl)-benzoimidazol-1-ylmethyl]-phenyl}-propionic acid methyl ester (72 mg, 0.17 mmol) in acetone (10 ml) was added cesium carbonate (85 mg, 0.26 mmol) followed by bromomethyl-cyclopropane (26 mg, 0.19 mmol; CAS Reg. No. 7051-34-5) and the reaction was refluxed for 2 h. The reaction mixture was filtered and the filtrate removed under reduced pressure. The residue was purified by column chromatography using silica gel (50-60% ethyl acetate/n-hexane) to afford the desired product as a brown solid (67%). MS (Turbo Spray): m/z=478.5 (M+H).

b) 3-{4-[5,6-Difluoro-2-(2-hydroxy-pyridin-3-yl)-benzoimidazol-1-ylmethyl]-phenyl}-propionic acid methyl ester The title compound was synthesized in analogy to Example 5, intermediate b, from 3-(4-{5,6-difluoro-2-[2-(4-methoxy-benzyloxy)-pyridin-3-yl]-benzoimidazol-1-ylmethyl}-phenyl)-propionic acid methyl ester. Colorless solid (69%). MS (Turbo Spray): m/z=424.3 (M+H).

c) 3-(4-{5,6-Difluoro-2-[2-(4-methoxy-benzyloxy)-pyridin-3-yl]-benzoimidazol-1-ylmethyl}-phenyl)-propionic acid methyl ester The title compound was prepared in analogy to Example 4, intermediate, from 3-{4-[2-(2-chloro-pyridin-3-yl)-5,6-difluoro-benzoimidazol-1-ylmethyl]-phenyl}-propionic acid methyl ester and (4-methoxy-phenyl)-methanol (CAS Reg. No. 105-13-5). Colorless sticky solid (81%). MS (Turbo Spray): m/z=544.1 (M+H).

d) 3-{4-[2-(2-Chloro-pyridin-3-yl)-5,6-difluoro-benzoimidazol-1-ylmethyl]-phenyl}-propionic acid methyl ester The title compound was prepared in analogy to Example 1, intermediate a, from 2-(2-chloro-pyridin-3-yl)-5,6-difluoro-1H-benzoimidazole (Example 1, intermediate b) and 3-(4-bromomethyl-phenyl)-propionic acid methyl ester (CAS Reg. No. 56607-18-2). Brown solid (65%). MS (Turbo Spray): m/z=442.2 (M+H).

Example 17

3-(4-{2-[2-(2-Chloro-benzyloxy)-pyridin-3-yl]-5,6-difluoro-benzoimidazol-1-ylmethyl}-phenyl)-propionic acid

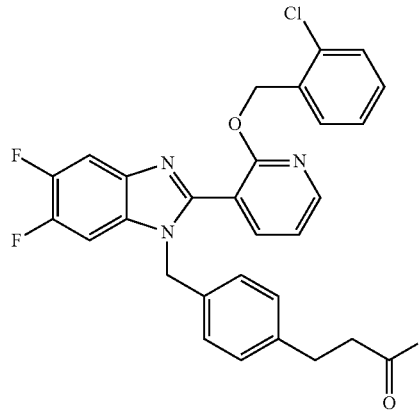

The title compound was prepared in analogy to Example 4, from 3-(4-{2-[2-(2-chloro-benzyloxy)-pyridin-3-yl]-5,6-difluoro-benzoimidazol-1-ylmethyl}-phenyl)-propionic acid methyl ester. Off-white powder (42%). MS (Turbo Spray): m/z=534.2 (M+H).

Intermediate 3-(4-{2-[2-(2-Chloro-benzyloxy)-pyridin-3-yl]-5,6-difluoro-benzoimidazol-1-ylmethyl}-phenyl)-propionic acid methyl ester The title compound was prepared in analogy to Example 16, intermediate a, from 3-{4-[5,6-difluoro-2-(2-hydroxy-pyridin-3-yl)-benzoimidazol-1-ylmethyl]-phenyl}-propionic acid methyl ester (Example 16, intermediate b) and 1-bromomethyl-3-chloro-benzene (CAS Reg. No. 766-80-3). Brown solid (98%). MS (Turbo Spray): m/z=548.2 (M+H).

Example 18

3-{4-[2-(2-Cyclopentylmethoxy-pyridin-3-yl)-5,6-difluoro-benzoimidazol-1-ylmethyl]-phenyl}-propionic acid

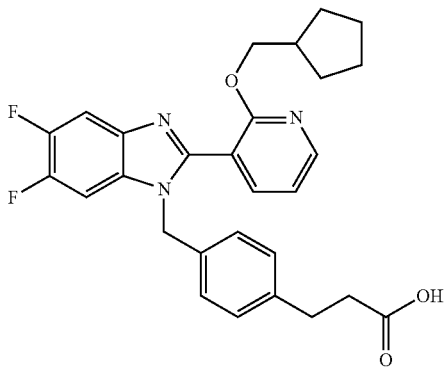

The title compound was prepared in analogy to Example 4, from 3-{4-[2-(2-cyclopentylmethoxy-pyridin-3-yl)-5,6-difluoro-benzoimidazol-1-ylmethyl]-phenyl}-propionic acid methyl ester. Colorless powder (52%). MS (Turbo Spray): m/z=492.3 (M+H).

Intermediate

3-{4-[2-(2-Cyclopentylmethoxy-pyridin-3-yl)-5,6-difluoro-benzoimidazol-1-ylmethyl]-phenyl}-propionic acid methyl ester The title compound was prepared in analogy to Example 16, intermediate a, from 3-{4-[5,6-difluoro-2-(2-hydroxy-pyridin-3-yl)-benzoimidazol-1-ylmethyl]-phenyl}-propionic acid methyl ester (Example 16, intermediate b) and bromomethyl-cyclopentane (CAS Reg. No. 3814-30-0). White powder (73%). MS (Turbo Spray): m/z=506.4 (M+H).

Example 19

2-[4-Chloro-2-(2-chloro-benzyloxy)-phenyl]-1-cyclohexylmethyl-5,6-difluoro-1H-benzoimidazole

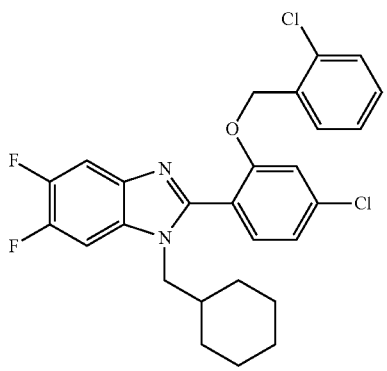

To a suspension of sodium hydride (16 mg, 0.4 mmol, 60%) in dry N,N-dimethylformamide (10 ml) at 25° C. was slowly added a solution of 5-chloro-2-(1-cyclohexylmethyl-5,6-difluoro-1H-benzoimidazol-2-yl)-phenol (0.10 g, 0.275 mmol) in dry N,N-dimethylformamide (5 ml), and was allowed to stir for 0.5 h. A solution of 1-bromomethyl-2-chloro-benzene (82 mg, 0.4 mmol; CAS Reg. No. 611-17-6) in N,N-dimethylformamide (5 ml) was then added drop wise to the above solution, and further stirred for 16 h at 25° C. The reaction mixture was quenched with saturated aqueous solution of ammonium chloride. The solvents were removed under reduced pressure. The crude material dissolved in ethyl acetate, washed with water, and then with brine, dried over sodium sulfate, filtered, and evaporated under reduced pressure. The crude product was purified by column chromatography over silica gel (10-20% ethyl acetate/n-hexane) to afford the title compound as a colorless powder (38%). MS (Turbo Spray): m/z=501.2 (M+H).

Intermediates a) 5-Chloro-2-(1-cyclohexylmethyl-5,6-difluoro-1H-benzoimidazol-2-yl)-phenol To a stirred solution of 2-(4-chloro-2-methoxy-phenyl)-1-cyclohexylmethyl-5,6-difluoro-1H-benzoimidazole (1.95 g, 5 mmol) in dichloromethane (40 ml) was added boron tri bromide (1M solution in dichloromethane; 21 ml, 21 mmol) at 25° C., and the resulting mixture was allowed to stir for 16 h at the same temperature. The reaction mixture was then quenched with saturated aqueous solution of sodium bicarbonate solution and further diluted with dichloromethane (30 ml). The organic layer was washed with water, and then with brine, dried over sodium sulfate, filtered, and evaporated under reduced pressure to afford the crude material. Crude product was purified by column chromatography using silica gel (5-10% ethyl acetate/n-hexane) to give the desired compound as a colorless powder (62%). MS (Turbo Spray): m/z=376.9 (M+H).

b) 2-(4-Chloro-2-methoxy-phenyl)-1-cyclohexylmethyl-5,6-difluoro-1H-benzoimidazole To a suspension of sodium hydride (0.40 g, 10 mmol, 60%) in dry N,N-dimethylformamide (10 ml) at 25° C. was slowly added a solution of 2-(4-chloro-2-methoxy-phenyl)-5,6-difluoro-1H-benzoimidazole (1.47 g, 5 mmol) in dry N,N-dimethylformamide (5 ml), and was allowed to stir for 0.5 h. A solution of bromomethyl-cyclohexane (0.81 g, 6 mmol; CAS Reg. No. 2550-36-9) in N,N-dimethylformamide (5 ml) was then added drop wise to the above solution, and further stirred for 16 h at 25° C. The reaction mixture was quenched with saturated aqueous solution of ammonium chloride. The solvents were removed under reduced pressure. The crude material dissolved in ethyl acetate, washed with water, and then with brine, dried over sodium sulfate, filtered, and evaporated under reduced pressure. The crude product was purified by column chromatography over silica gel (20% ethyl acetate/n-hexane) to afford the title compound as a brown solid (53%). MS (Turbo Spray): m/z=391.4 (M+H).

c) 2-(4-Chloro-2-methoxy-phenyl)-5,6-difluoro-1H-benzoimidazole

To a suspension of 4-chloro-2-methoxy-benzoic acid (5 g, 0.026 mol; CAS Reg. No. 78955-90-5) in polyphosphoric acid (50 g) was added compound 4,5-difluoro-benzene-1,2-diamine (3.86 g, 0.026 mol; CAS Reg. No. 76179-40-3) and the resulting mixture was heated to 180° C. for 1 h. The reaction mixture was then cooled and neutralized with ice cold 10% aqueous sodium carbonate solution, and then extracted with ethyl acetate. The combined organic layers were dried over sodium sulfate, filtered, and evaporated under reduced pressure. The residue was purified by column chromatography over silica gel (25% ethyl acetate/n-hexane) to give the desired compound as a brown solid (77%). MS (Turbo Spray): m/z=295.1 (M+H).

Example 20

2-(4-Chloro-2-cyclopentylmethoxy-phenyl)-1-cyclohexylmethyl-5,6-difluoro-1H-benzoimidazole

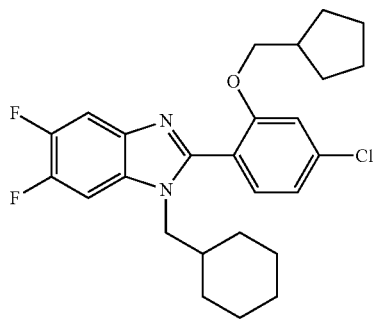

The title compound was prepared in analogy to Example 19, from 5-chloro-2-(1-cyclohexylmethyl-5,6-difluoro-1H-benzoimidazol-2-yl)-phenol (Example 19, intermediate a) and bromomethyl-cyclopentane (CAS Reg. No. 3814-30-0). Colorless powder (41%). MS (Turbo Spray): m/z=459.2 (M+H).

Example 21

2-(4-Chloro-2-cyclopropylmethoxy-phenyl)-1-cyclohexylmethyl-5,6-difluoro-1H-benzoimidazole

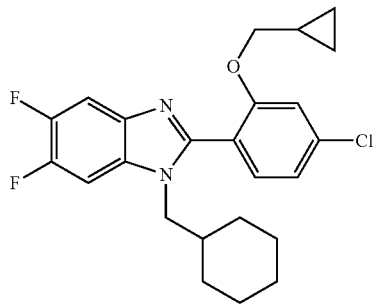

The title compound was prepared in analogy to Example 19, from 5-chloro-2-(1-cyclohexylmethyl-5,6-difluoro-1H-benzoimidazol-2-yl)-phenol (Example 19, intermediate a) and bromomethyl-cyclopropane (7051-34-5). Off-white powder (35%). MS (Turbo Spray): m/z=431.0 (M+H).

Example 22

2-(4-Chloro-2-cyclohexylmethoxy-phenyl)-1-cyclohexylmethyl-5,6-difluoro-1H-benzoimidazole

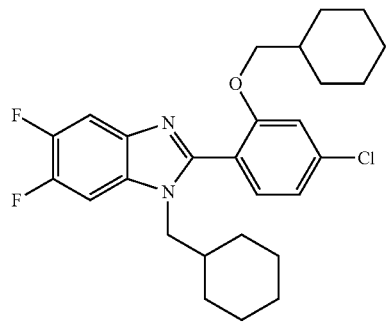

To the solution of 5-chloro-2-(1-cyclohexylmethyl-5,6-difluoro-1H-benzoimidazol-2-yl)-phenol (Example 19, intermediate a) (98 mg, 0.26 mmol) in acetone (10 ml) was added cesium carbonate (127 mg, 0.39 mmol) followed by bromomethyl-cyclohexane (42 mg, 0.31 mmol; CAS Reg. No. 2550-36-9) and the reaction was refluxed for 12 h. The reaction mixture was filtered, and the filtrate was concentrated under reduced pressure. The crude material was purified by column chromatography using silica gel (30-40% ethyl acetate/n-hexane) to afford the desired product as an off-white powder (56%). MS (Turbo Spray): m/z=473.0 (M+H).

Example 23

4-[5-Chloro-2-(1-cyclohexylmethyl-5,6-difluoro-1H-benzoimidazol-2-yl)-phenoxymethyl]-benzoic acid

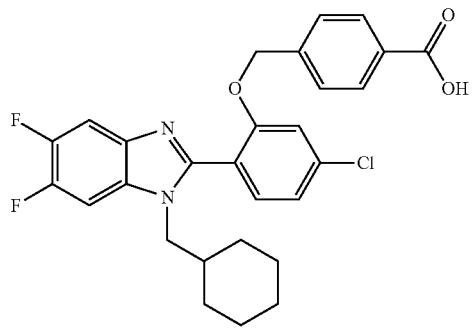

The title compound was prepared in analogy to Example 4, from 4-[5-chloro-2-(1-cyclohexylmethyl-5,6-difluoro-1H-benzoimidazol-2-yl)-phenoxymethyl]-benzoic acid methyl ester. Off-white powder (69%). MS (Turbo Spray): m/z=511.5 (M+H).

Intermediate

4-[5-Chloro-2-(1-cyclohexylmethyl-5,6-difluoro-1H-benzoimidazol-2-yl)-phenoxymethyl]-benzoic acid methyl ester The title compound was prepared in analogy to Example 19, from 5-chloro-2-(1-cyclohexylmethyl-5,6-difluoro-1H-benzoimidazol-2-yl)-phenol (Example 19, intermediate a) and 4-bromomethyl-benzoic acid methyl ester (CAS Reg. No. 2417-72-3). Brown sticky solid (90%). MS (Turbo Spray): m/z=524.0 (M+H).

Example 24

3-[5-Chloro-2-(1-cyclohexylmethyl-5,6-difluoro-1H-benzoimidazol-2-yl)-phenoxymethyl]-benzoic acid

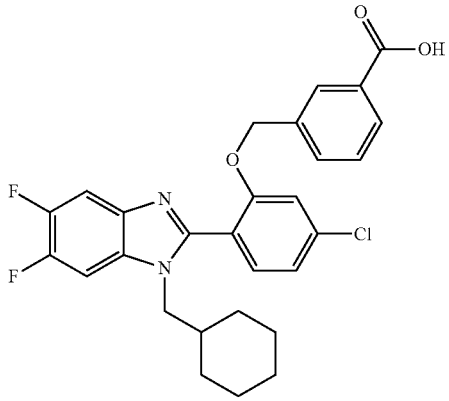

The title compound was prepared in analogy to Example 4, from 3-[5-chloro-2-(1-cyclohexylmethyl-5,6-difluoro-1H-benzoimidazol-2-yl)-phenoxymethyl]-benzoic acid methyl ester. White powder (51%). MS (Turbo Spray): m/z=511.2 (M+H).

Intermediate

3-[5-Chloro-2-(1-cyclohexylmethyl-5,6-difluoro-1H-benzoimidazol-2-yl)-phenoxymethyl]-benzoic acid methyl ester The title compound was prepared in analogy to Example 19, from 5-chloro-2-(1-cyclohexylmethyl-5,6-difluoro-1H-benzoimidazol-2-yl)-phenol (Example 19, intermediate a) and (3-bromomethyl-benzoic acid methyl ester CAS Reg. No. 1129-28-8). Brown sticky solid (90%). MS (Turbo Spray): m/z=524.0 (M+H).

Example 25

{4-[5-Chloro-2-(1-cyclohexylmethyl-5,6-difluoro-1H-benzoimidazol-2-yl)-phenoxymethyl]-phenoxy}-acetic acid

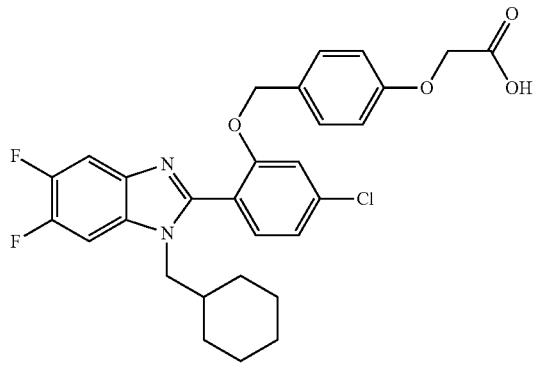

The title compound was prepared in analogy to Example 4, from {4-[5-chloro-2-(1-cyclohexylmethyl-5,6-difluoro-1H-benzoimidazol-2-yl)-phenoxymethyl]-phenoxy}-acetic acid methyl ester. White powder (52%). MS (Turbo Spray): m/z=541.2 (M+H).

Intermediate

{4-[5-Chloro-2-(1-cyclohexylmethyl-5,6-difluoro-1H-benzoimidazol-2-yl)-phenoxymethyl]-phenoxy}-acetic acid methyl ester The title compound was prepared in analogy to Example 5, intermediate a, from 5-chloro-2-(1-cyclohexylmethyl-5,6-difluoro-1H-benzoimidazol-2-yl)-phenol (Example 19, intermediate a) and (4-bromomethyl-phenoxy)-acetic acid methyl ester (CAS Reg. No. 104508-23-8). Brown sticky solid (55%). MS (Turbo Spray): m/z=555.2 (M+H).

Example 26

6-[5-Chloro-2-(1-cyclohexylmethyl-5,6-difluoro-1H-benzoimidazol-2-yl)-phenoxy]-hexanoic acid

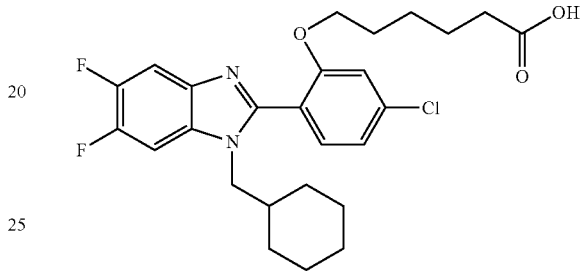

The title compound was prepared in analogy to Example 4, from 6-[5-chloro-2-(1-cyclohexylmethyl-5,6-difluoro-1H-benzoimidazol-2-yl)-phenoxy]-hexanoic acid ethyl ester. Off-white powder (59%). MS (Turbo Spray): m/z=491.3 (M+H).

Intermediate

6-[5-Chloro-2-(1-cyclohexylmethyl-5,6-difluoro-1H-benzoimidazol-2-yl)-phenoxy]-hexanoic acid ethyl ester The title compound was prepared in analogy to Example 5, intermediate a, from 5-chloro-2-(1-cyclohexylmethyl-5,6-difluoro-1H-benzoimidazol-2-yl)-phenol (Example 19, intermediate a) and (6-bromo-hexanoic acid ethyl ester CAS Reg. No. 25542-62-5). Brown sticky solid (70%). MS (Turbo Spray): m/z=519.0 (M+H).

Example 27

4-{2-[5-Chloro-2-(1-cyclohexylmethyl-5,6-difluoro-1H-benzoimidazol-2-yl)-phenoxy]-ethyl}-benzoic acid

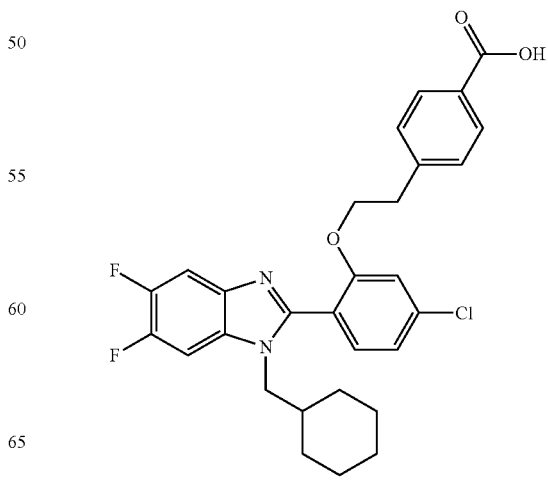

The title compound was prepared in analogy to Example 4, from 4-{2-[5-chloro-2-(1-cyclohexylmethyl-5,6-difluoro-1H-benzoimidazol-2-yl)-phenoxy]-ethyl}-benzoic acid methyl ester. Colorless powder (59%). MS (Turbo Spray): m/z=525.3 (M+H).

Intermediate

4-{2-[5-Chloro-2-(1-cyclohexylmethyl-5,6-difluoro-1H-benzoimidazol-2-yl)-phenoxy]-ethyl}-benzoic acid methyl ester The title compound was prepared in analogy to Example 5, intermediate a, from 5-chloro-2-(1-cyclohexylmethyl-5,6-difluoro-1H-benzoimidazol-2-yl)-phenol (Example 19, intermediate a) and 4-(2-bromo-ethyl)-benzoic acid methyl ester (CAS Reg. No. 136333-97-6). Colorless sticky solid (42%). MS (Turbo Spray): m/z=539.3 (M+H).

Example 28

{4-[5-Chloro-2-(1-cyclohexylmethyl-5,6-difluoro-1H-benzoimidazol-2-yl)-phenoxymethyl]-phenyl}-acetic acid

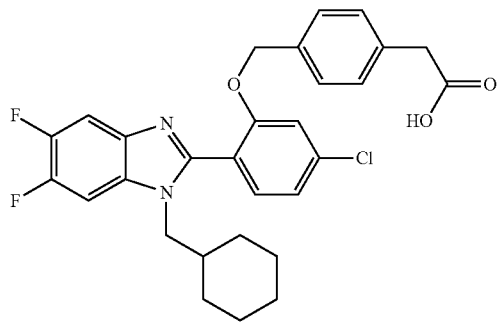

The title compound was prepared in analogy to Example 4, from {4-[5-chloro-2-(1-cyclohexylmethyl-5,6-difluoro-1H-benzoimidazol-2-yl)-phenoxymethyl]-phenyl}-acetic acid methyl ester. Colorless powder (79%). MS (Turbo Spray): m/z=525.3 (M+H).

Intermediate

{4-[5-Chloro-2-(1-cyclohexylmethyl-5,6-difluoro-1H-benzoimidazol-2-yl)-phenoxymethyl]-phenyl}-acetic acid methyl ester The title compound was prepared in analogy to Example 5, intermediate a, from 5-chloro-2-(1-cyclohexylmethyl-5,6-difluoro-1H-benzoimidazol-2-yl)-phenol (Example 19, intermediate a) and (4-bromomethyl-phenyl)-acetic acid methyl ester (7398-42-7). Brown solid (45%). MS (Turbo Spray): m/z=539.3 (M+H).

Example 29

4-[5-Chloro-2-(1-cyclohexylmethyl-5,6-difluoro-1H-benzoimidazol-2-yl)-phenoxymethyl]-cyclohexane carboxylic acid

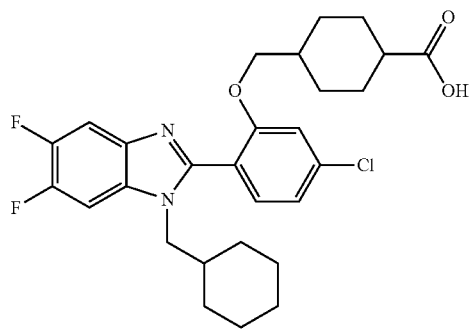

The title compound was prepared in analogy to Example 4, from 4-[5-chloro-2-(1-cyclohexylmethyl-5,6-difluoro-1H-benzoimidazol-2-yl)-phenoxymethyl]-cyclohexane carboxylic acid methyl ester. Off-white powder (32%). MS (Turbo Spray): m/z=517.4 (M+H).

Intermediates a) 4-[5-Chloro-2-(1-cyclohexylmethyl-5,6-difluoro-1H-benzoimidazol-2-yl)-phenoxymethyl]-cyclohexane carboxylic acid methyl ester The title compound was prepared in analogy to Example 5, intermediate a, from 5-chloro-2-(1-cyclohexylmethyl-5,6-difluoro-1H-benzoimidazol-2-yl)-phenol (Example 19, intermediate a) and 4-(toluene-4-sulfonyloxymethyl)-cyclohexane carboxylic acid methyl ester (CAS Reg. No. 1003013-11-3). Brown solid (51%). MS (Turbo Spray): m/z=531.4 (M+H).

b) 4-(Toluene-4-sulfonyloxymethyl)-cyclohexane carboxylic acid methyl ester

To a stirred solution of 4-hydroxymethyl-cyclohexane carboxylic acid methyl ester (300 mg, 1.74 mmol; CAS Reg. No. 13380-85-3) in dichloromethane (10 ml) under nitrogen was added triethylamine (0.5 ml, 3.48 mmol) and p-toluenesulfonyl chloride (664 mg, 3.48 mmol; CAS Reg. No. 98-59-9) at 25° C. and the mixture was stirred for 16 h. The reaction mixture was evaporated under reduced pressure, and the crude product was purified by column chromatography over silica gel (ethyl acetate/n-hexane) to give the desired compound. Colorless powder (62%). MS (Turbo Spray): m/z=327.1 (M+H).

Example 30

2-{4-Chloro-2-[3-(1H-tetrazol-5-yl)-benzyloxy]-phenyl}-1-cyclohexylmethyl-5,6-difluoro-1H-benzoimidazole

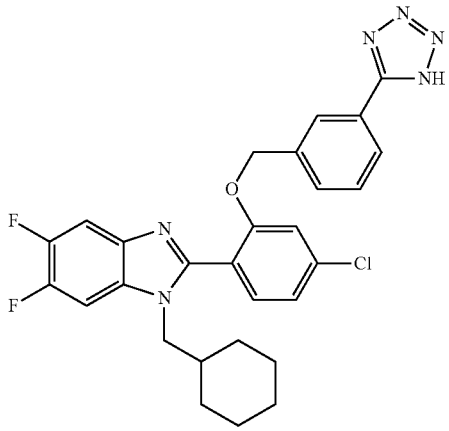

To a stirred solution of 3-[5-chloro-2-(1-cyclohexylmethyl-5,6-difluoro-1H-benzoimidazol-2-yl)-phenoxymethyl]-benzonitrile (0.15 g, 0.30 mmol) in N,N-dimethylformamide (10 ml) was added sodium azide (27 mg, 0.42 mmol) and ammonium chloride (22 mg, 0.42 mmol) and the reaction mixture was heated for 12 h at 120° C. The solvent was evaporated under reduced pressure, the residue was diluted with water and extracted with ethyl acetate. The organic layer was washed with water followed by brine, dried over sodium sulfate, filtered, and evaporated under reduced pressure. The crude product was purified by column chromatography over silica gel (4-5% methanol/dichloromethane) to yield the desired compound as a colorless powder (14%). MS (Turbo Spray): m/z=535.2 (M+H).

Intermediate

3-[5-Chloro-2-(1-cyclohexylmethyl-5,6-difluoro-1H-benzoimidazol-2-yl)-phenoxymethyl]-benzonitrile The title compound was prepared in analogy to Example 5, intermediate a, from 5-chloro-2-(1-cyclohexylmethyl-5,6-difluoro-1H-benzoimidazol-2-yl)-phenol (Example 19, intermediate a) and 3-bromomethyl-benzonitrile (CAS Reg. No. 28188-41-2). Light brown sticky solid (76%). MS (Turbo Spray): m/z=492.2 (M+H).

Example 31

2-{4-Chloro-2-[4-(1H-tetrazol-5-yl)-benzyloxy]-phenyl}-1-cyclohexylmethyl-5,6-difluoro-1H-benzoimidazole

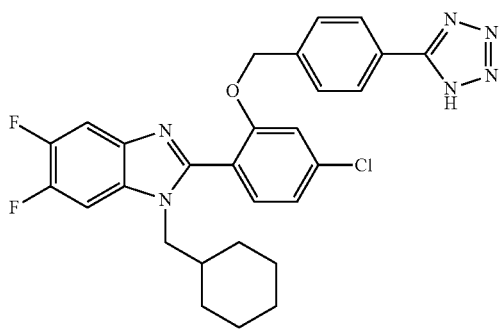

The title compound was prepared in analogy to Example 30, from 4-[5-chloro-2-(1-cyclohexylmethyl-5,6-difluoro-1H-benzoimidazol-2-yl)-phenoxymethyl]-benzonitrile. Off-white powder (31%). MS (Turbo Spray): m/z=535.3 (M+H).

Intermediate

4-[5-Chloro-2-(1-cyclohexylmethyl-5,6-difluoro-1H-benzoimidazol-2-yl)-phenoxymethyl]-benzonitrile The title compound was prepared in analogy to Example 5, intermediate a, from 5-chloro-2-(1-cyclohexylmethyl-5,6-difluoro-1H-benzoimidazol-2-yl)-phenol (Example 19, intermediate a) and 4-bromomethyl-benzonitrile (CAS Reg. No. 17201-43-3). Light brown powder (65%). MS (Turbo Spray): m/z=492.2 (M+H).

Example 32

2-{4-Chloro-2-[2-fluoro-4-(1H-tetrazol-5-yl)-benzyloxy]-phenyl}-1-cyclohexylmethyl-5,6-difluoro-1H-benzoimidazole

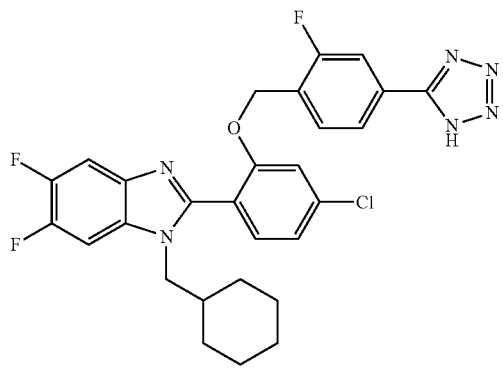

The title compound was prepared in analogy to Example 30, from 4-[5-chloro-2-(1-cyclohexylmethyl-5,6-difluoro-1H-benzoimidazol-2-yl)-phenoxymethyl]-3-fluoro-benzonitrile. Light brown powder (18%). MS (Turbo Spray): m/z=553.2 (M+H).

Intermediate

4-[5-Chloro-2-(1-cyclohexylmethyl-5,6-difluoro-1H-benzoimidazol-2-yl)-phenoxymethyl]-3-fluoro-benzonitrile The title compound was prepared in analogy to Example 5, intermediate a, from 5-chloro-2-(1-cyclohexylmethyl-5,6-difluoro-1H-benzoimidazol-2-yl)-phenol (Example 19, intermediate a) and 4-bromomethyl-3-fluoro-benzonitrile (CAS Reg. No. 105942-09-4). Light brown powder (78%). MS (Turbo Spray): m/z=510.2 (M+H).

Example 33

2-{4-Chloro-2-[3-fluoro-4-(1H-tetrazol-5-yl)-benzyloxy]-phenyl}-1-cyclohexylmethyl-5,6-difluoro-1H-benzoimidazole

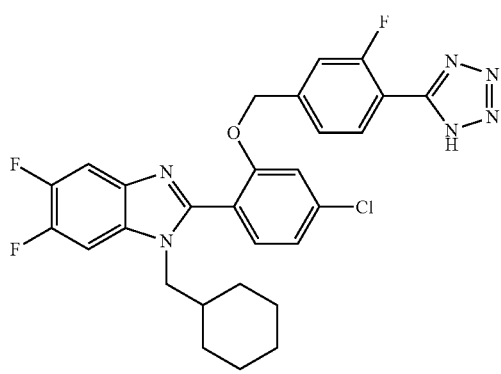

The title compound was prepared in analogy to Example 30, from 4-[5-chloro-2-(1-cyclohexylmethyl-5,6-difluoro-1H-benzoimidazol-2-yl)-phenoxymethyl]-2-fluoro-benzonitrile. Yellow powder (8%). MS (Turbo Spray): m/z=553.0 (M+H).

Intermediate

4-[5-Chloro-2-(1-cyclohexylmethyl-5,6-difluoro-1H-benzoimidazol-2-yl)-phenoxymethyl]-2-fluoro-benzonitrile The title compound was prepared in analogy to Example 5, intermediate a, from 5-chloro-2-(1-cyclohexylmethyl-5,6-difluoro-1H-benzoimidazol-2-yl)-phenol (Example 19, intermediate a) and 4-bromomethyl-2-fluoro-benzonitrile (CAS Reg. No. 222978-03-2). Off-white powder (89%). MS (Turbo Spray): m/z=510.3 (M+H).

Example 34

1-Cyclohexylmethyl-5,6-difluoro-2-{2-[2-fluoro-4-(1H-tetrazol-5-yl)-benzyloxy]-phenyl}-1H-benzoimidazole

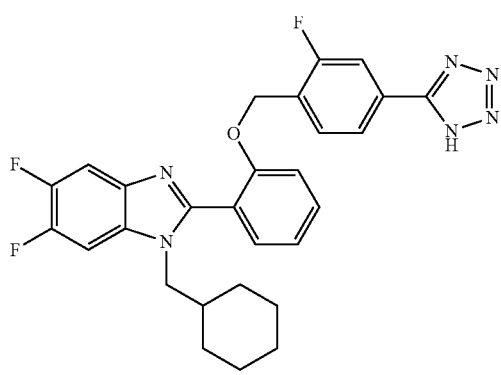

The title compound was prepared in analogy to Example 30, from 4-[2-(1-cyclohexylmethyl-5,6-difluoro-1H-benzoimidazol-2-yl)-phenoxymethyl]-3-fluoro-benzonitrile. Off-white powder (35%). MS (Turbo Spray): m/z=519.4 (M+H).

Intermediates a) 4-[2-(1-Cyclohexylmethyl-5,6-difluoro-1H-benzoimidazol-2-yl)-phenoxymethyl]-3-fluoro-benzonitrile The title compound was prepared in analogy to Example 5, intermediate a, from 2-(1-cyclohexylmethyl-5,6-difluoro-1H-benzoimidazol-2-yl)-phenol and 4-bromomethyl-3-fluoro-benzonitrile (105942-09-4). Brown sticky solid (69%). MS (Turbo Spray): m/z=476.4 (M+H).

b) 2-(1-Cyclohexylmethyl-5,6-difluoro-1H-benzoimidazol-2-yl)-phenol

The title compound was prepared in analogy to Example 19, intermediate a, from 1-cyclohexylmethyl-5,6-difluoro-2-(2-methoxy-phenyl)-1H-benzoimidazole. Colorless solid (62%). MS (Turbo Spray): m/z=343.2 (M+H).

c) 1-Cyclohexylmethyl-5,6-difluoro-2-(2-methoxy-phenyl)-1H-benzoimidazole

The title compound was prepared in analogy to Example 19, intermediate b, from 5,6-difluoro-2-(2-methoxy-phenyl)-1H-benzoimidazole and bromomethyl-cyclohexane (2550-36-9). Brown sticky solid (42%). MS (Turbo Spray): m/z=357.4 (M+H).

d) 5,6-Difluoro-2-(2-methoxy-phenyl)-1H-benzoimidazole

The title compound was prepared in analogy to Example 19, intermediate c, from 4,5-difluoro-benzene-1,2-diamine (CAS Reg. No. 76179-40-3) and 2-methoxy-benzoic acid (CAS Reg. No. 579-75-9). Brown solid (41%). MS (Turbo Spray): m/z=261.2 (M+H).

Example 35

2-{4-Chloro-2-[2-methoxy-4-(1H-tetrazol-5-yl)-benzyloxy]-phenyl}-1-cyclohexylmethyl-5,6-difluoro-1H-benzoimidazole

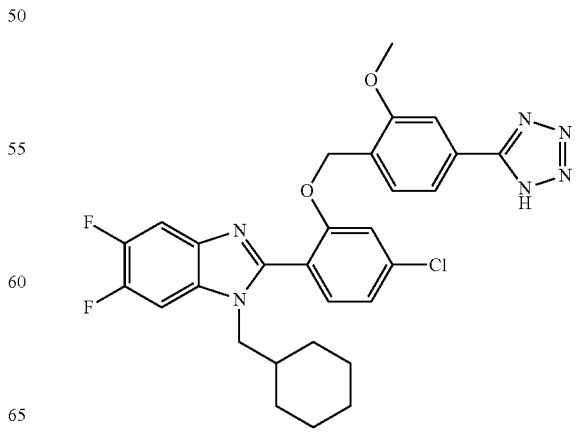

The title compound was prepared in analogy to Example 30, from 4-[5-chloro-2-(1-cyclohexylmethyl-5,6-difluoro-1H-benzoimidazol-2-yl)-phenoxymethyl]-3-methoxy-benzonitrile. Off-white powder (23%). MS (Turbo Spray): m/z=565.2 (M+H).

Intermediate

4-[5-Chloro-2-(1-cyclohexylmethyl-5,6-difluoro-1H-benzoimidazol-2-yl)-phenoxymethyl]-3-methoxy-benzonitrile The title compound was prepared in analogy to Example 19, from 2-(1-cyclohexylmethyl-5,6-difluoro-1H-benzoimidazol-2-yl)-phenol (Example 19, intermediate a) and 4-bromomethyl-3-methoxy-benzonitrile (CAS Reg. No. 104436-60-4). Brown sticky solid (83%). MS (Turbo Spray): m/z=522.2 (M+H).

Example 36

2-(4-Chloro-2-{2-[4-(1H-tetrazol-5-yl)-phenyl]-ethoxy}-phenyl)-1-cyclohexylmethyl-5,6-difluoro-1H-benzoimidazole

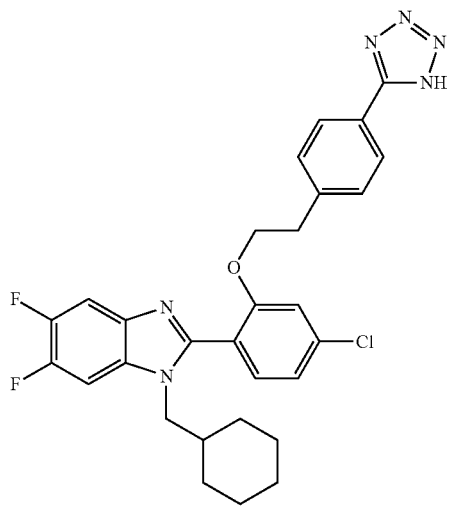

The title compound was prepared in analogy to Example 30, from 4-{2-[5-chloro-2-(1-cyclohexylmethyl-5,6-difluoro-1H-benzoimidazol-2-yl)-phenoxy]-ethyl}-benzonitrile. Off-white powder (42%). MS (Turbo Spray): m/z=549.2 (M+H).

Intermediate

4-{2-[5-Chloro-2-(1-cyclohexylmethyl-5,6-difluoro-1H-benzoimidazol-2-yl)-phenoxy]-ethyl}-benzonitrile The title compound was prepared in analogy to Example 19, from 2-(1-cyclohexylmethyl-5,6-difluoro-1H-benzoimidazol-2-yl)-phenol (Example 19, intermediate a) and 4-(2-bromo-ethyl)-benzonitrile (CAS Reg. No. 72054-56-9). Brown solid (51%). MS (Turbo Spray): m/z=506.2 (M+H).

Example 37

2-{4-Chloro-2-[5-(1H-tetrazol-5-yl)-thiophen-2-ylmethoxy]-phenyl}-1-cyclohexylmethyl-5,6-difluoro-1H-benzoimidazole

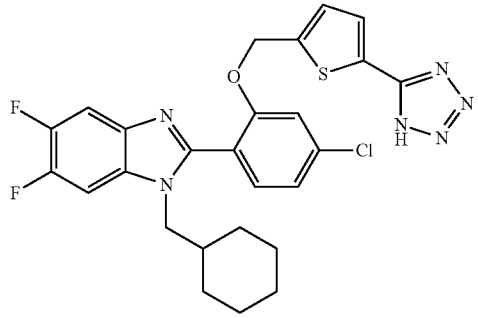

The title compound was prepared in analogy to Example 30, from 5-[5-chloro-2-(1-cyclohexylmethyl-5,6-difluoro-1H-benzoimidazol-2-yl)-phenoxymethyl]-thiophene-2-carbonitrile. Off-white powder (14%). MS (Turbo Spray): m/z=541.2 (M+H).

Intermediate

5-[5-Chloro-2-(1-cyclohexylmethyl-5,6-difluoro-1H-benzoimidazol-2-yl)-phenoxymethyl]-thiophene-2-carbonitrile The title compound was prepared in analogy to Example 19, from 2-(1-cyclohexylmethyl-5,6-difluoro-1H-benzoimidazol-2-yl)-phenol (Example 19, intermediate a) and (5-bromomethyl-thiophene-2-carbonitrile (CAS Reg. No. 134135-41-4). Brown solid (91%). MS (Turbo Spray): m/z=498.0 (M+H).

Example 38

2-{4-Chloro-2-[4-(1H-tetrazol-5-yl)-2-trifluoromethyl-benzyloxy]-phenyl}-1-cyclohexylmethyl-5,6-difluoro-1H-benzoimidazole

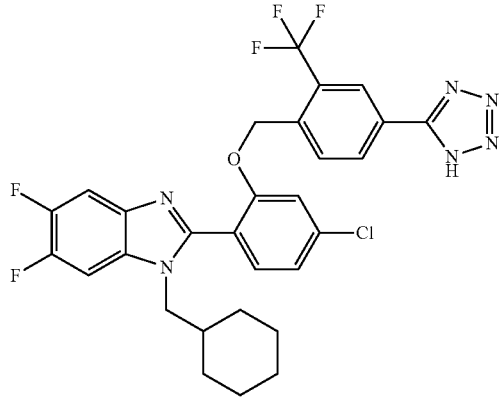

The title compound was prepared in analogy to Example 30, from 4-[5-chloro-2-(1-cyclohexylmethyl-5,6-difluoro-1H-benzoimidazol-2-yl)-phenoxymethyl]-3-trifluoromethyl-benzonitrile. Off-white powder (37%). MS (Turbo Spray): m/z=603.2 (M+H).

Intermediate

4-[5-Chloro-2-(1-cyclohexylmethyl-5,6-difluoro-1H-benzoimidazol-2-yl)-phenoxymethyl]-3-trifluoromethyl-benzonitrile The title compound was prepared in analogy to Example 19, from 2-(1-cyclohexylmethyl-5,6-difluoro-1H-benzoimidazol-2-yl)-phenol (Example 19, intermediate a) and 4-bromomethyl-3-trifluoromethyl-benzonitrile (CAS Reg. No. 853368-32-8). Brown sticky solid (96%). MS (Turbo Spray): m/z=560.0 (M+H).

Example 39

2-{4-Chloro-2-[2-fluoro-4-(1H-tetrazol-5-yl)-benzyloxy]-phenyl}-1-cyclohexylmethyl-1H-benzoimidazole

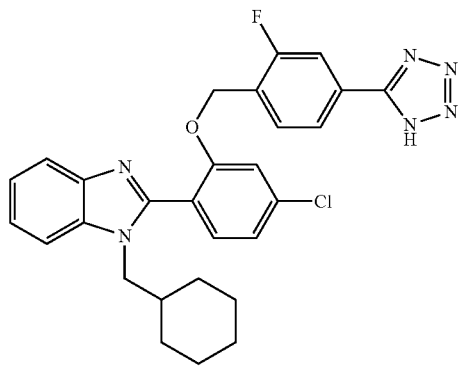

The title compound was prepared in analogy to Example 30, from 4-[5-chloro-2-(1-cyclohexylmethyl-1H-benzoimidazol-2-yl)-phenoxymethyl]-3-fluoro-benzonitrile. Colorless powder (37%). MS (Turbo Spray): m/z=517.4 (M+H).

Intermediates a) 4-[5-Chloro-2-(1-cyclohexylmethyl-1H-benzoimidazol-2-yl)-phenoxymethyl]-3-fluoro-benzonitrile The title compound was prepared in analogy to Example 19, from 5-chloro-2-(1-cyclohexylmethyl-1H-benzoimidazol-2-yl)-phenol and 4-bromomethyl-3-fluoro-benzonitrile (105942-09-4). Brown solid (69%). MS (Turbo Spray): m/z=474.4 (M+H).

b) 5-Chloro-2-(1-cyclohexylmethyl-1H-benzoimidazol-2-yl)-phenol

The title compound was prepared in analogy to Example 19, intermediate a, from 2-(4-chloro-2-methoxy-phenyl)-1-cyclohexylmethyl-1H-benzoimidazole. Colorless powder (66%). MS (Turbo Spray): m/z=341.0 (M+H).

c) 2-(4-Chloro-2-methoxy-phenyl)-1-cyclohexylmethyl-1H-benzoimidazole

The title compound was prepared in analogy to Example 19, intermediate b, from 2-(4-Chloro-2-methoxy-phenyl)-1H-benzoimidazole and bromomethyl-cyclohexane (CAS Reg. No 2550-36-9). Brown solid (48%). MS (Turbo Spray): m/z=355.3 (M+H).

d) 2-(4-Chloro-2-methoxy-phenyl)-1H-benzoimidazole

The title compound was prepared in analogy to Example 19, intermediate c, from benzene-1,2-diamine (CAS Reg. No. 95-54-5) and 4-chloro-2-methoxy-benzoic acid (CAS Reg. No. 57479-70-6). Colorless powder (59%). MS (Turbo Spray): m/z=259.4 (M+H).

Example 40

1-Cyclohexylmethyl-5,6-difluoro-2-{2-[2-fluoro-4-(1H-tetrazol-5-yl)-phenoxymethyl]-phenyl}-1H-benzoimidazole

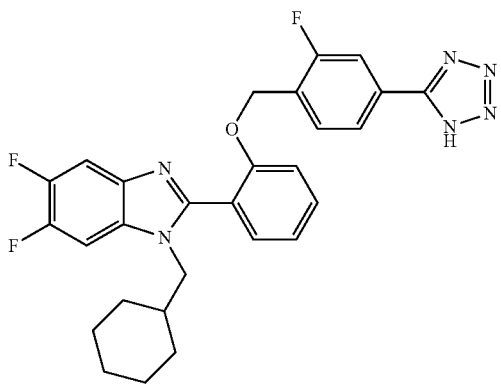

The compound was prepared in analogy to Example 30, from 4-[2-(1-cyclohexylmethyl-5,6-difluoro-1H-benzoimidazol-2-yl)-benzyloxy]-3-fluoro-benzonitrile. Yellow powder (61%). MS (Turbo Spray): m/z=519.0 (M+H).

Intermediates a) 4-[2-(1-Cyclohexylmethyl-5,6-difluoro-1H-benzoimidazol-2-yl)-benzyloxy]-3-fluoro-benzonitrile The compound was prepared in analogy to Example 19, intermediate b, from 4-[2-(5,6-difluoro-1H-benzoimidazol-2-yl)-benzyloxy]-3-fluoro-benzonitrile and bromomethyl-cyclohexane (CAS Reg. No. 2550-36-9). Yellow powder (69%). MS (Turbo Spray): m/z=476.4 (M+H).

b) 4-[2-(5,6-Difluoro-1H-benzoimidazol-2-yl)-benzyloxy]-3-fluoro-benzonitrile

To a mixture of 4,5-difluoro-benzene-1,2-diamine (501 mg, 3.47 mmol; CAS Reg. No. 76179-40-3) and triethylamine (0.64 ml, 4.74 mmol) in dichloromethane (10 ml) at 0° C. was added a solution of 2-(4-cyano-2-fluoro-phenoxymethyl)-benzoyl chloride (1.06 g, 3.65 mmol) in dichloromethane (15 ml) drop wise over 10 minutes. After stirring for 3 h at 0° C. the volatiles were removed in vacuo to give a yellow solid. The solid was dissolved in glacial acetic acid (15 ml), and sodium acetate was added to the solution, and the mixture was refluxed for 13 h. The reaction mixture was cooled to 25° C., evaporated in vacuo, and partitioned between dichloromethane and water. The biphasic mixture was cooled in an ice bath, and neutralized with solid potassium carbonate while maintaining vigorous stirring. The phases were separated, and the extraction was completed with additional portions of dichloromethane. The combined organic extracts were dried over sodium sulfate, filtered, and evaporated under reduced pressure. The crude product was purified by flash chromatography over silica gel (15% ethyl acetate/n-hexane) to yield the desired compound as a brown solid (16%). MS (Turbo Spray): m/z=380.4 (M+H).

c) 2-(4-Cyano-2-fluoro-phenoxymethyl)-benzoyl chloride

To a suspension of 2-(4-cyano-2-fluoro-phenoxymethyl)-benzoic acid (1.0 g, 3.68 mmol) in dichloromethane (15 ml) was added oxalyl chloride (0.45 ml, 4.79 mmol), followed by a drop of N,N-dimethylformamide, and stirred for 12 h at 25° C. The resulting clear solution was evaporated in vacuo and the crude product was used in the next step without any further purification (99%). MS (Turbo Spray): m/z=290.1 (M+H).

d) 2-(4-Cyano-2-fluoro-phenoxymethyl)-benzoic acid

To a solution of 2-(4-cyano-2-fluoro-phenoxymethyl)-benzoic acid methyl ester (2.17 g, 7.6 mmol) in tetrahydrofuran (30 ml) was added a solution of lithium hydroxide monohydrate (1.59 g, 38.03 mmol) in water (30 ml) and the resulting mixture was allowed to stir at 25° C. for 12 h. The solvent was removed in vacuo, the residue was diluted with water (20 ml), washed with diethyl ether (2×15 ml). The aqueous layer was then acidified to pH 5 with 2N aqueous hydrochloric acid and extracted with ethyl acetate (2×40 ml). The combined organic layers were washed with water (2×25 ml), brine, dried over sodium sulfate, filtered, and evaporated to afford the desired compound as a colorless solid (90%). MS (Turbo Spray): m/z=272.1 (M+H).

e) 2-(4-Cyano-2-fluoro-phenoxymethyl)-benzoic acid methyl ester

To a solution of 3-fluoro-4-hydroxy-benzonitrile (1.2 g, 8.7 mmol; CAS Reg. No. 405-04-9) in acetone (20 ml) was added cesium carbonate (4.2 g, 13.05 mmol) and 2-bromomethyl-benzoic acid methyl ester (2 g, 8.7 mmol; CAS Reg. No. 2417-73-4) and the resulting solution was heated to reflux for 12 h. The reaction mixture was filtered and evaporated in vacuo. The residue was purified by column chromatography over silica gel (8-10% ethyl acetate/n-hexane) to give the desired product as a yellow sticky solid (90%). MS (Turbo Spray): m/z=286.1 (M+H).

Example 41

1-Cyclohexylmethyl-5,6-difluoro-2-{2-[3-fluoro-4-(1H-tetrazol-5-yl)-phenoxymethyl]-phenyl}-1H-benzoimidazole

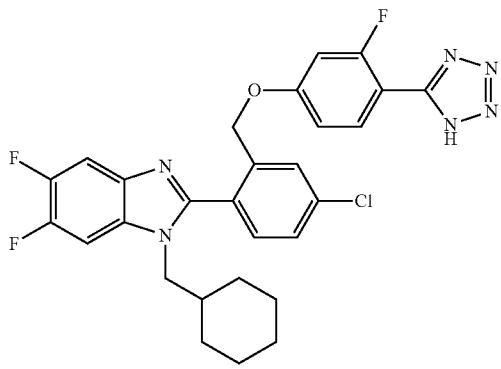

The title compound was prepared in analogy to Example 30, from 4-[2-(1-cyclohexylmethyl-5,6-difluoro-1H-benzoimidazol-2-yl)-benzyloxy]-2-fluoro-benzonitrile. Off-white powder (52%). MS (Turbo Spray): m/z=519.4 (M+H).

Intermediates a) 4-[2-(1-Cyclohexylmethyl-5,6-difluoro-1H-benzoimidazol-2-yl)-benzyloxy]-2-fluoro-benzonitrile The title compound was prepared in analogy to Example 19, intermediate b, from 4-[2-(5,6-difluoro-1H-benzoimidazol-2-yl)-benzyloxy]-2-fluoro-benzonitrile and bromomethyl-cyclohexane (CAS Reg. No. 2550-36-9). Light yellow solid (58%). MS (Turbo Spray): m/z=476.1 (M+H).

b) 4-[2-(5,6-difluoro-1H-benzoimidazol-2-yl)-benzyloxy]-2-fluoro-benzonitrile The title compound was prepared in analogy to Example 40, intermediate b, from 2-(4-cyano-3-fluoro-phenoxymethyl)-benzoyl chloride and 4,5-difluoro-benzene-1,2-diamine (CAS Reg. No. 76179-40-3). Light yellow solid (15%). MS (Turbo Spray): m/z=380.2 (M+H).

c) 2-(4-Cyano-3-fluoro-phenoxymethyl)-benzoyl chloride

The title compound was prepared in analogy to Example 40, intermediate c, from 2-(4-cyano-3-fluoro-phenoxymethyl)-benzoic acid. The so-obtained crude yellow liquid was used in the next step without any further purification. MS (Turbo Spray): m/z=290.0 (M+H).

d) 2-(4-Cyano-3-fluoro-phenoxymethyl)-benzoic acid

The title compound was prepared in analogy to Example 40, intermediate d, from 2-(4-cyano-3-fluoro-phenoxymethyl)-benzoic acid methyl ester. Off-white solid (80%). MS (Turbo Spray): m/z=272.2 (M+H).

e) 2-(4-Cyano-3-fluoro-phenoxymethyl)-benzoic acid methyl ester

The title compound was prepared in analogy to Example 40, intermediate e, from 2-fluoro-4-hydroxy-benzonitrile (CAS Reg. No. 82380-18-5) and 2-bromomethyl-benzoic acid methyl ester (CAS Reg. No. 2417-73-4). Off-white solid (91%). MS (Turbo Spray): m/z=286.1 (M+H).

Example 42

2-{4-Chloro-2-[2-fluoro-4-(1H-tetrazol-5-yl)-benzyloxy]-phenyl}-1-cyclopentylmethyl-5,6-difluoro-1H-benzoimidazole

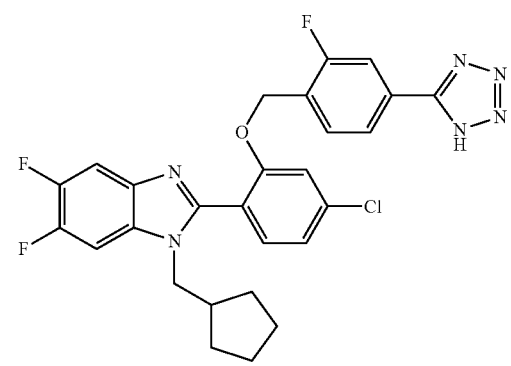

The title compound was prepared in analogy to Example 30, from 4-[5-chloro-2-(1-cyclopentylmethyl-5,6-difluoro- 1H-benzoimidazol-2-yl)-phenoxymethyl]-3-fluoro-benzonitrile. Off-white powder (31%). MS (Turbo Spray): m/z=539.2 (M+H).

Intermediates a) 4-[5-Chloro-2-(1-cyclopentylmethyl-5,6-difluoro-1H-benzoimidazol-2-yl)-phenoxymethyl]-3-fluoro-benzonitrile The title compound was prepared in analogy to Example 5, intermediate a, from 5-chloro-2-(1-cyclopentylmethyl-5,6-difluoro-1H-benzoimidazol-2-yl)-phenol and 4-bromomethyl-3-fluoro-benzonitrile (CAS Reg. No. 105942-09-4). Brown solid (95%). MS (Turbo Spray): m/z=496.4 (M+H).

b) 5-Chloro-2-(1-cyclopentylmethyl-5,6-difluoro-1H-benzoimidazol-2-yl)-phenol

The title compound was prepared in analogy to Example 19, intermediate a, from 2-(4-chloro-2-methoxy-phenyl)-1-cyclopentylmethyl-5,6-difluoro-1H-benzoimidazole. Off-white solid (52%). MS (Turbo Spray): m/z=363.4 (M+H).

c) 2-(4-Chloro-2-methoxy-phenyl)-1-cyclopentylmethyl-5,6-difluoro-1H-benzoimidazole The title compound was prepared in analogy to Example 19, intermediate b, from 2-(4-chloro-2-methoxy-phenyl)-5,6-difluoro-1H-benzoimidazole (Example 19, intermediate c) and iodomethyl-cyclopentane (CAS Reg. No. 27935-87-1). Brown sticky solid (50%). MS (Turbo Spray): m/z=377.1 (M+H).

Example 43

2-{4-Chloro-2-[2-fluoro-4-(1H-tetrazol-5-yl)-benzyloxy]-phenyl}-1-(2-cyclohexyl-ethyl)-5,6-difluoro-1H-benzoimidazole

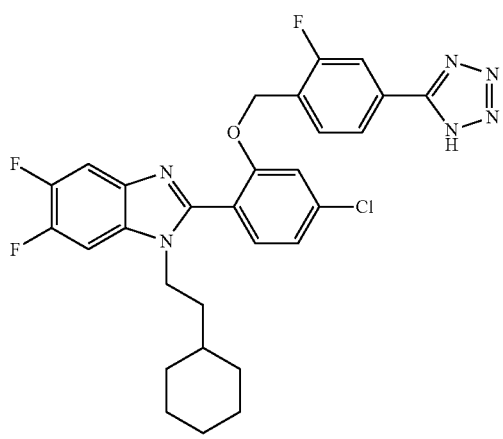

The title compound was prepared in analogy to Example 30, from 4-{5-chloro-2-[1-(2-cyclohexyl-ethyl)-5,6-difluoro-1H-benzoimidazol-2-yl]-phenoxymethyl}-3-fluoro-benzonitrile. Colorless powder (22%). MS (Turbo Spray): m/z=567.4 (M+H).

Intermediates a) 4-{5-Chloro-2-[1-(2-cyclohexyl-ethyl)-5,6-difluoro-1H-benzoimidazol-2-yl]-phenoxymethyl}-3-fluoro-benzonitrile The title compound was prepared in analogy to Example 5, intermediate a, from 5-chloro-2-[1-(2-cyclohexyl-ethyl)-5,6-difluoro-1H-benzoimidazol-2-yl]-phenol and 4-bromomethyl-3-fluoro-benzonitrile (CAS Reg. No. 105942-09-4). Brown sticky solid (81%). MS (Turbo Spray): m/z=524.0 (M+H).

b) 5-Chloro-2-[1-(2-cyclohexyl-ethyl)-5,6-difluoro-1H-benzoimidazol-2-yl]-phenol The title compound was prepared in analogy to Example 19, intermediate a, from 2-(4-chloro-2-methoxy-phenyl)-1-(2-cyclohexyl-ethyl)-5,6-difluoro-1H-benzoimidazole. Colorless powder (72%). MS (Turbo Spray): m/z=391.3 (M+H).

c) 2-(4-Chloro-2-methoxy-phenyl)-1-(2-cyclohexyl-ethyl)-5,6-difluoro-1H-benzoimidazole The title compound was prepared in analogy to Example 19, intermediate b, from 2-(4-chloro-2-methoxy-phenyl)-5,6-difluoro-1H-benzoimidazole (Example 19, intermediate c) and (2-bromo-ethyl)-cyclohexane (CAS Reg. No. 1647-26-3). Brown sticky solid (73%). MS (Turbo Spray): m/z=405.0 (M+H).

Example 44

2-{4-Chloro-2-[2-fluoro-4-(1H-tetrazol-5-yl)-benzyloxy]-phenyl}-5,6-difluoro-1-pentyl-1H-benzoimidazole

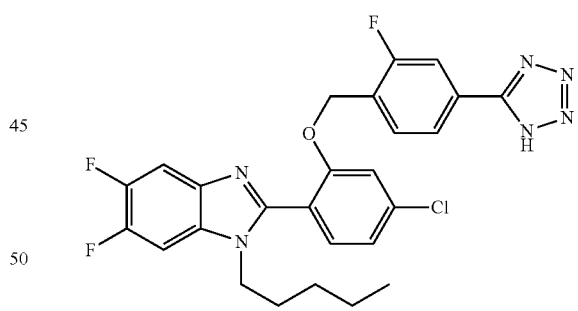

The title compound was prepared in analogy to Example 30, from 4-[5-chloro-2-(5,6-difluoro-1-pentyl-1H-benzoimidazol-2-yl)-phenoxymethyl]-3-fluoro-benzonitrile. Brown powder (10%). MS (Turbo Spray): m/z=527.4 (M+H).

Intermediates a) 4-[5-Chloro-2-(5,6-difluoro-1-pentyl-1H-benzoimidazol-2-yl)-phenoxymethyl]-3-fluoro-benzonitrile The title compound was prepared in analogy to Example 5, intermediate a, from 5-chloro-2-(5,6-difluoro-1-pentyl-1H-benzoimidazol-2-yl)-phenol and 4-bromomethyl-3-fluorobenzonitrile (CAS Reg. No. 105942-09-4). Brown powder (41%). MS (Turbo Spray): m/z=484.4 (M+H).

b) 5-Chloro-2-(5,6-difluoro-1-pentyl-1H-benzoimidazol-2-yl)-phenol

The title compound was prepared in analogy to Example 19, intermediate a, from 2-(4-chloro-2-methoxy-phenyl)-5,6-difluoro-1-pentyl-1H-benzoimidazole. Off-white powder (33%). MS (Turbo Spray): m/z=351.4 (M+H).

c) 2-(4-Chloro-2-methoxy-phenyl)-5,6-difluoro-1-pentyl-1H-benzoimidazole

The title compound was prepared in analogy to Example 19, intermediate b, from 2-(4-chloro-2-methoxy-phenyl)-5,6-difluoro-1H-benzoimidazole (Example 19, intermediate c) and 1-bromo-pentane (CAS Reg. No. 10-53-2). Brown powder (81%). MS (Turbo Spray): m/z=364.8 (M+H).

Example 45

2-{4-Chloro-2-[2-fluoro-4-(1H-tetrazol-5-yl)-benzyloxy]-phenyl}-5,6-difluoro-1-(tetrahydro-pyran-2-ylmethyl)-1H-benzoimidazole

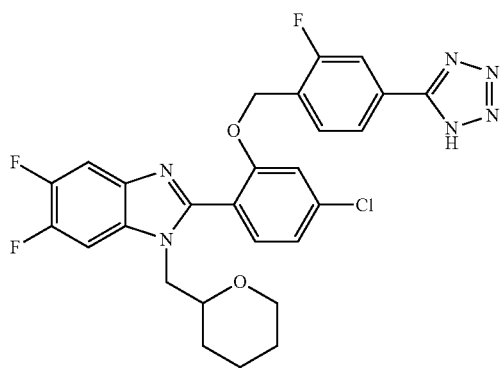

The title compound was prepared in analogy to Example 30, from 4-{5-chloro-2-[5,6-difluoro-1-(tetrahydro-pyran-2-ylmethyl)-1H-benzoimidazol-2-yl]-phenoxymethyl}-3-fluoro-benzonitrile. Off-white powder (43%). MS (Turbo Spray): m/z=555.1 (M+H).

Intermediates a) 4-{5-Chloro-2-[5,6-difluoro-1-(tetrahydro-pyran-2-ylmethyl)-1H-benzoimidazol-2-yl]-phenoxymethyl}-3-fluoro-benzonitrile The title compound was prepared in analogy to Example 5, intermediate a, from 5-chloro-2-[5,6-difluoro-1-(tetrahydro-pyran-2-ylmethyl)-1H-benzoimidazol-2-yl]-phenol and 4-bromomethyl-3-fluoro-benzonitrile (CAS Reg. No. 105942-09-4). Brown powder (32%). MS (Turbo Spray): m/z=512.4 (M+H).

b) 5-Chloro-2-[5,6-difluoro-1-(tetrahydro-pyran-2-ylmethyl)-1H-benzoimidazol-2-yl]-phenol The title compound was prepared in analogy to Example 19, intermediate a, from 2-(4-chloro-2-methoxy-phenyl)-5,6-difluoro-1-(tetrahydro-pyran-2-ylmethyl)-1H-benzoimidazole. Off-white powder (66%). MS (Turbo Spray): m/z=379.2 (M+H).

c) 2-(4-Chloro-2-methoxy-phenyl)-5,6-difluoro-1-(tetrahydro-pyran-2-ylmethyl)-1H-benzoimidazole The title compound was prepared in analogy to Example 19, intermediate b, from 2-(4-chloro-2-methoxy-phenyl)-5,6-difluoro-1H-benzoimidazole (Example 19, intermediate c) and 2-bromomethyl-tetrahydro-pyran (CAS Reg. No. 34723-82-5). Brown powder (39%). MS (Turbo Spray): m/z=393.2 (M+H).

Example 46

2-{4-Chloro-2-[2-fluoro-4-(1H-tetrazol-5-yl)-benzyloxy]-phenyl}-1-(2,2-dimethyl-propyl)-5,6-difluoro-1H-benzoimidazole

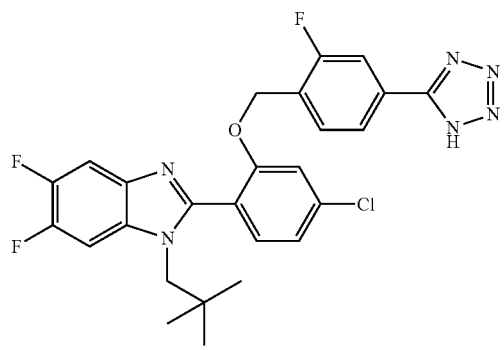

The title compound was prepared in analogy to Example 30, from 4-{5-chloro-2-[1-(2,2-dimethyl-propyl)-5,6-difluoro-1H-benzoimidazol-2-yl]-phenoxymethyl}-3-fluoro-benzonitrile. Light brown solid (31%). MS (Turbo Spray): m/z=526.6 (M+H).

Intermediates a) 4-{5-Chloro-2-[1-(2,2-dimethyl-propyl)-5,6-difluoro-1H-benzoimidazol-2-yl]-phenoxymethyl}-3-fluoro-benzonitrile The title compound was prepared in analogy to Example 5, intermediate a, from 5-chloro-2-[1-(2,2-dimethyl-propyl)-5,6-difluoro-1H-benzoimidazol-2-yl]-phenol and 4-bromomethyl-3-fluoro-benzonitrile (CAS Reg. No. 105942-09-4). Light brown solid (95%). MS (Turbo Spray): m/z=483.8 (M+H).

b) 5-Chloro-2-[1-(2,2-dimethyl-propyl)-5,6-difluoro-1H-benzoimidazol-2-yl]-phenol The title compound was prepared in analogy to Example 19, intermediate a, from 2-(4-chloro-2-methoxy-phenyl)-1-(2,2-dimethyl-propyl)-5,6-difluoro-1H-benzoimidazole. Colorless powder (36%). MS (Turbo Spray): m/z=351.2 (M+H).

c) 2-(4-Chloro-2-methoxy-phenyl)-1-(2,2-dimethyl-propyl)-5,6-difluoro-1H-benzoimidazole The title compound was prepared in analogy to Example 19, intermediate b, from 2-(4-chloro-2-methoxy-phenyl)-5, 6-difluoro-1H-benzoimidazole (Example 19, intermediate c) and 1-bromo-2,2-dimethyl-propane (CAS Reg. No. 630-17-1). Light brown solid (20%). MS (Turbo Spray): m/z=365.1 (M+H).

Example 47

2-{4-Chloro-2-[2-fluoro-4-(1H-tetrazol-5-yl)-benzyloxy]-phenyl}-5,6-difluoro-1-(tetrahydro-pyran-4-ylmethyl)-1H-benzoimidazole

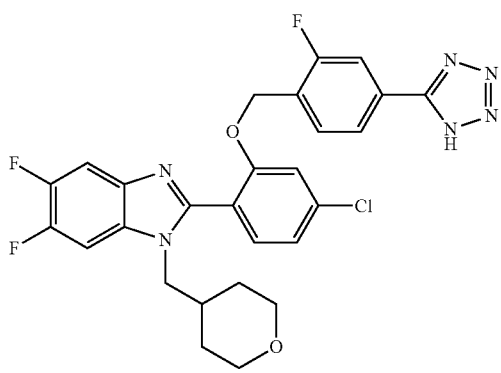

The title compound was prepared in analogy to Example 30, from 4-{5-chloro-2-[5,6-difluoro-1-(tetrahydro-pyran-4-ylmethyl)-1H-benzoimidazol-2-yl]-phenoxymethyl}-3-fluoro-benzonitrile. Colorless powder (38%). MS (Turbo Spray): m/z=555.0 (M+H).

Intermediates a) 4-{5-Chloro-2-[5,6-difluoro-1-(tetrahydro-pyran-4-ylmethyl)-1H-benzoimidazol-2-yl]-phenoxymethyl}-3-fluoro-benzonitrile The title compound was prepared in analogy to Example 5, intermediate a, from 5-chloro-2-[5,6-difluoro-1-(tetrahydro-pyran-4-ylmethyl)-1H-benzoimidazol-2-yl]-phenol and 4-bromomethyl-3-fluoro-benzonitrile (CAS Reg. No. 105942-09-4). Light brown solid (95%). MS (Turbo Spray): m/z=511.9 (M+H).

b) 5-Chloro-2-[5,6-difluoro-1-(tetrahydro-pyran-4-ylmethyl)-1H-benzoimidazol-2-yl]-phenol The title compound was prepared in analogy to Example 19, intermediate a, from 2-(4-chloro-2-methoxy-phenyl)-5,6-difluoro-1-(tetrahydro-pyran-4-ylmethyl)-1H-benzoimidazole. Colorless powder (48%). MS (Turbo Spray): m/z=379.2 (M+H).

c) 2-(4-Chloro-2-methoxy-phenyl)-5,6-difluoro-1-(tetrahydro-pyran-4-ylmethyl)-1H-benzoimidazole The title compound was prepared in analogy to Example 19, intermediate b, from 2-(4-chloro-2-methoxy-phenyl)-5,6-difluoro-1H-benzoimidazole (Example 19, intermediate c) and 4-bromomethyl-tetrahydro-pyran (CAS Reg. No. 125552-89-8). Light brown solid (29%). MS (Turbo Spray): m/z=393.3 (M+H).

Example 48

1-Benzyl-2-[4-chloro-2-(2-chloro-benzyloxy)-phenyl]-5,6-difluoro-1H-benzoimidazole

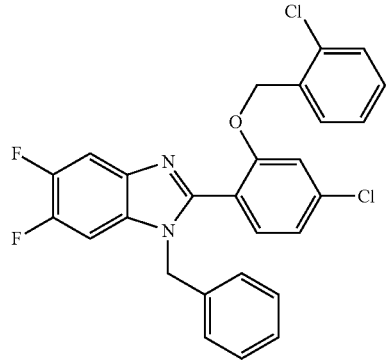

The title compound was prepared in analogy to Example 19, from 2-(1-benzyl-5,6-difluoro-1H-benzoimidazol-2-yl)-5-chloro-phenol and 1-bromomethyl-3-chloro-benzene (CAS Reg. No. 766-80-3). Colorless powder (84%). MS (Turbo Spray): m/z=494.8 (M+H).

Intermediates a) 2-(1-Benzyl-5,6-difluoro-1H-benzoimidazol-2-yl)-5-chloro-phenol The title compound was prepared in analogy to Example 19, intermediate a, from 1-benzyl-2-(4-chloro-2-methoxy-phenyl)-5,6-difluoro-1H-benzoimidazole. Colorless powder (90%). MS (Turbo Spray): m/z=370.9 (M+H).

b) 1-Benzyl-2-(4-chloro-2-methoxy-phenyl)-5,6-difluoro-1H-benzoimidazole

The title compound was prepared in analogy to Example 19, intermediate b, from 2-(4-chloro-2-methoxy-phenyl)-5,6-difluoro-1H-benzoimidazole (Example 19, intermediate c) and bromomethyl-benzene (CAS Reg. No. 100-39-0). Brown sticky solid (81%). MS (Turbo Spray): m/z=385.2 (M+H).

Example 49

1-Benzyl-2-(4-chloro-2-cyclopentylmethoxy-phenyl)-5,6-difluoro-1H-benzoimidazole

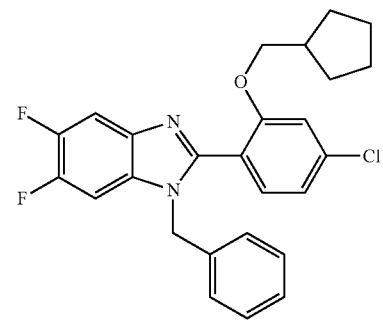

The title compound was prepared in analogy to Example 19, from 2-(1-benzyl-5,6-difluoro-1H-benzoimidazol-2-yl)-

5-chloro-phenol (Example 48, intermediate a) and bromomethyl-cyclopentane (CAS Reg. No. 3814-30-0). Colorless powder (33%). MS (Turbo Spray): m/z=453.0 (M+H).

Example 50

1-Benzyl-2-(4-chloro-2-cyclopropylmethoxy-phenyl)-5,6-difluoro-1H-benzoimidazole

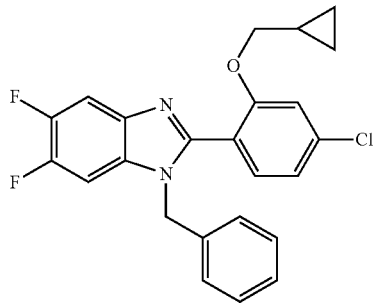

The title compound was prepared in analogy to Example 19, from 2-(1-benzyl-5,6-difluoro-1H-benzoimidazol-2-yl)-5-chloro-phenol (Example 48, intermediate a) and bromomethyl-cyclopropane (CAS Reg. No. 7051-34-5). Colorless powder (70%). MS (Turbo Spray): m/z=425.3 (M+H).

Example 51

4-[2-(1-Benzyl-5,6-difluoro-1H-benzoimidazol-2-yl)-5-chloro-phenoxymethyl]-benzoic acid

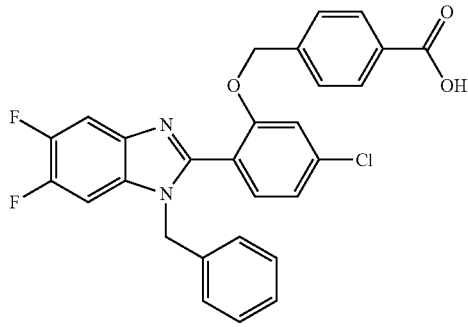

The title compound was prepared in analogy to Example 4, from 4-[2-(1-benzyl-5,6-difluoro-1H-benzoimidazol-2-yl)-5-chloro-phenoxymethyl]-benzoic acid methyl ester. Off-white powder (48%). MS (Turbo Spray): m/z=505.3 (M+H).

Intermediate

4-[2-(1-Benzyl-5,6-difluoro-1H-benzoimidazol-2-yl)-5-chloro-phenoxymethyl]-benzoic acid methyl ester The title compound was prepared in analogy to Example 5, intermediate a, from 2-(1-benzyl-5,6-difluoro-1H-benzoimidazol-2-yl)-5-chloro-phenol (Example 48, intermediate a) and 4-bromomethyl-benzoic acid methyl ester (CAS Reg. No. 2417-72-3). Brown sticky solid (86%). MS (Turbo Spray): m/z=518.0 (M+H).

Example 52

{4-[2-(1-Benzyl-5,6-difluoro-1H-benzoimidazol-2-yl)-5-chloro-phenoxymethyl]-phenoxy}-acetic acid

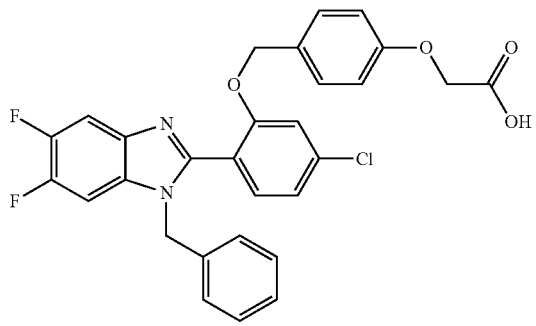

The title compound was prepared in analogy to Example 4, from {4-[2-(1-benzyl-5,6-difluoro-1H-benzoimidazol-2-yl)-5-chloro-phenoxymethyl]-phenoxy}-acetic acid methyl ester. Colorless powder (39%). MS (Turbo Spray): m/z=535.5 (M+H).

Intermediate

{4-[2-(1-Benzyl-5,6-difluoro-1H-benzoimidazol-2-yl)-5-chloro-phenoxymethyl]-phenoxy}-acetic acid methyl ester The title compound was prepared in analogy to Example 5, intermediate a, from 2-(1-benzyl-5,6-difluoro-1H-benzoimidazol-2-yl)-5-chloro-phenol (Example 48, intermediate a) and (4-bromomethyl-phenoxy)-acetic acid methyl ester (CAS Reg. No. 104508-23-8). Brown sticky solid (67%). MS (Turbo Spray): m/z=549.2 (M+H).

Example 53

1-(3-Chloro-benzyl)-2-[4-chloro-2-(2-chloro-benzyloxy)-phenyl]-5,6-difluoro-1H-benzoimidazole

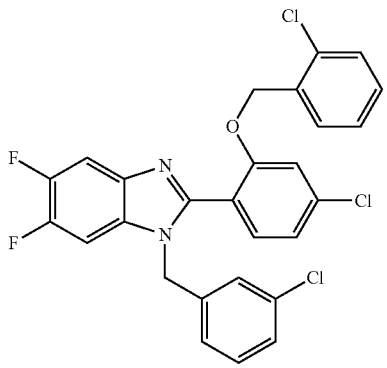

The title compound was prepared in analogy to Example 19, from 5-chloro-2-[1-(3-chloro-benzyl)-5,6-difluoro-1H-benzoimidazol-2-yl]-phenol and 1-bromomethyl-3-chlorobenzene (CAS Reg. No. 766-80-3). Colorless powder (31%). MS (Turbo Spray): m/z=528.9 (M+H).

Intermediates a) 5-Chloro-2-[1-(3-chloro-benzyl)-5,6-difluoro-1H-benzoimidazol-2-yl]-phenol The title compound was prepared in analogy to Example 19, intermediate a, from 1-(3-chloro-benzyl)-2-(4-chloro-2-methoxy-phenyl)-5,6-difluoro-1H-benzoimidazole. Colorless powder (66%). MS (Turbo Spray): m/z=404.8 (M+H).

b) 1-(3-Chloro-benzyl)-2-(4-chloro-2-methoxy-phenyl)-5,6-difluoro-1H-benzoimidazole The title compound was prepared in analogy to Example 19, intermediate b, from 2-(4-chloro-2-methoxy-phenyl)-5,6-difluoro-1H-benzoimidazole (Example 19, intermediate c) and 1-bromomethyl-3-chloro-benzene (CAS Reg. No. 766-80-3). Brown sticky solid (95%). MS (Turbo Spray): m/z=419.2 (M+H).

Example 54

1-(3-Chloro-benzyl)-2-(4-chloro-2-cyclopentyl-methoxy-phenyl)-5,6-difluoro-1H-benzoimidazole

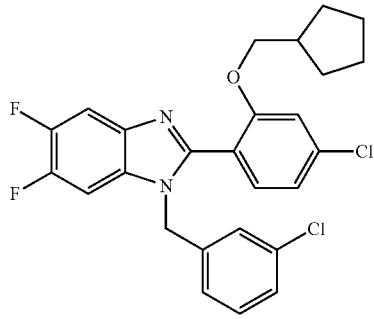

The title compound was prepared in analogy to Example 19, from 5-chloro-2-[1-(3-chloro-benzyl)-5,6-difluoro-1H-benzoimidazol-2-yl]-phenol (Example 53, intermediate a) and bromomethyl-cyclopentane (CAS Reg. No. 3814-30-0). Colorless powder (29%). MS (Turbo Spray): m/z=487.1 (M+H).

Example 55

1-(3-Chloro-benzyl)-2-(4-chloro-2-cyclopropyl-methoxy-phenyl)-5,6-difluoro-1H-benzoimidazole

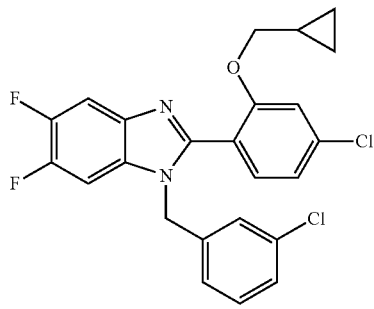

The title compound was prepared in analogy to Example 19, from 5-chloro-2-[1-(3-chloro-benzyl)-5,6-difluoro-1H-benzoimidazol-2-yl]-phenol (Example 53, intermediate a) and bromomethyl-cyclopropane (CAS Reg. No. 7051-34-5). Colorless powder (22%). MS (Turbo Spray): m/z=459.3 (M+H).

Example 56

4-{5-Chloro-2-[1-(3-chloro-benzyl)-5,6-difluoro-1H-benzoimidazol-2-yl]-phenoxymethyl}-benzoic acid

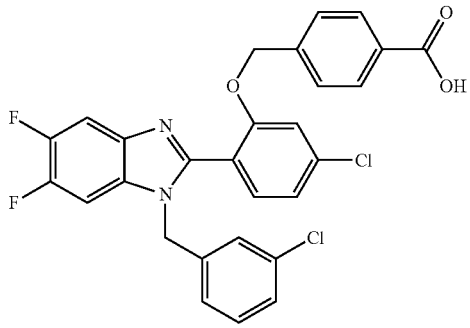

The title compound was prepared in analogy to Example 4, from 4-{5-chloro-2-[1-(3-chloro-benzyl)-5,6-difluoro-1H-benzoimidazol-2-yl]-phenoxymethyl}-benzoic acid methyl ester. Off-white powder (38%). MS (Turbo Spray): m/z=439.4 (M+H).

Intermediate

4-{5-Chloro-2-[1-(3-chloro-benzyl)-5,6-difluoro-1H-benzoimidazol-2-yl]-phenoxymethyl}-benzoic acid methyl ester The title compound was prepared in analogy to Example 5, intermediate a, from 5-chloro-2-[1-(3-chloro-benzyl)-5,6-difluoro-1H-benzoimidazol-2-yl]-phenol (Example 53, intermediate a) and 4-bromomethyl-benzoic acid methyl ester (CAS Reg. No. 2417-72-3). Colorless sticky solid (56%). MS (Turbo Spray): m/z=553.1 (M+H).

Example 57

(4-{5-Chloro-2-[1-(3-chloro-benzyl)-5,6-difluoro-1H-benzoimidazol-2-yl]-phenoxymethyl}-phenoxy)-acetic acid

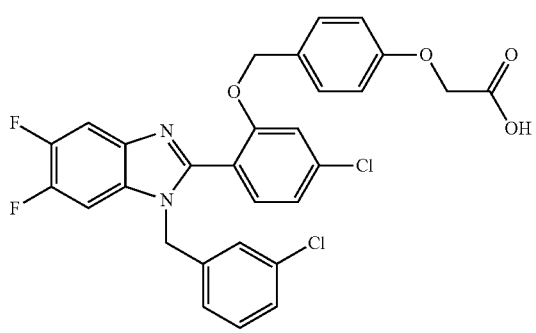

The title compound was prepared in analogy to Example 4, from (4-{5-chloro-2-[1-(3-chloro-benzyl)-5,6-difluoro-1H- benzoimidazol-2-yl]-phenoxymethyl}-phenoxy)-acetic acid methyl ester. White powder (36%). MS (Turbo Spray): m/z=571.3 (M+H).

Intermediate (4-{5-Chloro-2-[1-(3-chloro-benzyl)-5,6-difluoro-1H-benzoimidazol-2-yl]-phenoxymethyl}-phenoxy)-acetic acid methyl ester The title compound was prepared in analogy to Example 5, intermediate a, from 5-chloro-2-[1-(3-chloro-benzyl)-5,6-difluoro-1H-benzoimidazol-2-yl]-phenol (Example 53, intermediate a) and (4-bromomethyl-phenoxy)-acetic acid methyl ester (CAS Reg. No. 104508-23-8). Brown sticky solid (74%). MS (Turbo Spray): m/z=583.4 (M+H).

Example 58

3-(4-{2-[4-Chloro-2-(2-chloro-benzyloxy)-phenyl]-5,6-difluoro-benzoimidazol-1-ylmethyl}-phenyl)-propionic acid

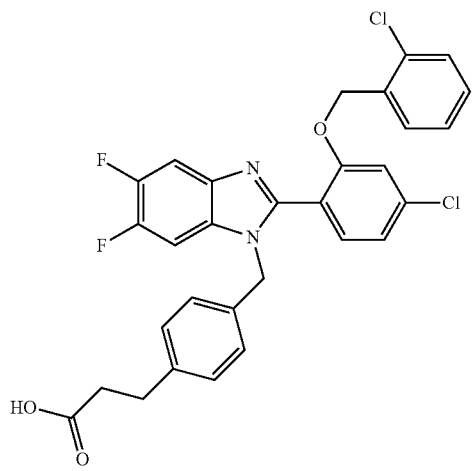

The title compound was prepared in analogy to Example 4, from 3-(4-{2-[4-chloro-2-(2-chloro-benzyloxy)-phenyl]-5,6-difluoro-benzoimidazol-1-ylmethyl}-phenyl)-propionic acid methyl ester. White powder (40%). MS (Turbo Spray): m/z=567.2 (M+H).

Intermediates a) 3-(4-{2-[4-Chloro-2-(2-chloro-benzyloxy)-phenyl]-5,6-difluoro-benzoimidazol-1-ylmethyl}-phenyl)-propionic acid methyl ester The title compound was prepared in analogy to Example 19, from 3-{4-[2-(4-chloro-2-hydroxy-phenyl)-5,6-difluoro-benzoimidazol-1-ylmethyl]-phenyl}-propionic acid methyl ester and 1-bromomethyl-3-chloro-benzene (CAS Reg. No. 766-80-3). Brown solid (47%). MS (Turbo Spray): m/z=581.0 (M+H).

b) 3-{4-[2-(4-Chloro-2-hydroxy-phenyl)-5,6-difluoro-benzoimidazol-1-ylmethyl]-phenyl}-propionic acid methyl ester The title compound was prepared in analogy to Example 19, intermediate a, from 3-{4-[2-(4-chloro-2-methoxy-phenyl)-5,6-difluoro-benzoimidazol-1-ylmethyl]-phenyl}-propionic acid methyl ester. Colorless solid (61%). MS (Turbo Spray): m/z=457.3 (M+H).

c) 3-{4-[2-(4-Chloro-2-methoxy-phenyl)-5,6-difluoro-benzoimidazol-1-ylmethyl]-phenyl}-propionic acid methyl ester The title compound was prepared in analogy to Example 19, intermediate b, from 2-(4-chloro-2-methoxy-phenyl)-5,6-difluoro-1H-benzoimidazole (Example 19, intermediate c) and 3-(4-bromomethyl-phenyl)-propionic acid methyl ester (CAS Reg. No. 56607-18-2). Brown sticky solid (75%). MS (Turbo Spray): m/z=471.0 (M+H).

Example 59

3-{4-[2-(4-Chloro-2-cyclopentylmethoxy-phenyl)-5,6-difluoro-benzoimidazol-1-ylmethyl]-phenyl}-propionic acid

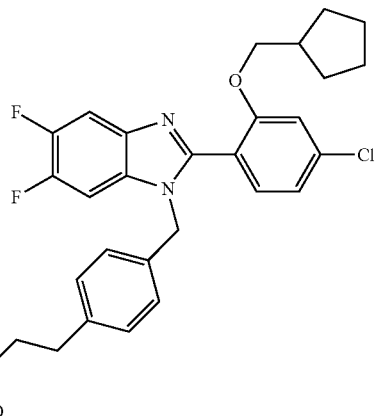

The title compound was prepared in analogy to Example 4, from 3-{4-[2-(4-chloro-2-cyclopentylmethoxy-phenyl)-5,6-difluoro-benzoimidazol-1-ylmethyl]-phenyl}-propionic acid methyl ester. Light brown powder (52%). MS (Turbo Spray): m/z=525.3 (M+H).

Intermediate

3-{4-[2-(4-Chloro-2-cyclopentylmethoxy-phenyl)-5,6-difluoro-benzoimidazol-1-ylmethyl]-phenyl}-propionic acid methyl ester The title compound was prepared in analogy to Example 19, from 3-{4-[2-(4-chloro-2-hydroxy-phenyl)-5,6-difluoro-benzoimidazol-1-ylmethyl]-phenyl}-propionic acid methyl ester (Example 59, intermediate b) and bromomethyl-cyclopentane (CAS Reg. No. 3814-30-0). Brown sticky solid (27%). MS (Turbo Spray): m/z=539.2 (M+H).

Example 60

3-{4-[2-(4-Chloro-2-cyclopropylmethoxy-phenyl)-5,6-difluoro-benzoimidazol-1-ylmethyl]-phenyl}-propionic acid

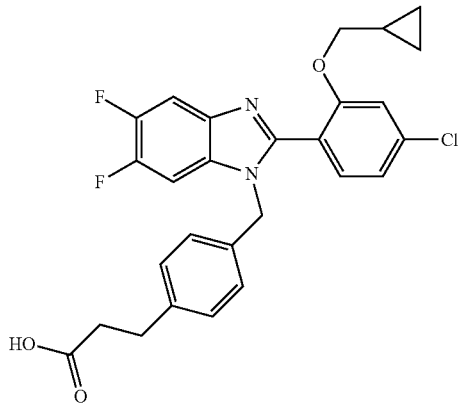

The title compound was prepared in analogy to Example 4, from 3-{4-[2-(4-chloro-2-cyclopropylmethoxy-phenyl)-5,6-difluoro-benzoimidazol-1-ylmethyl]-phenyl}-propionic acid methyl ester. Colorless powder (43%). MS (Turbo Spray): m/z=497.2 (M+H).

Intermediate

3-{4-[2-(4-Chloro-2-cyclopropylmethoxy-phenyl)-5,6-difluoro-benzoimidazol-1-ylmethyl]-phenyl}-propionic acid methyl ester The title compound was prepared in analogy to Example 19, from 3-{4-[2-(4-chloro-2-hydroxy-phenyl)-5,6-difluoro-benzoimidazol-1-ylmethyl]-phenyl}-propionic acid methyl ester (Example 59, intermediate b) and bromomethyl-cyclopropane (CAS Reg. No. 7051-34-5). Brown solid (54%). MS (Turbo Spray): m/z=511.2 (M+H).

Example 61

3-[2-(4-Chloro-2-cyclopentylmethoxy-phenyl)-5,6-difluoro-benzoimidazol-1-ylmethyl]-benzoic acid

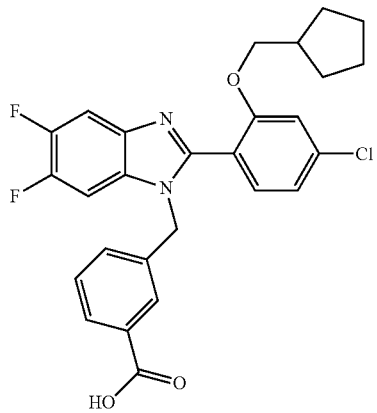

The title compound was prepared in analogy to Example 4, from 3-[2-(4-chloro-2-cyclopentylmethoxy-phenyl)-5,6-difluoro-benzoimidazol-1-ylmethyl]-benzoic acid methyl ester. Off-white powder (43%). MS (Turbo Spray): m/z=497.4 (M+H).

Intermediates a) 3-[2-(4-Chloro-2-cyclopentylmethoxy-phenyl)-5,6-difluoro-benzoimidazol-1-ylmethyl]-benzoic acid methyl ester The title compound was prepared in analogy to Example 5, intermediate a, from 3-[2-(4-chloro-2-hydroxy-phenyl)-5,6-difluoro-benzoimidazol-1-ylmethyl]-benzoic acid methyl ester and bromomethyl-cyclopentane (CAS Reg. No. 3814-30-0). Brown sticky solid (72%). MS (Turbo Spray): m/z=511.2 (M+H).

b) 3-[2-(4-Chloro-2-hydroxy-phenyl)-5,6-difluoro-benzoimidazol-1-ylmethyl]-benzoic acid methyl ester The title compound was prepared in analogy to Example 19, intermediate a, from 3-[2-(4-chloro-2-methoxy-phenyl)-5,6-difluoro-benzoimidazol-1-ylmethyl]-benzoic acid methyl ester. Off-white powder (50%). MS (Turbo Spray): m/z=428.7 (M+H).

c) 3-[2-(4-Chloro-2-methoxy-phenyl)-5,6-difluoro-benzoimidazol-1-ylmethyl]-benzoic acid methyl ester The title compound was prepared in analogy to Example 19, intermediate b, from 2-(4-chloro-2-methoxy-phenyl)-5,6-difluoro-1H-benzoimidazole (Example 19, intermediate c) and (3-bromomethyl-benzoic acid methyl ester CAS Reg. No. 1129-28-8). Brown sticky solid (67%). MS (Turbo Spray): m/z=443.2 (M+H).

Example 62

4-[2-(4-Chloro-2-cyclopentylmethoxy-phenyl)-5,6-difluoro-benzoimidazol-1-ylmethyl]-benzoic acid

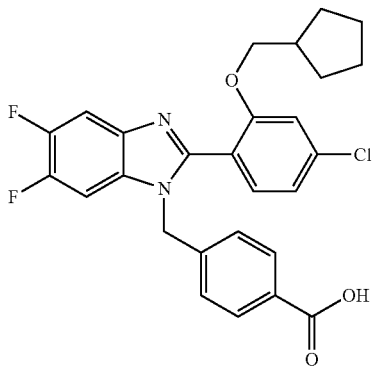

The title compound was prepared in analogy to Example 4, from 4-[2-(4-chloro-2-cyclopentylmethoxy-phenyl)-5,6-difluoro-benzoimidazol-1-ylmethyl]-benzoic acid methyl ester. Off-white powder (77%). MS (Turbo Spray): m/z=497.6 (M+H).

Intermediates a) 4-[2-(4-Chloro-2-cyclopentylmethoxy-phenyl)-5,6-difluoro-benzoimidazol-1-ylmethyl]-benzoic acid methyl ester The title compound was prepared in analogy to Example 5, intermediate a, from 3-[2-(4-chloro-2-hydroxy-phenyl)-5,6-difluoro-benzoimidazol-1-ylmethyl]-benzoic acid methyl ester (Example 61, intermediate c) and bromomethyl-cyclopentane (CAS Reg. No. 3814-30-0). Brown solid (92%). MS (Turbo Spray): m/z=511.3 (M+H).

b) 4-[2-(4-Chloro-2-hydroxy-phenyl)-5,6-difluoro-benzoimidazol-1-ylmethyl]-benzoic acid methyl ester The title compound was prepared in analogy to Example 19, intermediate a, from 4-[2-(4-chloro-2-methoxy-phenyl)-5,6-difluoro-benzoimidazol-1-ylmethyl]-benzoic acid methyl ester. Colorless solid (67%). MS (Turbo Spray): m/z=429.0 (M+H).

c) 4-[2-(4-Chloro-2-methoxy-phenyl)-5,6-difluoro-benzoimidazol-1-ylmethyl]-benzoic acid methyl ester The title compound was prepared in analogy to Example 19, intermediate b, from 2-(4-chloro-2-methoxy-phenyl)-5,6-difluoro-1H-benzoimidazole (Example 19, intermediate c) and 4-bromomethyl-benzoic acid methyl ester (CAS Reg. No. 2417-72-3). Brown solid (33%). MS (Turbo Spray): m/z=443.2 (M+H).

Example 63

{4-[2-(4-Chloro-2-cyclopentylmethoxy-phenyl)-5,6-difluoro-benzoimidazol-1-ylmethyl]-phenyl}-acetic acid

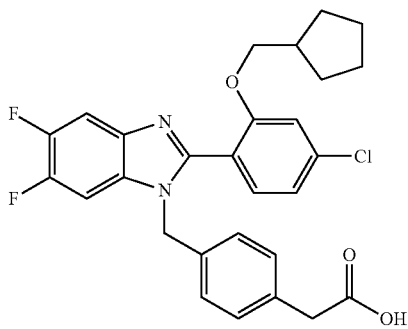

The title compound was prepared in analogy to Example 4, from {4-[2-(4-chloro-2-cyclopentylmethoxy-phenyl)-5,6-difluoro-benzoimidazol-1-ylmethyl]-phenyl}-acetic acid methyl ester. Off-white powder (32%). MS (Turbo Spray): m/z=511.4 (M+H).

Intermediates a) {4-[2-(4-Chloro-2-cyclopentylmethoxy-phenyl)-5,6-difluoro-benzoimidazol-1-ylmethyl]-phenyl}-acetic acid methyl ester The title compound was prepared in analogy to Example 5, intermediate a, from {4-[2-(4-chloro-2-hydroxy-phenyl)-5,6-difluoro-benzoimidazol-1-ylmethyl]-phenyl}-acetic acid methyl ester and bromomethyl-cyclopentane (CAS Reg. No. 3814-30-0). Brown sticky solid (61%). MS (Turbo Spray): m/z=525.4 (M+H).

b) {4-[2-(4-Chloro-2-hydroxy-phenyl)-5,6-difluoro-benzoimidazol-1-ylmethyl]-phenyl}-acetic acid methyl ester The title compound was prepared in analogy to Example 19, intermediate a, from {4-[2-(4-chloro-2-methoxy-phenyl)-5,6-difluoro-benzoimidazol-1-ylmethyl]phenyl}-acetic acid methyl ester. Colorless powder (26%). MS (Turbo Spray): m/z=442.7 (M+H).

c) {4-[2-(4-Chloro-2-methoxy-phenyl)-5,6-difluoro-benzoimidazol-1-ylmethyl]-phenyl}-acetic acid methyl ester The title compound was prepared in analogy to Example 19, intermediate b, from 2-(4-chloro-2-methoxy-phenyl)-5,6-difluoro-1H-benzoimidazole (Example 19, intermediate c) and (4-bromomethyl-phenyl)-acetic acid methyl ester (CAS Reg. No. 7398-42-7). Brown sticky solid (15%). MS (Turbo Spray): m/z=457.4 (M+H).

Example 64

{4-[2-(4-Chloro-2-cyclopentylmethoxy-phenyl)-5,6-difluoro-benzoimidazol-1-ylmethyl]-phenoxy}-acetic acid

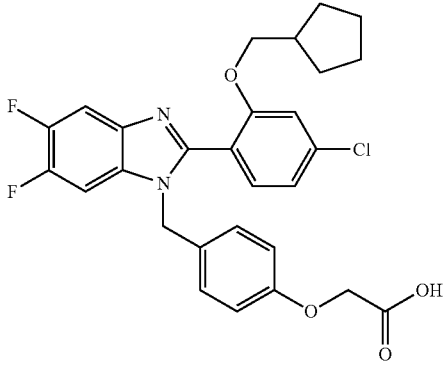

The title compound was prepared in analogy to Example 4, from {4-[2-(4-chloro-2-cyclopentylmethoxy-phenyl)-5,6-difluoro-benzoimidazol-1-ylmethyl]-phenoxy}-acetic acid methyl ester. White powder (62%). MS (Turbo Spray): m/z=527.4 (M+H).

Intermediates a) {4-[2-(4-Chloro-2-cyclopentylmethoxy-phenyl)-5,6-difluoro-benzoimidazol-1-ylmethyl]-phenoxy}-acetic acid methyl ester The title compound was prepared in analogy to Example 5, intermediate a, from {4-[2-(4-chloro-2-hydroxy-phenyl)-5,6-difluoro-benzoimidazol-1-ylmethyl]-phenoxy}-acetic acid methyl ester and bromomethyl-cyclopentane (CAS Reg. No. 3814-30-0). Brown sticky solid (57%). MS (Turbo Spray): m/z=540.9 (M+H).

b) {4-[2-(4-Chloro-2-hydroxy-phenyl)-5,6-difluoro-benzoimidazol-1-ylmethyl]-phenoxy}-acetic acid methyl ester The title compound was prepared in analogy to Example 19, intermediate a, from {4-[2-(4-chloro-2-methoxy-phenyl)-5,6-difluoro-benzoimidazol-1-ylmethyl]-phenoxy}-acetic acid methyl ester. Colorless powder (32%). MS (Turbo Spray): m/z=459.2 (M+H).

c) {4-[2-(4-Chloro-2-methoxy-phenyl)-5,6-difluoro-benzoimidazol-1-ylmethyl]-phenoxy}-acetic acid methyl ester The title compound was prepared in analogy to Example 19, intermediate b, from 2-(4-chloro-2-methoxy-phenyl)-5,6-difluoro-1H-benzoimidazole (Example 19, intermediate c) and (4-bromomethyl-phenoxy)-acetic acid methyl ester (CAS Reg. No. 104508-23-8). Brown sticky solid (50%). MS (Turbo Spray): m/z=472.7 (M+H).

Example 65

6-[2-(4-Chloro-2-cyclopentylmethoxy-phenyl)-5,6-difluoro-benzoimidazol-1-yl]-hexanoic acid

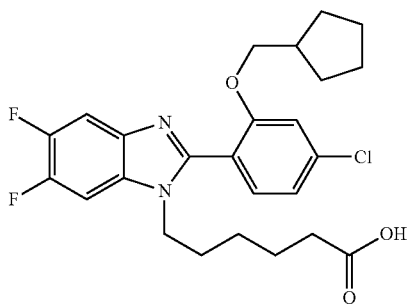

The title compound was prepared in analogy to Example 4, from 6-[2-(4-chloro-2-cyclopentylmethoxy-phenyl)-5,6-difluoro-benzoimidazol-1-yl]-hexanoic acid methyl ester. Colorless powder (39%). MS (Turbo Spray): m/z=477.3 (M+H).

Intermediates a) 6-[2-(4-Chloro-2-cyclopentylmethoxy-phenyl)-5,6-difluoro-benzoimidazol-1-yl]-hexanoic acid methyl ester The title compound was prepared in analogy to Example 5, intermediate a, from 6-[2-(4-chloro-2-hydroxy-phenyl)-5,6-difluoro-benzoimidazol-1-yl]-hexanoic acid methyl ester and bromomethyl-cyclopentane (CAS Reg. No. 3814-30-0). Brown sticky solid (65%). MS (Turbo Spray): m/z=505.3 (M+H).

b) 6-[2-(4-Chloro-2-hydroxy-phenyl)-5,6-difluoro-benzoimidazol-1-yl]-hexanoic acid methyl ester The title compound was prepared in analogy to Example 19, intermediate a, from 6-[2-(4-chloro-2-methoxy-phenyl)-5,6-difluoro-benzoimidazol-1-yl]-hexanoic acid methyl ester. Colorless solid (40%). MS (Turbo Spray): m/z=423.1 (M+H).

c) 6-[2-(4-Chloro-2-methoxy-phenyl)-5,6-difluoro-benzoimidazol-1-yl]-hexanoic acid methyl ester The title compound was prepared in analogy to Example 19, intermediate b, from 2-(4-chloro-2-methoxy-phenyl)-5,6-difluoro-1H-benzoimidazole (Example 19, intermediate c) and (6-bromo-hexanoic acid ethyl ester (CAS Reg. No. 25542-62-5). Brown solid (67%). MS (Turbo Spray): m/z=437.2 (M+H).

Example 66

4-[2-(4-Chloro-2-cyclopentylmethoxy-phenyl)-5,6-difluoro-benzoimidazol-1-ylmethyl]-cyclohexane carboxylic acid

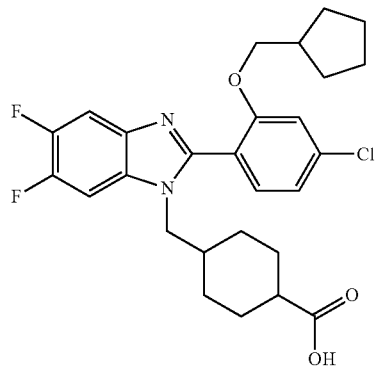

The title compound was prepared in analogy to Example 4, from 4-[2-(4-chloro-2-cyclopentylmethoxy-phenyl)-5,6-difluoro-benzoimidazol-1-ylmethyl]-cyclohexane carboxylic acid methyl ester. Colorless powder (62%). MS (Turbo Spray): m/z=503.4 (M+H).

Intermediates a) 4-[2-(4-Chloro-2-cyclopentylmethoxy-phenyl)-5,6-difluoro-benzoimidazol-1-ylmethyl]-cyclohexane carboxylic acid methyl ester The title compound was prepared in analogy to Example 5, intermediate a, from 4-[2-(4-chloro-2-hydroxy-phenyl)-5,6-difluoro-benzoimidazol-1-ylmethyl]-cyclohexane carboxylic acid methyl ester and bromomethyl-cyclopentane (CAS Reg. No. 3814-30-0). Brown solid (56%). MS (Turbo Spray): m/z=517.4 (M+H).

b) 4-[2-(4-Chloro-2-hydroxy-phenyl)-5,6-difluoro-benzoimidazol-1-ylmethyl]-cyclohexane carboxylic acid methyl ester The title compound was prepared in analogy to Example 19, intermediate a, from 4-[2-(4-chloro-2-methoxy-phenyl)-5,6-difluoro-benzoimidazol-1-ylmethyl]-cyclohexane carboxylic acid methyl ester. Colorless powder (37%). MS (Turbo Spray): m/z=434.9 (M+H).

c) 4-[2-(4-Chloro-2-methoxy-phenyl)-5,6-difluoro-benzoimidazol-1-ylmethyl]-cyclohexane carboxylic acid methyl ester The title compound was prepared in analogy to Example 19, intermediate b, from 2-(4-chloro-2-methoxy-phenyl)-5, 6-difluoro-1H-benzoimidazole (Example 19, intermediate c) and 4-(toluene-4-sulfonyloxymethyl)-cyclohexane carboxylic acid methyl ester (Example 29, intermediate b). Brown solid (31%). MS (Turbo Spray): m/z=449.3 (M+H).

Example 67

2-(4-Chloro-2-cyclopentylmethoxy-phenyl)-5,6-difluoro-1-[3-(1H-tetrazol-5-yl)-benzyl]-1H-benzoimidazole

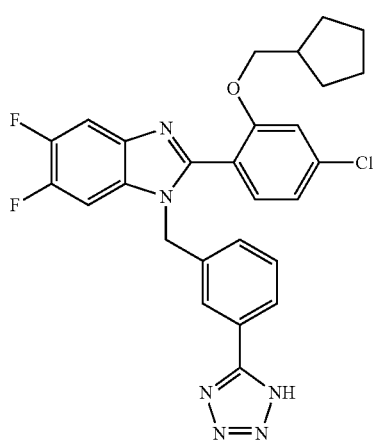

The title compound was prepared in analogy to Example 30, from 3-[2-(4-Chloro-2-cyclopentylmethoxy-phenyl)-5,6-difluoro-benzoimidazol-1-ylmethyl]-benzonitrile. Off-white powder (23%). MS (Turbo Spray): m/z=520.8 (M+H).

Intermediates a) 3-[2-(4-Chloro-2-cyclopentylmethoxy-phenyl)-5,6-difluoro-benzoimidazol-1-ylmethyl]-benzonitrile The title compound was prepared in analogy to Example 19, from 3-[2-(4-chloro-2-hydroxy-phenyl)-5,6-difluoro-benzoimidazol-1-ylmethyl]-benzonitrile and bromomethyl-cyclopentane (CAS Reg. No. 3814-30-0). Brown solid (33%). MS (Turbo Spray): m/z=378.2 (M+H).

b) 3-[2-(4-Chloro-2-hydroxy-phenyl)-5,6-difluoro-benzoimidazol-1-ylmethyl]-benzonitrile The title compound was prepared in analogy to Example 19, intermediate a, from 3-[2-(4-chloro-2-methoxy-phenyl)-5,6-difluoro-benzoimidazol-1-ylmethyl]-benzonitrile. Colorless solid (90%). MS (Turbo Spray): m/z=396.2 (M+H).

c) 3-[2-(4-Chloro-2-methoxy-phenyl)-5,6-difluoro-benzoimidazol-1-ylmethyl]-benzonitrile The title compound was prepared in analogy to Example 19, intermediate b, from 2-(4-chloro-2-methoxy-phenyl)-5,6-difluoro-1H-benzoimidazole (Example 19, intermediate c) and 3-bromomethyl-benzonitrile (CAS Reg. No. 28188-41-2). Brown solid (72%). MS (Turbo Spray): m/z=410.2 (M+H).

Example 68

2-(4-Chloro-2-cyclopentylmethoxy-phenyl)-5,6-difluoro-1-[4-(1H-tetrazol-5-yl)-benzyl]-1H-benzoimidazole

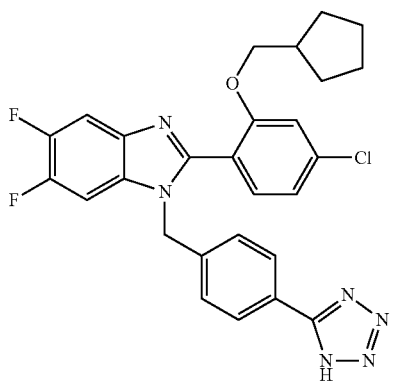

The title compound was prepared in analogy to Example 30, from 4-[2-(4-chloro-2-cyclopentylmethoxy-phenyl)-5,6-difluoro-benzoimidazol-1-ylmethyl]-benzonitrile. Off-white powder (19%). MS (Turbo Spray): m/z=521.6 (M+H).

Intermediates a) 4-[2-(4-Chloro-2-cyclopentylmethoxy-phenyl)-5,6-difluoro-benzoimidazol-1-ylmethyl]-benzonitrile The title compound was prepared in analogy to Example 19, from 4-[2-(4-chloro-2-hydroxy-phenyl)-5,6-difluoro-benzoimidazol-1-ylmethyl]-benzonitrile and bromomethyl-cyclopentane (CAS Reg. No. 3814-30-0). Brown solid (55%). MS (Turbo Spray): m/z=478.3 (M+H).

b) 4-[2-(4-Chloro-2-hydroxy-phenyl)-5,6-difluoro-benzoimidazol-1-ylmethyl]-benzonitrile The title compound was prepared in analogy to Example 19, intermediate a, from 4-[2-(4-chloro-2-hydroxy-phenyl)-5,6-difluoro-benzoimidazol-1-ylmethyl]-benzonitrile. Off-white powder (80%). MS (Turbo Spray): m/z=496.2 (M+H).

c) 4-[2-(4-Chloro-2-methoxy-phenyl)-5,6-difluoro-benzoimidazol-1-ylmethyl]-benzonitrile The title compound was prepared in analogy to Example 19, intermediate b, from 2-(4-chloro-2-methoxy-phenyl)-5,6-difluoro-1H-benzoimidazole (Example 19, intermediate c) and 4-bromomethyl-benzonitrile (CAS Reg. No. 17201-43-3). Brown solid (48%). MS (Turbo Spray): m/z=410.3 (M+H).

Example 69

2-(4-Chloro-2-cyclopentylmethoxy-phenyl)-5,6-difluoro-1-[3-fluoro-4-(1H-tetrazol-5-yl)-benzyl]-1H-benzoimidazole

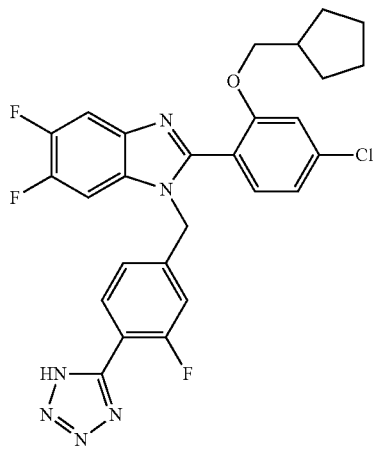

The title compound was prepared in analogy to Example 30, from 4-[2-(4-chloro-2-cyclopentylmethoxy-phenyl)-5,6-difluoro-benzoimidazol-1-ylmethyl]-2-fluoro-benzonitrile. Yellow powder (6%). MS (Turbo Spray): m/z=539.4 (M+H).

Intermediates a) 4-[2-(4-Chloro-2-cyclopentylmethoxy-phenyl)-5,6-difluoro-benzoimidazol-1-ylmethyl]-2-fluoro-benzonitrile The title compound was prepared in analogy to Example 19, from 4-[2-(4-chloro-2-hydroxy-phenyl)-5,6-difluoro-benzoimidazol-1-ylmethyl]-2-fluoro-benzonitrile and bromomethyl-cyclopentane (CAS Reg. No. 3814-30-0). Colorless solid (50%). MS (Turbo Spray): m/z=496.3 (M+H).

b) 4-[2-(4-Chloro-2-hydroxy-phenyl)-5,6-difluoro-benzoimidazol-1-ylmethyl]-2-fluoro-benzonitrile The title compound was prepared in analogy to Example 19, intermediate a, from 4-[2-(4-chloro-2-methoxy-phenyl)-5,6-difluoro-benzoimidazol-1-ylmethyl]-2-fluoro-benzonitrile. Colorless solid (52%). MS (Turbo Spray): m/z=414.0 (M+H).

c) 4-[2-(4-Chloro-2-methoxy-phenyl)-5,6-difluoro-benzoimidazol-1-ylmethyl]-2-fluoro-benzonitrile The title compound was prepared in analogy to Example 19, intermediate b, from 2-(4-chloro-2-methoxy-phenyl)-5,6-difluoro-1H-benzoimidazole (Example 19, intermediate c) and 4-bromomethyl-2-fluoro-benzonitrile (CAS Reg. No. 222978-03-2). Brown sticky solid (39%). MS (Turbo Spray): m/z=428.2 (M+H).

Example 70

2-(4-Chloro-2-cyclopentylmethoxy-phenyl)-5,6-difluoro-1-[2-fluoro-4-(1H-tetrazol-5-yl)-benzyl]-1H-benzoimidazole

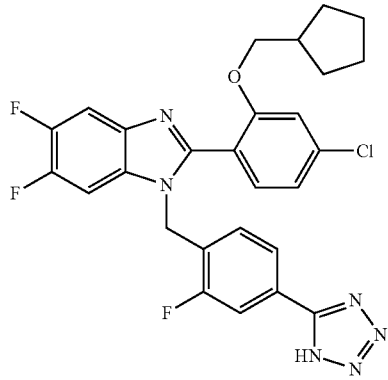

The title compound was prepared in analogy to Example 30, from 4-[2-(4-chloro-2-cyclopentylmethoxy-phenyl)-5,6-difluoro-benzoimidazol-1-ylmethyl]-3-fluoro-benzonitrile. Brown powder (14%). MS (Turbo Spray): m/z=539.1 (M+H).

Intermediates a) 4-[2-(4-Chloro-2-cyclopentylmethoxy-phenyl)-5,6-difluoro-benzoimidazol-1-ylmethyl]-3-fluoro-benzonitrile The title compound was prepared in analogy to Example 19, from 4-[2-(4-chloro-2-hydroxy-phenyl)-5,6-difluoro-benzoimidazol-1-ylmethyl]-3-fluoro-benzonitrile and bromomethyl-cyclopentane (CAS Reg. No. 3814-30-0). Brown sticky solid (78%). MS (Turbo Spray): m/z=496.0 (M+H).

b) 4-[2-(4-Chloro-2-hydroxy-phenyl)-5,6-difluoro-benzoimidazol-1-ylmethyl]-3-fluoro-benzonitrile The title compound was prepared in analogy to Example 19, intermediate a, from 4-[2-(4-chloro-2-methoxy-phenyl)-5,6-difluoro-benzoimidazol-1-ylmethyl]-3-fluoro-benzonitrile. Colorless solid (69%). MS (Turbo Spray): m/z=414.2 (M+H).

c) 4-[2-(4-Chloro-2-methoxy-phenyl)-5,6-difluoro-benzoimidazol-1-ylmethyl]-3-fluoro-benzonitrile The title compound was prepared in analogy to Example 19, intermediate b, from 2-(4-chloro-2-methoxy-phenyl)-5,6-difluoro-1H-benzoimidazole (Example 19, intermediate c) and 4-bromomethyl-3-fluoro-benzonitrile (CAS Reg. No. 105942-09-4). Brown sticky solid (31%). MS (Turbo Spray): m/z=428.2 (M+H).

Example 71

2-(4-Chloro-2-methoxy-phenyl)-5,6-difluoro-1-[2-fluoro-4-(1H-tetrazol-5-yl)-benzyl]-1H-benzoimidazole

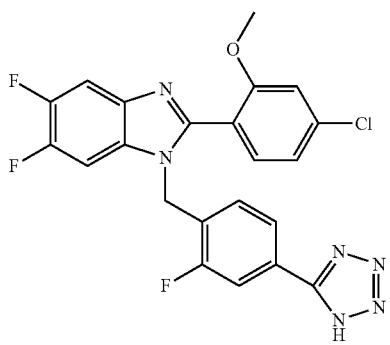

The title compound was prepared in analogy to Example 30, from 4-[2-(4-chloro-2-methoxy-phenyl)-5,6-difluoro-benzoimidazol-1-ylmethyl]-3-fluoro-benzonitrile (Example 70, intermediate b). Yellow powder (66%). MS (Turbo Spray): m/z=471.0 (M+H).

Example 72

2-{4-Chloro-2-[4-(1H-tetrazol-5-yl)-phenylethynyl]-phenyl}-1-cyclohexylmethyl-5,6-difluoro-1H-benzoimidazole

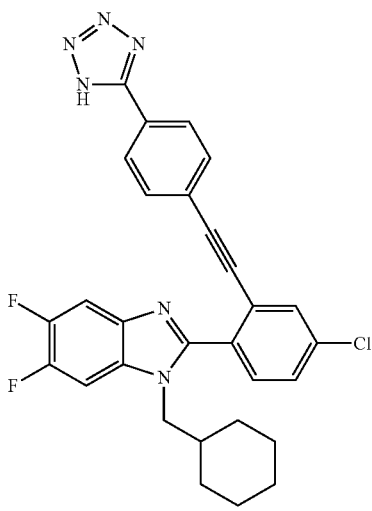

The title compound was prepared in analogy to Example 30, from 4-[5-chloro-2-(1-cyclohexylmethyl-5,6-difluoro-1H-benzoimidazol-2-yl)-phenylethynyl]-benzonitrile. Light yellow powder (59%). MS (Turbo Spray): m/z=529.4 (M+H).

Intermediates a) 4-[5-Chloro-2-(1-cyclohexylmethyl-5,6-difluoro-1H-benzoimidazol-2-yl)-phenylethynyl]-benzonitrile To a solution of 2-(2-bromo-4-chloro-phenyl)-1-cyclohexylmethyl-5,6-difluoro-1H-benzoimidazole (600 mg, 1.36 mmol) in tetrahydrofuran (20 ml) was added 4-ethynyl-benzonitrile (173.4 mg, 1.36 mmol; CAS Reg. No. 3032-92-6), bis(triphenylphosphine)palladium(ii) dichloride (57.2 mg, 0.08 mmol), copper iodide (7.7 mg, 0.04 mmol) and triethyl amine (20 ml) at 25° C. The resulting mixture was degassed and back-filled with nitrogen three times. It was then allowed to stir at 80° C. for 16 h. The reaction mixture was filtered through a bed of celite and solvents were removed under reduced pressure. The residue was purified by column chromatography over silica gel (10% ethyl acetate/n-hexane) to afford the desired compound as a yellow solid (18%). MS (Turbo Spray): m/z=485.6 (M+H).

b) 2-(2-Bromo-4-chloro-phenyl)-1-cyclohexylmethyl-5,6-difluoro-1H-benzoimidazole The title compound was prepared in analogy to Example 19, intermediate b, from 2-(2-bromo-4-chloro-phenyl)-5,6-difluoro-1H-benzoimidazole and bromomethyl-cyclohexane (CAS Reg. No. 2550-36-9). Off-white solid (60%). MS (Turbo Spray): m/z=440.2 (M+H).

c) 2-(2-Bromo-4-chloro-phenyl)-5,6-difluoro-1H-benzoimidazole

The title compound was prepared in analogy to Example 19, intermediate c, from 4,5-difluoro-benzene-1,2-diamine (CAS Reg. No. 76179-40-3) and 2-bromo-4-chloro-benzoic acid (CAS Reg. No. 936-08-3). Colorless solid (54%). MS (Turbo Spray): m/z=344.1 (M+H).

Example 73

2-(4-Chloro-2-{2-[4-(1H-tetrazol-5-yl)-phenyl]-ethyl}-phenyl)-1-cyclohexylmethyl-5,6-difluoro-1H-benzoimidazole

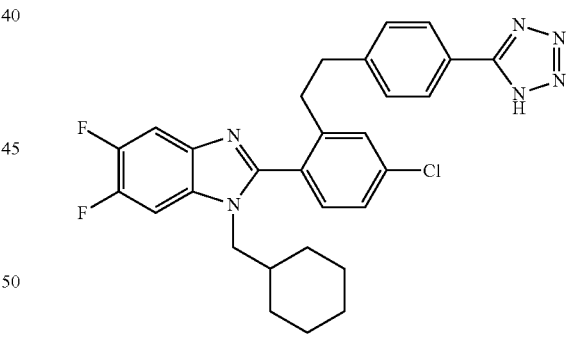

The title compound was prepared in analogy to Example 30, from 4-{2-[5-chloro-2-(1-cyclohexylmethyl-5,6-difluoro-1H-benzoimidazol-2-yl)-phenyl]-ethyl}-benzonitrile. Colorless powder (45%). MS (Turbo Spray): m/z=533.2 (M+H).

Intermediate

4-{2-[5-Chloro-2-(1-cyclohexylmethyl-5,6-difluoro-1H-benzoimidazol-2-yl)-phenyl]-ethyl}-benzonitrile To a solution of 4-[5-chloro-2-(1-cyclohexylmethyl-5,6-difluoro-1H-benzoimidazol-2-yl)-phenylethynyl]-benzonitrile (Example 71, intermediate a; 400 mg, 0.82 mmol) in methanol in argon atmosphere was added 10% palladium on carbon and stirred for 16 h at 25° C. under hydrogen balloon pressure. The reaction mixture was filtered through a bed of celite and evaporated under reduced pressure. The residue was purified by column chromatography over silica gel (10-12% ethyl acetate/n-hexane) to afford the desired compound as a yellow solid (20%). MS (Turbo Spray): m/z=490.6 (M+H).

Example 74

2-(4-Chloro-2-{2-[4-(1H-tetrazol-5-yl)-phenyl]-ethyl}-phenyl)-1-cyclohexylmethyl-1H-benzoimidazole

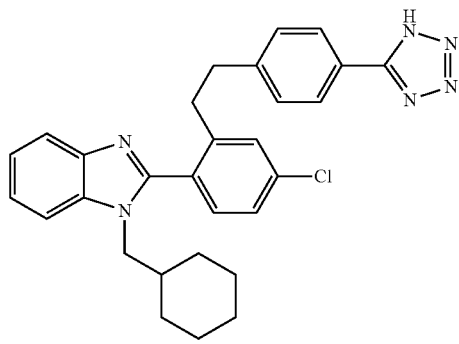

The title compound was prepared in analogy to Example 30, from 4-{2-[5-chloro-2-(1-cyclohexylmethyl-1H-benzoimidazol-2-yl)-phenyl]-ethyl}-benzonitrile. Off-white solid (63%). MS (Turbo Spray): m/z=497.2 (M+H).

Intermediates a) 4-{2-[5-Chloro-2-(1-cyclohexylmethyl-1H-benzoimidazol-2-yl)-phenyl]-ethyl}-benzonitrile To a solution of 4-[5-chloro-2-(1-cyclohexylmethyl-1H-benzoimidazol-2-yl)-phenylethynyl]-benzonitrile (0.27 g, 0.6 mmol) in methanol was added 10% palladium on carbon and stirred for 16 h at 25° C. under hydrogen balloon pressure. The reaction mixture was filtered through a bed of celite and evaporated under reduced pressure. The residue was purified by column chromatography over silica gel (10-20% ethyl acetate/n-hexane) to yield the compound as an off-white powder (23%). MS (Turbo Spray): m/z=454.4 (M+H).

b) 4-[5-Chloro-2-(1-cyclohexylmethyl-1H-benzoimidazol-2-yl)-phenylethynyl]-benzonitrile To a solution of 2-(2-bromo-4-chloro-phenyl)-1-cyclohexylmethyl-1H-benzoimidazole (0.56 g, 1.38 mmol) in dry tetrahydrofuran (8 ml) were added 4-ethynyl-benzonitrile (0.22 mg, 1.7 mmol; CAS Reg. No. 3032-92-6), bis(triphenylphosphine)palladium(ii) dichloride (63 mg, 0.09 mmol), copper(I) iodide (8 mg, 0.04 mmol) and triethyl amine (10 ml) at 25° C. in a sealed tube. The resulting mixture was degassed and back-filled with nitrogen three times. It was then allowed to stir at 80° C. for 16 h. The reaction mixture was filtered through a bed of celite, concentrated under reduced pressure. The residue was purified by column chromatography over silica gel (20-25 ethyl acetate/n-hexane) to afford the desired compound as an off-white powder (38%). MS (Turbo Spray): m/z=450.0 (M+H).

c) 2-(2-Bromo-4-chloro-phenyl)-1-cyclohexylmethyl-1H-benzoimidazole

The title compound was prepared in analogy to Example 19, intermediate b, from 2-(2-bromo-4-chloro-phenyl)-1H-benzoimidazole and bromomethyl-cyclohexane (CAS Reg. No. 2550-36-9). Colorless solid (95%). MS (Turbo Spray): m/z=404.2 (M+H).

d) 2-(2-Bromo-4-chloro-phenyl)-1H-benzoimidazole

The title compound was prepared in analogy to Example 19, intermediate c, from benzene-1,2-diamine (CAS Reg. No. 76179-40-3) and 2-bromo-4-chloro-benzoic acid (CAS Reg. No. 936-08-3). Light yellow solid (92%). MS (Turbo Spray): m/z=308.8 (M+H).

Example 75

4-{2-[5-Chloro-2-(1-cyclohexylmethyl-1H-benzoimidazol-2-yl)-phenyl]-ethyl}-benzoic acid

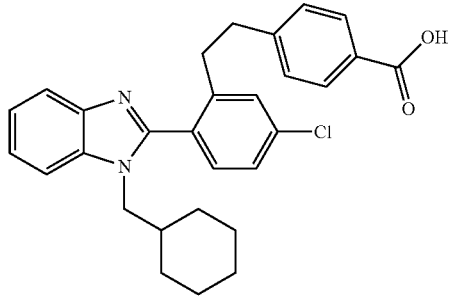

To a solution of 4-[2-[5-chloro-2-(1-cyclohexylmethyl-1H-benzoimidazol-2-yl)-phenyl]-ethyl]-benzonitrile (64 mg, 0.14 mmol; Example 74, intermediate a) in methanol (10 ml) was added a solution of potassium hydroxide (78 mg, 1.39 mmol) in water (5 ml) and the mixture was heated to reflux for 12 h. Solvents were removed under reduced pressure and the residue was diluted with water (10 ml) and acidified to pH 4 with 2M aqueous hydrochloric acid solution. It was then extracted three times with ethyl acetate (20 ml each), the combined organic layers were washed with brine, dried over sodium sulfate, filtered, and the solvent was evaporated under reduced pressure. The crude product was purified by column chromatography over silica gel (65% ethyl acetate/n-hexane) to give the desired final product as a colorless powder (31%). MS (Turbo Spray): m/z=473.3 (M+H).

Example 76

1-Cyclohexylmethyl-5,6-difluoro-2-(2-{2-[4-(1H-tetrazol-5-yl)-phenyl]-ethyl}-phenyl)-1H-benzoimidazole

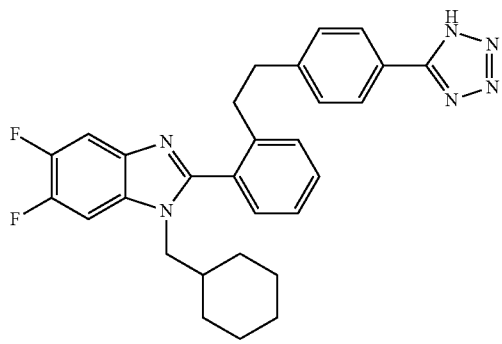

The title compound was prepared in analogy to Example 30, from 4-{2-[2-(1-cyclohexylmethyl-5,6-difluoro-1H-benzoimidazol-2-yl)-phenyl]-ethyl}-benzonitrile. Off-white solid (49%). MS (Turbo Spray): m/z=499.5 (M+H).

Intermediates a) 4-{2-[2-(1-cyclohexylmethyl-5,6-difluoro-1H-benzoimidazol-2-yl)-phenyl]-ethyl}-benzonitrile The title compound was prepared in analogy to Example 73, intermediate, from 4-[2-(1-cyclohexylmethyl-5,6-difluoro-1H-benzoimidazol-2-yl)-phenylethynyl]-benzonitrile. Off-white powder (23%). MS (Turbo Spray): m/z=456.6 (M+H).

b) 4-[2-(1-Cyclohexylmethyl-5,6-difluoro-1H-benzoimidazol-2-yl)-phenylethynyl]-benzonitrile The title compound was prepared in analogy to Example 72, intermediate a, from 2-(2-bromo-phenyl)-1-cyclohexylmethyl-5,6-difluoro-1H-benzoimidazole and 4-ethynyl-benzonitrile (CAS Reg. No. 3032-92-6). Off-white powder (30%). MS (Turbo Spray): m/z=452.4 (M+H).

c) 2-(2-Bromo-phenyl)-1-cyclohexylmethyl-5,6-difluoro-1H-benzoimidazole

The title compound was prepared in analogy to Example 19, intermediate b, from 2-(2-bromo-phenyl)-5,6-difluoro-1H-benzoimidazole and bromomethyl-cyclohexane (2550-36-9). Yellow sticky solid (94%). MS (Turbo Spray): m/z=406.1 (M+H).

d) 2-(2-Bromo-phenyl)-5,6-difluoro-1H-benzoimidazole

The title compound was prepared in analogy to Example 19, intermediate b, from 4,5-difluoro-benzene-1,2-diamine (CAS Reg. No. 76179-40-3) and 2-bromo-benzoic acid (CAS Reg. No. 88-65-3). Colorless powder (75%). MS (Turbo Spray): m/z=309.2 (M+H).

Example 77

4-{2-[2-(1-Cyclohexylmethyl-5,6-difluoro-1H-benzoimidazol-2-yl)-phenyl]-ethyl}-benzoic acid

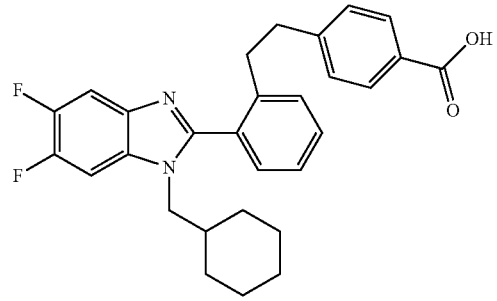

The title compound was prepared in analogy to Example 75, from 4-{2-[2-(1-cyclohexylmethyl-5,6-difluoro-1H-benzoimidazol-2-yl)-phenyl]-ethyl}-benzonitrile (Example 76, intermediate a). Off-white powder (30%). MS (Turbo Spray): m/z=475.4 (M+H).

Example 78

4-{2-[2-(1-Cyclohexylmethyl-1H-benzoimidazol-2-yl)-phenyl]-ethyl}-benzoic acid

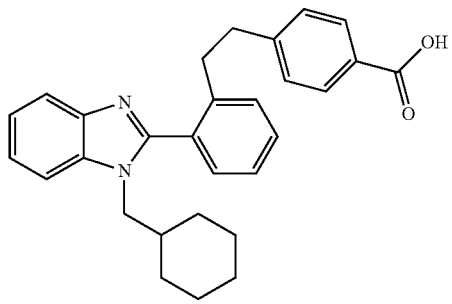

The title compound was prepared in analogy to Example 75, from 4-{2-[2-(1-cyclohexylmethyl-1H-benzoimidazol-2-yl)-phenyl]-ethyl}-benzonitrile (Example 80, intermediate a). Colorless powder (52%). MS (Turbo Spray): m/z=437.4 (M+H).

Example 79

(4-{2-[2-(1-Cyclohexylmethyl-1H-benzoimidazol-2-yl)-phenyl]-ethyl}-phenoxy)-acetic acid

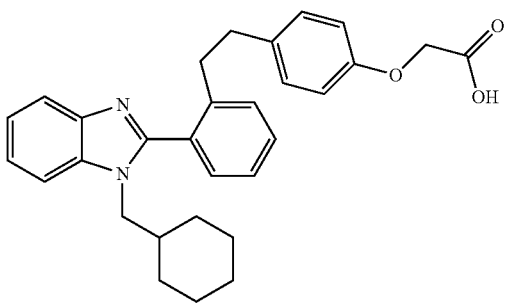

The title compound was prepared in analogy to Example 4, from (4-{2-[2-(1-cyclohexylmethyl-1H-benzoimidazol-2- yl)-phenyl]-ethyl}-phenoxy)-acetic acid methyl ester. Colorless powder (59%). MS (Turbo Spray): m/z=469.4 (M+H).

Intermediates a) (4-{2-[2-(1-Cyclohexylmethyl-1H-benzoimidazol-2-yl)-phenyl]-ethyl}-phenoxy)-acetic acid methyl ester The title compound was prepared in analogy to Example 5, intermediate a, from 4-{2-[2-(1-cyclohexylmethyl-1H-benzoimidazol-2-yl)-phenyl]-ethyl}-phenol and bromo-acetic acid methyl ester (CAS Reg. No. 96-32-2). Off-white semi-solid (77%). MS (Turbo Spray): m/z=497.4 (M+H).

b) 4-{2-[2-(1-Cyclohexylmethyl-1H-benzoimidazol-2-yl)-phenyl]-ethyl}-phenol

The title compound was prepared in analogy to Example 19, intermediate a, from 1-cyclohexylmethyl-2-{2-[2-(4-methoxy-phenyl)-ethyl]-phenyl}-1H-benzoimidazole. Yellow sticky solid (88%). MS (Turbo Spray): m/z=411.4 (M+H).

c) 1-Cyclohexylmethyl-2-{2-[2-(4-methoxy-phenyl)-ethyl]-phenyl}-1H-benzoimidazole The title compound was prepared in analogy to Example 73, intermediate, from 1-cyclohexylmethyl-2-[2-(4-methoxy-phenylethynyl)-phenyl]-1H-benzoimidazole. Yellow sticky solid (74%). MS (Turbo Spray): m/z=425.3 (M+H).

d) 1-Cyclohexylmethyl-2-[2-(4-methoxy-phenylethynyl)-phenyl]-1H-benzoimidazole

The title compound was prepared in analogy to Example 72, intermediate a, from 2-(2-bromo-phenyl)-1-cyclohexylmethyl-1H-benzoimidazole and 1-ethynyl-4-methoxy-benzene (CAS Reg. No. 768-60-5). Yellow sticky solid (24%). MS (Turbo Spray): m/z=421.4 (M+H).

e) 2-(2-Bromo-phenyl)-1-cyclohexylmethyl-1H-benzoimidazole

The title compound was prepared in analogy to Example 19, intermediate b, from 2-(2-bromo-phenyl)-1H-benzoimidazole and bromomethyl-cyclohexane (CAS Reg. No. 2550-36-9). Light brown solid (62%). MS (Turbo Spray): m/z=369.4 (M+H).

f) 2-(2-Bromo-phenyl)-5,6-difluoro-1H-benzoimidazole

The title compound was prepared in analogy to Example 19, intermediate c, from 4,5-difluoro-benzene-1,2-diamine (CAS Reg. No. 76179-40-3) and 2-bromo-benzoic acid (CAS Reg. No. 88-65-3). Yellow solid (85%). MS (Turbo Spray): m/z=273.0 (M+H).

Example 80

1-Cyclohexylmethyl-2-(2-{2-[4-(1H-tetrazol-5-yl)-phenyl]-ethyl}-phenyl)-1H-benzoimidazole

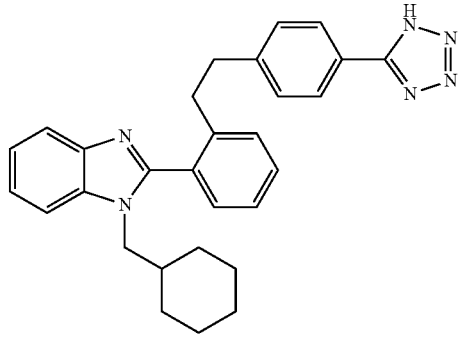

The title compound was prepared in analogy to Example 30, from 4-{2-[2-(1-cyclohexylmethyl-1H-benzoimidazol-2-yl)-phenyl]-ethyl}-benzonitrile. Light yellow powder (13%). MS (Turbo Spray): m/z=463.4 (M+H).

Intermediates a) 4-{2-[2-(1-Cyclohexylmethyl-1H-benzoimidazol-2-yl)-phenyl]-ethyl}-benzonitrile The title compound was prepared in analogy to Example 73, intermediate, from 4-[2-(1-cyclohexylmethyl-1H-benzoimidazol-2-yl)-phenylethynyl]-benzonitrile. Off-white powder (48%). MS (Turbo Spray): m/z=420.4 (M+H).

b) 4-[2-(1-Cyclohexylmethyl-1H-benzoimidazol-2-yl)-phenylethynyl]-benzonitrile

The title compound was prepared in analogy to Example 72, intermediate a, from 2-(2-bromo-phenyl)-1-cyclohexylmethyl-1H-benzoimidazole (Example 79, intermediate e) and 4-ethynyl-benzonitrile (CAS Reg. No. 3032-92-6). Yellow solid (22%). MS (Turbo Spray): m/z=416.6 (M+H).

Example 81

1-(4,4-Difluoro-cyclohexylmethyl)-2-(2-{2-[4-(1H-tetrazol-5-yl)-phenyl]-ethyl}-phenyl)-1H-benzoimidazole

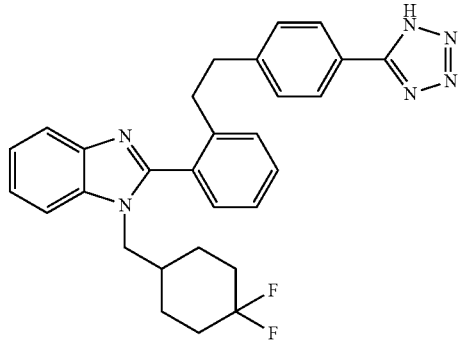

The title compound was prepared in analogy to Example 30, from 4-(2-{2-[1-(4,4-difluoro-cyclohexylmethyl)-1H-benzoimidazol-2-yl]-phenyl}-ethyl)-benzonitrile. Colorless powder (65%). MS (Turbo Spray): m/z=499.0 (M+H).

113

Intermediates a) 4-(2-{2-[1-(4,4-Difluoro-cyclohexylmethyl)-1H-benzoimidazol-2-yl]-phenyl}-ethyl)-benzonitrile The title compound was prepared in analogy to Example 73, intermediate, from 4-{2-[1-(4,4-difluoro-cyclohexylmethyl)-1H-benzoimidazol-2-yl]-phenylethynyl}-benzonitrile. Colorless powder (58%). MS (Turbo Spray): m/z=456.0 (M+H).

b) 4-{2-[1-(4,4-Difluoro-cyclohexylmethyl)-1H-benzoimidazol-2-yl]-phenylethynyl}-benzonitrile The title compound was prepared in analogy to Example 72, intermediate a, from 2-(2-bromo-phenyl)-1-(4,4-difluoro-cyclohexylmethyl)-1H-benzoimidazole and 4-ethynyl-benzonitrile (CAS Reg. No. 3032-92-6). Brown solid (38%). MS (Turbo Spray): m/z=452.2 (M+H).

c) 2-(2-Bromo-phenyl)-1-(4,4-difluoro-cyclohexylmethyl)-1H-benzoimidazole

The title compound was prepared in analogy to Example 19, intermediate b, from 2-(2-bromo-phenyl)-5,6-difluoro-1H-benzoimidazole (Example 79, intermediate f) and toluene-4-sulfonic acid 4,4-difluoro-cyclohexylmethyl ester (CAS Reg. No. 178310-99-1). Colorless powder (84%). MS (Turbo Spray): m/z=406.3 (M+H).

Example 82

1-(4-Methyl-cyclohexylmethyl)-2-(2-{2-[4-(1H-tetrazol-5-yl)-phenyl]-ethyl}-phenyl)-1H-benzoimidazole

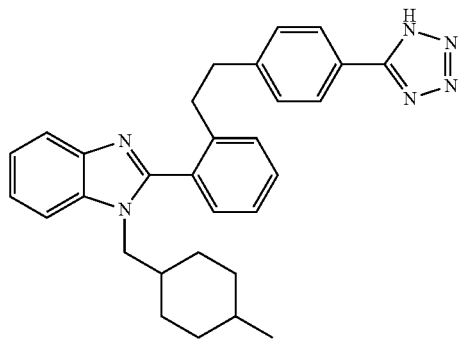

The title compound was prepared in analogy to Example 30, from 4-(2-{2-[1-(4 methyl-cyclohexylmethyl)-1H-benzoimidazol-2-yl]-phenyl}-ethyl)-benzonitrile. Yellow powder (26%). MS (Turbo Spray): m/z=477.4 (M+H).

Intermediates a) 4-(2-{2-[1-(4 Methyl-cyclohexylmethyl)-1H-benzoimidazol-2-yl]-phenyl}-ethyl)-benzonitrile The title compound was prepared in analogy to Example 73, intermediate, from 4-{2-[1-(4-methyl-cyclohexylmethyl)-1H-benzoimidazol-2-yl]-phenylethynyl}-benzonitrile. Brown sticky solid (59%). MS (Turbo Spray): m/z=434.1 (M+H).

114 b) 4-{2-[1-(4-Methyl-cyclohexylmethyl)-1H-benzoimidazol-2-yl]-phenylethynyl}-benzonitrile The title compound was prepared in analogy to Example 72, intermediate a, from 2-(2-bromo-phenyl)-1-(4-methyl-cyclohexylmethyl)-1H-benzoimidazole and 4-ethynyl-benzonitrile (CAS Reg. No. 3032-92-6). Light yellow liquid (25%). MS (Turbo Spray): m/z=430.4 (M+H).

c) 2-(2-Bromo-phenyl)-1-(4-methyl-cyclohexylmethyl)-1H-benzoimidazole

The title compound was prepared in analogy to Example 19, intermediate b, from 2-(2-bromo-phenyl)-5,6-difluoro-1H-benzoimidazole (Example 79, intermediate f) and toluene-4-sulfonic acid 4-methyl-cyclohexylmethyl ester (CAS Reg. No. 92730-50-2). Colorless liquid (50%). MS (Turbo Spray): m/z=384.3 (M+H).

Example 83

1-(2-Cyclohexyl-ethyl)-2-(2-{2-[4-(1H-tetrazol-5-yl)-phenyl]-ethyl}-phenyl)-1H-benzoimidazole

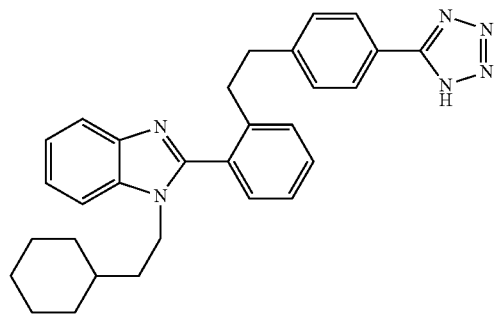

The title compound was prepared in analogy to Example 30, from 4 (2-{2-[1-(2 cyclohexyl-ethyl)-1H-benzoimidazol-2-yl]-phenyl}-ethyl)-benzonitrile. Off-white powder (21%). MS (Turbo Spray): m/z=477.4 (M+H).

Intermediates a) 4-(2-{2-[1-(2 Cyclohexyl-ethyl)-1H-benzoimidazol-2-yl]-phenyl}-ethyl)-benzonitrile The title compound was prepared in analogy to Example 73, intermediate, from 4-{2-[1-(2-cyclohexyl-ethyl)-1H-benzoimidazol-2-yl]-phenylethynyl}-benzonitrile. White solid (58%). MS (Turbo Spray): m/z=434.2 (M+H).

b) 4-{2-[1-(2-Cyclohexyl-ethyl)-1H-benzoimidazol-2-yl]-phenylethynyl}-benzonitrile The title compound was prepared in analogy to Example 72, intermediate a, from 2-(2-bromo-phenyl)-1-(4-methyl-cyclohexylmethyl)-1H-benzoimidazole and 4-ethynyl-benzonitrile (CAS Reg. No. 3032-92-6). White solid (43%). MS (Turbo Spray): m/z=430.2 (M+H).

c) 2-(2-Bromo-phenyl)-1-(2-cyclohexyl-ethyl)-1H-benzoimidazole

The title compound was prepared in analogy to Example 19, intermediate b, from 2-(2-bromo-phenyl)-5,6-difluoro- 1H-benzoimidazole (Example 79, intermediate f) and (2-bromo-ethyl)-cyclohexane (CAS Reg. No. 1647-26-3). Light yellow sticky solid (87%). MS (Turbo Spray): m/z=384.2 (M+H).

Example 84

N-[5-Chloro-2-(1-cyclohexylmethyl-5,6-difluoro-1H-benzoimidazol-2-yl)-phenyl]-2-fluoro-4-(1H-tetrazol-5-yl)-benzamide

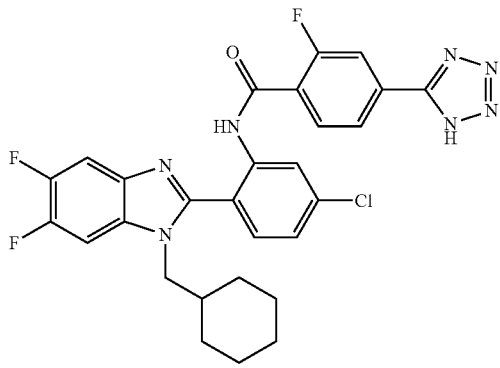

To a stirred solution of 5-chloro-2-(1-cyclohexylmethyl-5,6-difluoro-1H-benzoimidazol-2-yl)-phenylamine (60 mg, 0.16 mmol) in dry tetrahydrofuran (15 ml) was added lithium bis(trimethylsilyl)amide at −30° C. and stirring continued for 30 minutes at that temperature. To this was added a solution of 2-fluoro-4-(1H-tetrazol-5-yl)-benzoic acid methyl ester (42 mg, 0.19 mmol) in tetrahydrofuran (5 ml) at −30° C. The temperature was then allowed to slowly rise to 25° C., and the reaction mixture was allowed to stir for 13 h. The reaction mixture was quenched with saturated aqueous solution of ammonium chloride, extracted with ethyl acetate (3×5 ml). Combined organic layer was washed with brine, dried over sodium sulfate, filtered, and concentrated under reduced pressure. The crude product was purified by column chromatography over silica gel (ethyl acetate to 4% methanol/ethyl acetate) gave the desired final compound as light yellow powder (30%). MS (Turbo Spray): m/z=566.4 (M+H).

Intermediates a) 5-Chloro-2-(1-cyclohexylmethyl-5,6-difluoro-1H-benzoimidazol-2-A-phenylamine To a solution of 2-(4-chloro-2-nitro-phenyl)-1-cyclohexylmethyl-5,6-difluoro-1H-benzoimidazole (270 mg, 0.66 mmol) in methanol (10 ml) were added stannous chloride (631 mg, 3.32 mmol) and concentrated hydrochloric acid (0.1 ml) at 25° C. The reaction mixture was stirred for 16 h under reflux. After the completion of reaction, solvents were evaporated under reduced pressure, diluted with water, neutralized with aqueous solution of 1M sodium hydroxide, and extracted with ethyl acetate (3×20 ml). Combined organic layers were washed with water (2×20 ml), and then with brine, dried over sodium sulfate, filtered, and evaporated under reduced pressure to furnish the desired compound as a light yellow solid (85%). MS (Turbo Spray): m/z=376.2 (M+H).

b) 2-(4-Chloro-2-nitro-phenyl)-1-cyclohexylmethyl-5,6-difluoro-1H-benzoimidazole The title compound was prepared in analogy to Example 19, intermediate b, from 2-(4-Chloro-2-nitro-phenyl)-5,6-difluoro-1H-benzoimidazole and bromomethyl-cyclohexane (CAS Reg. No. 2550-36-9). Off-white powder (43%). MS (Turbo Spray): m/z=406.3 (M+H).

c) 2-(4-Chloro-2-nitro-phenyl)-5,6-difluoro-1H-benzoimidazole

To a solution of 4,5-difluoro-benzene-1,2-diamine (2.0 g, 6.94 mmol; CAS Reg. No. 76179-40-3) in o-xylene (25 ml) was added 4-chloro-2-nitro-benzoic acid (2.78 g, 6.94 mmol; CAS Reg. No. 6280-88-2) and titanium tetraethoxide (2.9 ml, 6.94 mmol) at 25° C., and the reaction mixture was allowed to stir at reflux temperature for 14 h. After the completion of reaction, solvents were evaporated under reduced pressure. The residue was purified by column chromatography over silica gel (18-20% ethyl acetate/n-hexane) to afford the desired compound as a yellow powder (15%). MS (Turbo Spray): m/z=310.2 (M+H).

d) 2-Fluoro-4-(1H-tetrazol-5-yl)-benzoic acid methyl ester

To a solution of 2-fluoro-4-(1H-tetrazol-5-yl)-benzoic acid (100 mg, 0.48 mmol) in methanol (5 ml), thionyl chloride (0.5 ml) was added at 0° C. and the reaction mixture was stirred at 25° C. for 12 h. The solvents were distilled off in vacuo, and the residue was purified by chromatography over silica gel (5% methanol/dichloromethane) to afford the title compound as a yellow solid (58%). MS (Turbo Spray): m/z=222.0 (M+H).

e) 2-Fluoro-4-(1H-tetrazol-5-yl)-benzoic acid

The title compound was prepared in analogy to Example 30, from 4-cyano-2-fluoro-benzoic acid (CAS Reg. No. 164149-28-4). Light yellow solid (71%). MS (Turbo Spray): m/z=208.0 (M+H).

Example 85

N-[5-Chloro-2-(1-cyclohexylmethyl-5,6-difluoro-1H-benzoimidazol-2-yl)-phenyl]-3-fluoro-4-(1H-tetrazol-5-yl)-benzamide

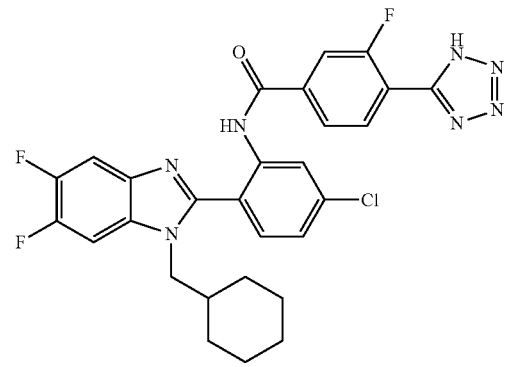

The title compound was prepared in analogy to Example 84, from 5-chloro-2-(1-cyclohexylmethyl-5,6-difluoro-1H-benzoimidazol-2-yl)-phenylamine (Example 84, intermediate a) and 3-fluoro-4-(1H-tetrazol-5-yl)-benzoic acid methyl ester. Off-white powder (35%). MS (Turbo Spray): m/z=566.1 (M+H).

Intermediates a) 3-Fluoro-4-(1H-tetrazol-5-yl)-benzoic acid methyl ester

The title compound was prepared in analogy to Example 84, intermediate d, from 3-fluoro-4-(1H-tetrazol-5-yl)-benzoic acid. Light yellow solid (37%). MS (Turbo Spray): m/z=222.0 (M+H).

b) 3-Fluoro-4-(1H-tetrazol-5-yl)-benzoic acid

The title compound was prepared in analogy to Example 84, intermediate e, from 4-cyano-3-fluoro-benzoic acid (CAS Reg. No. 176508-81-9). Light yellow solid (58%). MS (Turbo Spray): m/z=208 (M+H).

Example 86

2-(1-Cyclohexylmethyl-5,6-difluoro-1H-benzoimidazol-2-yl)-N-[2-fluoro-4-(1H-tetrazol-5-yl)-phenyl]-benzamide

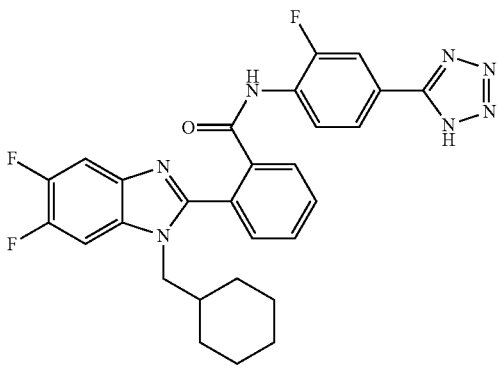

The title compound was prepared in analogy to Example 30, from N-(4-cyano-2-fluoro-phenyl)-2-(1-cyclohexylmethyl-5,6-difluoro-1H-benzoimidazol-2-yl)-benzamide. Yellow powder (46%). MS (Turbo Spray): m/z=532.1 (M+H).

Intermediates a) N-(4-Cyano-2-fluoro-phenyl)-2-(1-cyclohexylmethyl-5,6-difluoro-1H-benzoimidazol-2-yl)-benzamide The title compound was prepared in analogy to Example 85, from 2-(1-cyclohexylmethyl-5,6-difluoro-1H-benzoimidazol-2-yl)-benzoic acid methyl ester and 4-amino-3-fluoro-benzonitrile (CAS Reg. No. 63069-50-1). Off-white powder (65%). MS (Turbo Spray): m/z=489.6 (M+H).

b) 2-(1-Cyclohexylmethyl-5,6-difluoro-1H-benzoimidazol-2-yl)-benzoic acid methyl ester The title compound was prepared in analogy to Example 19, intermediate b, from 2-(5,6-difluoro-1H-benzoimidazol-2-yl)-benzoic acid methyl ester and bromomethyl-cyclohexane (2550-36-9). Off-white powder (15%). MS (Turbo Spray): m/z=384.8 (M+H).

c) 2-(5,6-Difluoro-1H-benzoimidazol-2-yl)-benzoic acid methyl ester

The title compound was prepared in analogy to Example 19, intermediate c, from 4,5-difluoro-benzene-1,2-diamine (CAS Reg. No. 76179-40-3) and phthalic acid monomethyl ester (CAS Reg. No. 4376-18-5). Off-white powder (12%). MS (Turbo Spray): m/z=289.0 (M+H).

Example 87

2-(4-Chloro-2-cyclohexylmethoxy-phenyl)-5,6-difluoro-1-[2-fluoro-4-(1H-tetrazol-5-yl)-benzyl]-1H-benzoimidazole

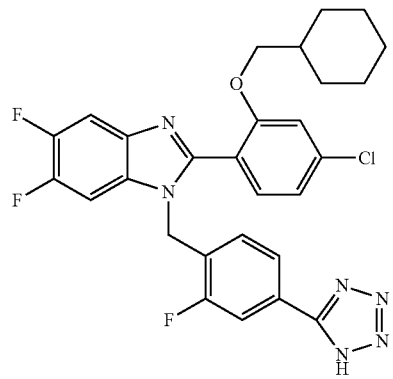

The title compound was prepared in analogy to Example 30, from 4-[2-(4-chloro-2-cyclohexylmethoxy-phenyl)-5,6-difluoro-benzoimidazol-1-ylmethyl]-3-fluoro-benzonitrile. Off-white powder (32%). MS (Turbo Spray): m/z=553.4 (M+H).

Intermediate

4-[2-(4-Chloro-2-cyclohexylmethoxy-phenyl)-5,6-difluoro-benzoimidazol-1-ylmethyl]-3-fluoro-benzonitrile The title compound was prepared in analogy to Example 5, intermediate a, from 4-[2-(4-chloro-2-hydroxy-phenyl)-5,6-difluoro-benzoimidazol-1-ylmethyl]-3-fluoro-benzonitrile (Example 70, intermediate b) and bromomethyl-cyclohexane (CAS Reg. No. 2550-36-9). Colorless solid (71%). MS (Turbo Spray): m/z=510.2 (M+H).

Example 88

2-[4-Chloro-2-(2-ethyl-butoxy)-phenyl]-5,6-difluoro-1-[2-fluoro-4-(1H-tetrazol-5-yl)-benzyl]-1H-benzoimidazole

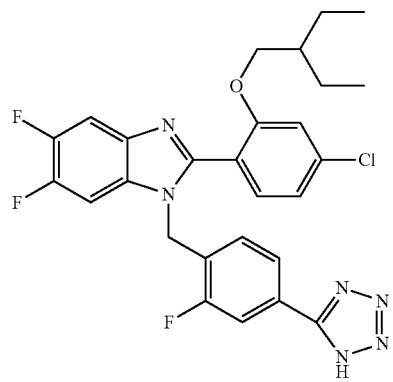

The title compound was prepared in analogy to Example 30, from 4-{2-[4-chloro-2-(2-ethyl-butoxy)-phenyl]-5,6-difluoro-benzoimidazol-1-ylmethyl}-3-fluoro-benzonitrile. Yellow powder (55%). MS (Turbo Spray): m/z=541.2 (M+H).

Intermediate

4-{2-[4-Chloro-2-(2-ethyl-butoxy)-phenyl]-5,6-difluoro-benzoimidazol-1-ylmethyl}-3-fluoro-benzonitrile The title compound was prepared in analogy to Example 5, intermediate a, from 4-[2-(4-chloro-2-hydroxy-phenyl)-5,6-difluoro-benzoimidazol-1-ylmethyl]-3-fluoro-benzonitrile (Example 70, intermediate b) and 3-bromomethyl-pentane (CAS Reg. No. 3814-34-4). Off-white powder (66%). MS (Turbo Spray): m/z=498.0 (M+H).

Example 89

2-(4-Chloro-2-cyclopropylmethoxy-phenyl)-5,6-difluoro-1-[2-fluoro-4-(1H-tetrazol-5-yl)-benzyl]-1H-benzoimidazole

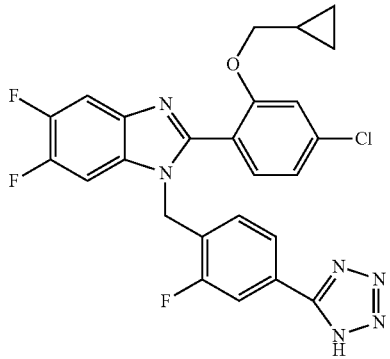

The title compound was prepared in analogy to Example 30, from 4-[2-(4-chloro-2-cyclopropylmethoxy-phenyl)-5,6-difluoro-benzoimidazol-1-ylmethyl]-3-fluoro-benzonitrile. Yellow powder (65%). MS (Turbo Spray): m/z=511.0 (M+H).

Intermediate

4-[2-(4-Chloro-2-cyclopropylmethoxy-phenyl)-5,6-difluoro-benzoimidazol-1-ylmethyl]-3-fluoro-benzonitrile The title compound was prepared in analogy to Example 5, intermediate a, from 4-[2-(4-chloro-2-hydroxy-phenyl)-5,6-difluoro-benzoimidazol-1-ylmethyl]-3-fluoro-benzonitrile (Example 70, intermediate b) and bromomethyl-cyclopropane (CAS Reg. No. 7051-34-5). Colorless solid (90%). MS (Turbo Spray): m/z=468.0 (M+H).

Example 90

2-[4-Chloro-2-(tetrahydro-pyran-4-ylmethoxy)-phenyl]-5,6-difluoro-1-[2-fluoro-4-(1H-tetrazol-5-yl)-benzyl]-1H-benzoimidazole

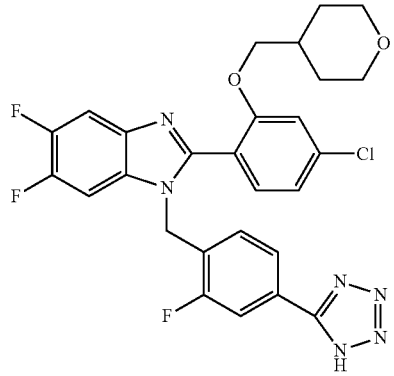

The title compound was prepared in analogy to Example 30, from 4-{2-[4-chloro-2-(tetrahydro-pyran-4-ylmethoxy)-phenyl]-5,6-difluoro-benzoimidazol-1-ylmethyl}-3-fluoro-benzonitrile. Yellow powder (32%). MS (Turbo Spray): m/z=555.0 (M+H).

Intermediate

4-{2-[4-Chloro-2-(tetrahydro-pyran-4-ylmethoxy)-phenyl]-5,6-difluoro-benzoimidazol-1-ylmethyl}-3-fluoro-benzonitrile The title compound was prepared in analogy to Example 5, intermediate a, from 4-[2-(4-chloro-2-hydroxy-phenyl)-5,6-difluoro-benzoimidazol-1-ylmethyl]-3-fluoro-benzonitrile (Example 70, intermediate b) and 4-bromomethyl-tetrahydro-pyran (CAS Reg. No. 125552-89-8). Colorless solid (64%). MS (Turbo Spray): m/z=512.0 (M+H).

Example 91

2-(4-Chloro-2-propoxy-phenyl)-5,6-difluoro-1-[2-fluoro-4-(1H-tetrazol-5-yl)-benzyl]-1H-benzoimidazole

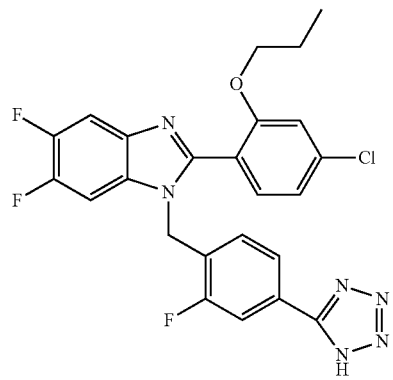

The title compound was prepared in analogy to Example 30, from 4-[2-(4-chloro-2-propoxy-phenyl)-5,6-difluoro-benzoimidazol-1-ylmethyl]-3-fluoro-benzonitrile. Yellow powder (46%). MS (Turbo Spray): m/z=499.0 (M+H).

Intermediate

4-[2-(4-Chloro-2-propoxy-phenyl)-5,6-difluoro-benzoimidazol-1-ylmethyl]-3-fluoro-benzonitrile The title compound was prepared in analogy to Example 5, intermediate a, from 4-[2-(4-chloro-2-hydroxy-phenyl)-5,6-difluoro-benzoimidazol-1-ylmethyl]-3-fluoro-benzonitrile (Example 70, intermediate b) and 1-bromo-propane (CAS Reg. No. 106-94-5). Colorless solid (72%). MS (Turbo Spray): m/z=455.9 (M+H).

Example 92

2-(4-Chloro-2-cyclobutylmethoxy-phenyl)-5,6-difluoro-1-[2-fluoro-4-(1H-tetrazol-5-yl)-benzyl]-1H-benzoimidazole

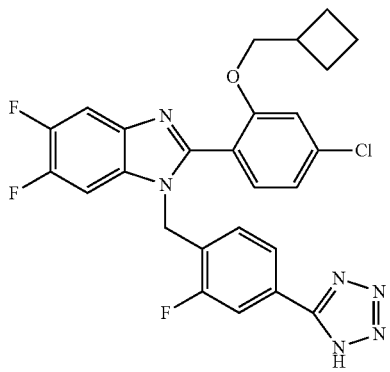

The title compound was prepared in analogy to Example 30, from 4-[2-(4-chloro-2-cyclobutylmethoxy-phenyl)-5,6-difluoro-benzoimidazol-1-ylmethyl]-3-fluoro-benzonitrile. Light yellow powder (28%). MS (Turbo Spray): m/z=525.2 (M+H).

Intermediate

4-[2-(4-Chloro-2-cyclobutylmethoxy-phenyl)-5,6-difluoro-benzoimidazol-1-ylmethyl]-3-fluoro-benzonitrile The title compound was prepared in analogy to Example 5, intermediate a, from 4-[2-(4-chloro-2-hydroxy-phenyl)-5,6-difluoro-benzoimidazol-1-ylmethyl]-3-fluoro-benzonitrile (Example 70, intermediate b) and bromomethyl-cyclobutane (CAS Reg. No. 17247-58-4). Colorless solid (82%). MS (Turbo Spray): m/z=482.4 (M+H).

Example 93

2-[4-Chloro-2-(tetrahydro-pyran-2-ylmethoxy)-phenyl]-5,6-difluoro-1-[2-fluoro-4-(1H-tetrazol-5-yl)-benzyl]-1H-benzoimidazole

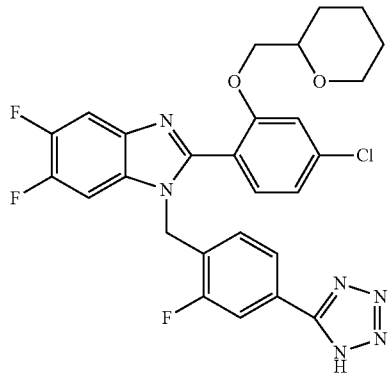

The title compound was prepared in analogy to Example 30, from 4-[2-[4-chloro-2-(tetrahydro-pyran-2-ylmethoxy)-phenyl]-5,6-difluoro-benzoimidazol-1-ylmethyl]-3-fluoro-benzonitrile. Off-white powder (55%). MS (Turbo Spray): m/z=555.2 (M+H).

Intermediate

4-{2-[4-Chloro-2-(tetrahydro-pyran-2-ylmethoxy)-phenyl]-5,6-difluoro-benzoimidazol-1-ylmethyl}-3-fluoro-benzonitrile The title compound was prepared in analogy to Example 5, intermediate a, from 4-[2-(4-chloro-2-hydroxy-phenyl)-5,6-difluoro-benzoimidazol-1-ylmethyl]-3-fluoro-benzonitrile (Example 70, intermediate b) and (2-bromomethyl)-tetrahydro-pyran (CAS Reg. No. 34723-82-5). Colorless sticky liquid (41%). MS (Turbo Spray): m/z=512.0 (M+H).

Example 94

2-(2-Cyclopentylmethoxy-phenyl)-5,6-difluoro-1-[2-fluoro-4-(1H-tetrazol-5-yl)-benzyl]-1H-benzoimidazole

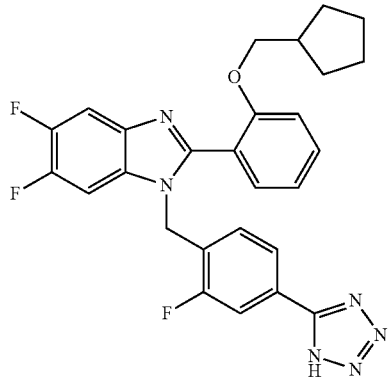

The title compound was prepared in analogy to Example 30, from 4-[2-(2-cyclopentylmethoxy-phenyl)-5,6-difluoro-benzoimidazol-1-ylmethyl]-3-fluoro-benzonitrile. Light yellow powder (30%). MS (Turbo Spray): m/z=505.1 (M+H).

Intermediates a) 4-[2-(2-Cyclopentylmethoxy-phenyl)-5,6-difluoro-benzoimidazol-1-ylmethyl]-3-fluoro-benzonitrile The title compound was prepared in analogy to Example 5, intermediate a, from 4-[5,6-difluoro-2-(2-hydroxy-phenyl)-benzoimidazol-1-ylmethyl]-3-fluoro-benzonitrile and iodomethyl-cyclopentane (CAS Reg. No. 27935-87-1). Off-white solid (51%). MS (Turbo Spray): m/z=462.2 (M+H).

b) 4-[5,6-Difluoro-2-(2-hydroxy-phenyl)-benzoimidazol-1-ylmethyl]-3-fluoro-benzonitrile The title compound was prepared in analogy to Example 19, intermediate a, from 4-[5,6-difluoro-2-(2-methoxy-phenyl)-benzoimidazol-1-ylmethyl]-3-fluoro-benzonitrile. Light orange solid (95%). MS (Turbo Spray): m/z=380.2 (M+H).

c) 4-[5,6-Difluoro-2-(2-methoxy-phenyl)-benzoimidazol-1-ylmethyl]-3-fluoro-benzonitrile The title compound was prepared in analogy to Example 19, intermediate b, from 5,6-difluoro-2-(2-methoxy-phenyl)-1H-benzoimidazole (Example 34, intermediate d) and 4-bromomethyl-3-fluoro-benzonitrile (CAS Reg. No. 105942-09-4). Blue solid (32%). MS (Turbo Spray): m/z=394.4 (M+H).

Example 95

2-(4-Chloro-2-cyclopentylmethoxy-phenyl)-1-[2-fluoro-4-(1H-tetrazol-5-yl)-benzyl]-1H-benzoimidazole

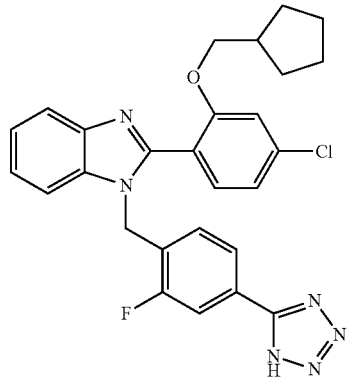

The title compound was prepared in analogy to Example 30, from 4-[2-(4-chloro-2-cyclopentylmethoxy-phenyl)-benzoimidazol-1-ylmethyl]-3-fluoro-benzonitrile. Yellow powder (65%). MS (Turbo Spray): m/z=503.0 (M+H).

Intermediates a) 4-[2-(4-Chloro-2-cyclopentylmethoxy-phenyl)-benzoimidazol-1-ylmethyl]-3-fluoro-benzonitrile The title compound was prepared in analogy to Example 5, intermediate a, from 4-[2-(4-chloro-2-hydroxy-phenyl)-benzoimidazol-1-ylmethyl]-3-fluoro-benzonitrile and iodomethyl-cyclopentane (CAS Reg. No. 27935-87-1). Light yellow sticky solid (35%). MS (Turbo Spray): m/z=460.2 (M+H).

b) 4-[2-(4-Chloro-2-hydroxy-phenyl)-benzoimidazol-1-ylmethyl]-3-fluoro-benzonitrile The title compound was prepared in analogy to Example 19, intermediate a, from 4-[2-(4-chloro-2-methoxy-phenyl)-benzoimidazol-1-ylmethyl]-3-fluoro-benzonitrile. Light yellow sticky solid (92%). MS (Turbo Spray): m/z=378.4 (M+H).

c) 4-[2-(4-Chloro-2-methoxy-phenyl)-benzoimidazol-1-ylmethyl]-3-fluoro-benzonitrile The title compound was prepared in analogy to Example 19, intermediate b, from 2-(4-chloro-2-methoxy-phenyl)-1H-benzoimidazole (Example 39, intermediate d) and 4-bromomethyl-3-fluoro-benzonitrile (CAS Reg. No. 105942-09-4). Yellow solid (18%). MS (Turbo Spray): m/z=392.4 (M+H).

Example 96

2-(4-Chloro-2-cyclohexyloxy-phenyl)-5,6-difluoro-1-[2-fluoro-4-(1H-tetrazol-5-yl)-benzyl]-1H-benzoimidazole

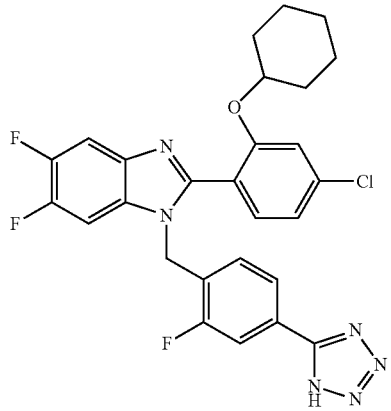

The title compound was prepared in analogy to Example 30, from 4-[2-(4-chloro-2-cyclohexyloxy-phenyl)-5,6-difluoro-benzoimidazol-1-ylmethyl]-3-fluoro-benzonitrile. Yellow powder (23%). MS (Turbo Spray): m/z=539.2 (M+H).

Intermediate

4-[2-(4-Chloro-2-cyclohexyloxy-phenyl)-5,6-difluoro-benzoimidazol-1-ylmethyl]-3-fluoro-benzonitrile The title compound was prepared in analogy to Example 5, intermediate a, from 4-[2-(4-chloro-2-hydroxy-phenyl)-5,6-difluoro-benzoimidazol-1-ylmethyl]-3-fluoro-benzonitrile (Example 70, intermediate b) and bromo-cyclohexane (CAS Reg. No. 108-85-0). Colorless semi-solid (22%). MS (Turbo Spray): m/z=496.2 (M+H).

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound according to formula (I),

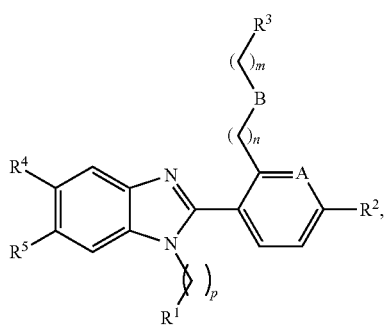

wherein
R$^1$ is selected from the group consisting of: cyclokexyl, substituted cyclohexyl, phenyl, and substituted phenyl and substituted phenyl are substituted with one to three substituents independently selected from the group consisting of: alkyl, haloalkyl, halogen, hydroxy, alkoxy, hydroxyalkyl, carboxy, carboxyalkyl, carboxyalkoxy, alkoxycarbonyl, alkoxycarbonylalkyl, alkoxycarbonylalkoxy, cyano, tetrazolyl and tetrazolylalkyl;
R$^2$ is selected from the group consisting of: hydrogen, alkyl and halogen;
R$^3$ is cycloalkyl or substituted phenyl wherein said substituted phenyl is phenyl substituted with one to three substituents independently selected from the group consisting of: halogen, carboxy, carboxyalkoxy and tetrazolyl;
R$^4$ is hydrogen or halogen;
R$^5$ is hydrogen or halogen;
A is CH;
B is —O—;
n is zero, 1 or 2;
m is zero, 1 or 2; and
p is 1 or 2;
or a pharmaceutically acceptable salt thereof;
with the proviso that 1-benzyl-2-(2-benzyloxy-phenyl)-1H-benzoimidazole is excluded.

2. A compound according to claim 1, wherein R$^1$ is cyclohexyl or substituted phenyl, wherein said substituted phenyl is phenyl substituted with one to three substituents independently selected from halogen and tetrazolyl.

3. A compound according to claim 1, wherein R$^1$ is cyclohexyl.

4. A compound according to claim 1, wherein R$^3$ is substituted phenyl wherein said substituted phenyl is phenyl substituted with one to three substituents independently selected from halogen and tetrazolyl.

5. A compound according to claim 1, wherein R$^2$ is halogen.

6. A compound according to claim 1, selected from the group consisting of:
2-(4-Chloro-2-cyclopentylmethoxy-phenyl)-1-cyclohexylmethyl-5,6-difluoro-1H-benzoimidazole;
2-(4-Chloro-2-cyclohexylmethoxy-phenyl)-1-cyclohexylmethyl-5,6-difluoro-1H-benzoimidazole;
4-[5-Chloro-2-(1-cyclohexylmethyl-5,6-difluoro-1H-benzoimidazol-2-yl)-phenoxymethyl]-benzoic acid;
{4-[5-Chloro-2-(1-cyclohexylmethyl-5,6-difluoro-1H-benzoimidazol-2-yl)-phenoxymethyl]-phenoxy}-acetic acid;
2-{4-Chloro-2-[4-(1H-tetrazol-5-yl)-benzyloxy]-phenyl}-1-cyclohexylmethyl-5,6-difluoro-1H-benzoimidazole;
2-{4-Chloro-2-[2-fluoro-4-(1H-tetrazol-5-yl)-benzyloxy]-phenyl}-1-cyclohexylmethyl-5,6-difluoro-1H-benzoimidazole;
2-{4-Chloro-2-[3-fluoro-4-(1H-tetrazol-5-yl)-benzyloxy]-phenyl}-1-cyclohexylmethyl-5,6-difluoro-1H-benzoimidazole;
1-Cyclohexylmethyl-5,6-difluoro-2-{2-[2-fluoro-4-(1H-tetrazol-5-yl)-phenoxymethyl]-phenyl}-1H-benzoimidazole;
2-{4-Chloro-2-[2fluoro-4-(1H-tetrazol-5-yl)-benzyloxy]-phenyl}-1-(2-cyclohexyl-ethyl)-5,6-difluoro-1H-benzoimidazole;
2-(4-Chloro-2-cyclopentylmethoxy-phenyl)-5,6-difluoro-1-[3-fluoro-4-(1H-tetrazol-5-yl)-benzyl]-1H-benzoimidazole; and
2-(4-Chloro-2-cyclopentylmethoxy-phenyl)-5,6-difluoro-1-[2-fluoro-4-(1H-tetrazol-5-yl)-benzyl]-1H-benzoimidazole.

7. A pharmaceutical composition comprising a compound according to claim 1 and a therapeutically inert carrier.

8. A compound according to claim 1, selected from the group consisting of:
2-[4-Chloro-2-(2-chloro-benzyloxy)-phenyl]-1-cyclohexylmethyl-5,6-difluoro-1H-benzoimidazole;
2-(4-Chloro-2-cyclopentylmethoxy-phenyl)-1-cyclohexylmethyl-5,6-difluoro-1H-benzoimidazole;
2-(4-Chloro-2-cyclopropylmethoxy-phenyl)-1-cyclohexylmethyl-5,6-difluoro-1H-benzoimidazole;

2-(4-Chloro-2-cyclohexylmethoxy-phenyl)-1-cyclohexylmethyl-5,6-difluoro-1H-benzoimidazole;
4-[5-Chloro-2-(1-cyclohexylmethyl-5,6-difluoro-1H-benzoimidazol-2-yl)-phenoxymethyl]-benzoic acid;
3-[5-Chloro-2-(1-cyclohexylmethyl-5,6-difluoro-1H-benzoimidazol-2-yl)-phenoxymethyl]-benzoic acid;
{4-[5-Chloro-2-(1-cyclohexylmethyl-5,6-difluoro-1H-benzoimidazol-2-yl)-phenoxymethyl]-phenoxy}-acetic acid;
4-{2-[5-Chloro-2-(1-cyclohexylmethyl-5,6-difluoro-1H-benzoimidazol-2-yl)-phenoxy]-ethyl}-benzoic acid; and
{4-[5-Chloro-2-(1-cyclohexylmethyl-5,6-difluoro-1H-benzoimidazol-2-yl)-phenoxymethyl]-phenyl}-acetic acid.

9. A compound according to claim 1, selected from the group consisting of:
2-{4-Chloro-2-[3-(1H-tetrazol-5-yl)-benzyloxy]-phenyl}-1-cyclohexylmethyl-5,6-difluoro-1H-benzoimidazole;
2-{4-Chloro-2-[4-(1H-tetrazol-5-yl)-benzyloxy]-phenyl}-1-cyclohexylmethyl-5,6-difluoro-1H-benzoimidazole;
2-{4-Chloro-2-[2-fluoro-4-(1H-tetrazol-5-yl)-benzyloxy]-phenyl}-1-cyclohexylmethyl-5,6-difluoro-1H-benzoimidazole;
2-{4-Chloro-2-[3-fluoro-4-(1H-tetrazol-5-yl)-benzyloxy]-phenyl}-1-cyclohexylmethyl-5,6-difluoro-1H-benzoimidazole;
1-Cyclohexylmethyl-5,6-difluoro-2-{2-[2-fluoro-4-(1H-tetrazol-5-yl)-benzyloxy]-phenyl}-1H-benzoimidazole;
2-{4-Chloro-2-[2-methoxy-4-(1H-tetrazol-5-yl)-benzyloxy]-phenyl}-1-cyclohexylmethyl-5,6-difluoro-1H-benzoimidazole; and
2-(4-Chloro-2-{2-[4-(1H-tetrazol-5-yl)-phenyl]-ethoxy}-phenyl)-1-cyclohexylmethyl-5,6-difluoro-1H-benzoimidazole.

10. A compound according to claim 1, selected from the group consisting of:
1-Benzyl-2-(4-chloro-2-cyclopentylmethoxy-phenyl)-5,6-difluoro-1H-benzoimidazole;
1-Benzyl-2-(4-chloro-2-cyclopropylmethoxy-phenyl)-5,6-difluoro-1H-benzoimidazole;
4-[2-(1-Benzyl-5,6-difluoro-1H-benzoimidazol-2-yl)-5-chloro-phenoxymethyl]-benzoic acid; and
{4-[2-(1-Benzyl-5,6-difluoro-1H-benzoimidazol-2-yl)-5-chloro-phenoxymethyl]-phenoxy}-acetic acid.

11. A compound according to claim 1, selected from the group consisting of:
1-(3-Chloro-benzyl)-2-(4-chloro-2-cyclopentylmethoxy-phenyl)-5,6-difluoro-1H-benzoimidazole;
1-(3-Chloro-benzyl)-2-(4-chloro-2-cyclopropylmethoxy-phenyl)-5,6-difluoro-1H-benzoimidazole;
4-{5-Chloro-2-[1-(3-chloro-benzyl)-5,6-difluoro-1H-benzoimidazol-2-yl]-phenoxymethyl}-benzoic acid;
(4-{5-Chloro-2-[1-(3-chloro-benzyl)-5,6-difluoro-1H-benzoimidazol-2-yl]-phenoxymethyl}-phenoxy)-acetic acid;
3-(4-{2-[4-Chloro-2-(2-chloro-benzyloxy)-phenyl]-5,6-difluoro-benzoimidazol-1-ylmethyl}-phenyl)-propionic acid;
3-{4-[2-(4-Chloro-2-cyclopentylmethoxy-phenyl)-5,6-difluoro-benzoimidazol-1-ylmethyl]-phenyl}-propionic acid;
3-{4-[2-(4-Chloro-2-cyclopropylmethoxy-phenyl)-5,6-difluoro-benzoimidazol-1-ylmethyl]-phenyl}-propionic acid;
3-[2-(4-Chloro-2-cyclopentylmethoxy-phenyl)-5,6-difluoro-benzoimidazol-1-ylmethyl]-benzoic acid;
4-[2-(4-Chloro-2-cyclopentylmethoxy-phenyl)-5,6-difluoro-benzoimidazol-1-ylmethyl]-benzoic acid; and
{4-[2-(4-Chloro-2-cyclopentylmethoxy-phenyl)-5,6-difluoro-benzoimidazol-1-ylmethyl]-phenyl}-acetic acid.

12. A compound according to claim 1, selected from the group consisting of:
{4-[2-(4-Chloro-2-cyclopentylmethoxy-phenyl)-5,6-difluoro-benzoimidazol-1-ylmethyl]-phenoxy}-acetic acid;
4-[2-(4-Chloro-2-cyclopentylmethoxy-phenyl)-5,6-difluoro-benzoimidazol-1-ylmethyl]-cyclohexanecarboxylic acid;
2-(4-Chloro-2-cyclopentylmethoxy-phenyl)-5,6-difluoro-1-[3-(1H-tetrazol-5-yl)-benzyl]-1H-benzoimidazole;
2-(4-Chloro-2-cyclopentylmethoxy-phenyl)-5,6-difluoro-1-[4-(1H-tetrazol-5-yl)-benzyl]-1H-benzoimidazole;
2-(4-Chloro-2-cyclopentylmethoxy-phenyl)-5,6-difluoro-1-[3-fluoro-4-(1H-tetrazol-5-yl)-benzyl]-1H-benzoimidazole;
2-(4-Chloro-2-cyclopentylmethoxy-phenyl)-5,6-difluoro-1-[2-fluoro-4-(1H-tetrazol-5-yl)-benzyl]-1H-benzoimidazole;
2-(4-Chloro-2-cyclohexylmethoxy-phenyl)-5,6-difluoro-1[-2-fluoro-4-(1H-tetrazol-5-yl)-benzyl]-1H-benzoimidazole;
2-(4-Chloro-2-cyclopropylmethoxy-phenyl)-5,6-difluoro-1-[2-fluoro-4-(1H-tetrazol-5-yl)-benzyl]-1H-benzoimidazole.

13. A compound according to claim 1, selected from the group consisting of:
2-(4-Chloro-2-cyclobutylmethoxy-phenyl)-5,6-difluoro-1-[2-fluoro-4-(1H-tetrazol-5-yl)-benzyl]-1H-benzoimidazole;
2-(2-Cyclopentylmethoxy-phenyl)-5,6-difluoro-1-[2-fluoro-4-(1H-tetrazol-5-yl)-benzyl]-1H-benzoimidazole;
2-(4-Chloro-2-cyclopentylmethoxy-phenyl)-1-[2-fluoro-4-(1H-tetrazol-5-yl)-benzyl]-1H-benzoimidazole; and
2-(4-Chloro-2-cyclohexyloxy-phenyl)-5,6-difluoro-1-[2-fluoro-4-(1H-tetrazol-5-yl)-benzyl]-1H-benzoimidazole.

* * * * *